United States Patent
Zeng et al.

(10) Patent No.: US 9,773,985 B2
(45) Date of Patent: Sep. 26, 2017

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Edward Barron, Hamilton, NJ (US); Bin Ma, Plainsboro, NJ (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 594 days.

(21) Appl. No.: 13/798,839

(22) Filed: Mar. 13, 2013

(65) Prior Publication Data

US 2013/0306940 A1  Nov. 21, 2013

Related U.S. Application Data

(60) Provisional application No. 61/649,463, filed on May 21, 2012.

(51) Int. Cl.
*H01L 51/50* (2006.01)
*H01L 51/00* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC ................. C07F 15/0033; C09K 11/06; C09K 2211/185; C09K 2211/1044;
(Continued)

(56) References Cited

U.S. PATENT DOCUMENTS 4,769,292 A    9/1988  Tang et al.
5,061,569 A   10/1991  VanSlyke et al.
(Continued)

FOREIGN PATENT DOCUMENTS

EP   0650955    5/1995
EP   1725079   11/2006
(Continued)

OTHER PUBLICATIONS

H. Sasabe and J. Kido, Multifunctional Materials in High-Performance OLEDs: Challenges for Solid-State Lighting, Dec. 1, 2010, Chemistry of Materials, vol. 23, pp. 621-630.*
(Continued)

*Primary Examiner* — Andrew K Bohaty
*Assistant Examiner* — Dylan Kershner
(74) *Attorney, Agent, or Firm* — Duane Morris LLP

(57) ABSTRACT

A compound according to Formula I, as well as, devices and formulations containing the compound as described. The compound has the general formula

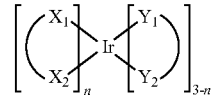

Formula I wherein n=1 or 2; wherein $X_1$-$X_2$ is a bidentate ligand having the formula:
(Continued)

Formula I

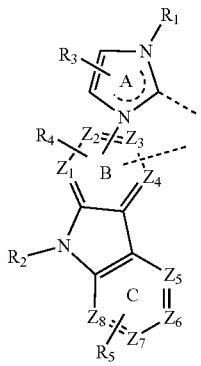

Formula II wherein each of $R_1$, $R_2$, $R_3$, $R_4$ and $R_5$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein each of $R_3$, $R_4$ and $R_5$ can also be selected from two adjacent substituents joined to form into a ring;

wherein each of $Z_1$, $Z_2$, $Z_3$, $Z_4$, $Z_6$, $Z_7$, $Z_8$ is independently selected from C, CH or N;

wherein ring A is connected to ring B through N—C bond; and wherein $Y_1$-$Y_2$ is a different bidentate ligand other than $X_1$-$X_2$.

33 Claims, 3 Drawing Sheets

(51) Int. Cl.
  C07F 15/00 (2006.01)
  C09K 11/06 (2006.01)
(52) U.S. Cl.
  CPC ........... C09K 2211/1029 (2013.01); C09K 2211/1044 (2013.01); C09K 2211/185 (2013.01); H01L 51/5016 (2013.01); H01L 2251/308 (2013.01)
(58) Field of Classification Search
  CPC ........ C09K 2211/1029; H01L 51/0085; H01L 51/50; H01L 51/5016; H01L 2251/308
  USPC ......... 428/690, 917, 691; 313/504, 500–503, 313/505–512; 257/40, E51.043, E51.044, 257/88–104, E51.042, E51.045–E51.052, 257/E51.001–E51.041; 548/103; 427/58, 427/66; 252/301.16–301.35
  See application file for complete search history.

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 7,902,374 B2 * | 3/2011 | Lin et al. | 548/103 |
| 8,586,203 B2 * | 11/2013 | Kwong et al. | 428/690 |
| 9,051,344 B2 * | 6/2015 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 * | 7/2004 | Igarashi et al. | 428/690 |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0249970 A1 * | 11/2005 | Suzuri et al. | 428/690 |
| 2005/0260441 A1 | 11/2005 | Thompson et al. | |
| 2005/0260448 A1 * | 11/2005 | Lin et al. | 428/690 |
| 2005/0260449 A1 | 11/2005 | Walters et al. | |
| 2006/0008670 A1 | 1/2006 | Lin et al. | |
| 2006/0024522 A1 * | 2/2006 | Thompson | 428/690 |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0247061 A1 * | 10/2007 | Adamovich et al. | 313/504 |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2010/0244004 A1 * | 9/2010 | Xia et al. | 257/40 |
| 2010/0244007 A1 * | 9/2010 | Ono | C09K 11/06 257/40 |
| 2011/0057559 A1 * | 3/2011 | Xia et al. | 313/504 |

(56) References Cited

U.S. PATENT DOCUMENTS

2012/0261651 A1* 10/2012 Noto ............... C09K 11/06
257/40

FOREIGN PATENT DOCUMENTS

| | | | | |
|---|---|---|---|---|
| EP | 2034538 | 3/2009 | | |
| JP | 200511610 | 1/2005 | | |
| JP | WO 2005097943 A1 * | 10/2005 | ............. | C09K 11/06 |
| JP | 2007123392 | 5/2007 | | |
| JP | 2007254297 | 10/2007 | | |
| JP | 2008074939 | 4/2008 | | |
| JP | 2008210941 A * | 9/2008 | | |
| JP | 2008214244 A * | 9/2008 | | |
| JP | 2009013366 A * | 1/2009 | | |
| JP | WO 2009008367 A1 * | 1/2009 | .......... | C07F 15/0033 |
| JP | WO 2011021385 A1 * | 2/2011 | ............. | C09K 11/06 |
| WO | 0139234 | 5/2001 | | |
| WO | 0202714 | 1/2002 | | |
| WO | 0215645 | 2/2002 | | |
| WO | 03040257 | 5/2003 | | |
| WO | 03060956 | 7/2003 | | |
| WO | 2004093207 | 10/2004 | | |
| WO | 2004107822 | 12/2004 | | |
| WO | 2005014551 | 2/2005 | | |
| WO | 2005/019373 A2 | 3/2005 | | |
| WO | 2005019373 | 3/2005 | | |
| WO | 2005030900 | 4/2005 | | |
| WO | 2005089025 | 9/2005 | | |
| WO | 2005/113704 A2 | 12/2005 | | |
| WO | 2005123873 | 12/2005 | | |
| WO | 2006009024 | 1/2006 | | |
| WO | 2006056418 | 6/2006 | | |
| WO | 2006072002 | 7/2006 | | |
| WO | 2006082742 | 8/2006 | | |
| WO | 2006098120 | 9/2006 | | |
| WO | 2006100298 | 9/2006 | | |
| WO | 2006103874 | 10/2006 | | |
| WO | 2006114966 | 11/2006 | | |
| WO | 2006132173 | 12/2006 | | |
| WO | 2007002683 | 1/2007 | | |
| WO | 2007004380 | 1/2007 | | |
| WO | 2007063754 | 6/2007 | | |
| WO | 2007063796 | 6/2007 | | |
| WO | 2008056746 | 5/2008 | | |
| WO | 2008101842 | 8/2008 | | |
| WO | 2008132085 | 11/2008 | | |
| WO | 2009000673 | 12/2008 | | |
| WO | 2009003898 | 1/2009 | | |
| WO | 2009008311 | 1/2009 | | |
| WO | 2009018009 | 2/2009 | | |
| WO | WO 2009021126 A2 * | 2/2009 | | |
| WO | 2009050290 | 4/2009 | | |
| WO | 2009021126 | 5/2009 | | |
| WO | 2009062578 | 5/2009 | | |
| WO | 2009063833 | 5/2009 | | |
| WO | 2009066778 | 5/2009 | | |
| WO | 2009066779 | 5/2009 | | |
| WO | 2009086028 | 7/2009 | | |
| WO | 2009100991 | 8/2009 | | |

OTHER PUBLICATIONS

Wong et al., "Multifunctional Iridium Complexes Based on Carbazole Modules as Highly Efficient Electrophosphors", Angew. Chem. Int. Ed., 2006, vol. 45, pp. 7800-7803.*

Inoue et al., Machine translation of WO 2005/097943 A1, Date of Japanese language publication: 2005, pp. 1-49.*

Oshiyama et al., Machine translation of JP 2008-210941 A, Date of Japanese language publication: 2008, pp. 1-45.*

Oshiyama et al., Machine translation of JP 2009-013366 A, Date of Japanese language publication: 2009, pp. 1-52.*

Otsu et al., Machine translation of WO 2009/008367 A1, Date of Japanese language publication: 2005, pp. 1-35.*

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

(56) References Cited

OTHER PUBLICATIONS

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5'-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 88:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

Formula I

ORGANIC ELECTROLUMINESCENT MATERIALS AND DEVICES

CROSS-REFERENCE TO RELATED APPLICATIONS

This application claims priority to U.S. Patent Application Ser. No. 61/649,463 filed May 21, 2012, the entire content of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

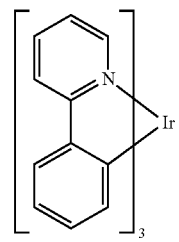

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is provided that has the structure of Formula I shown below

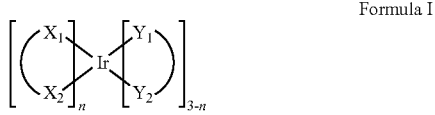

Formula I wherein n=1 or 2;
wherein $X_1$-$X_2$ is a bidentate ligand having the formula:

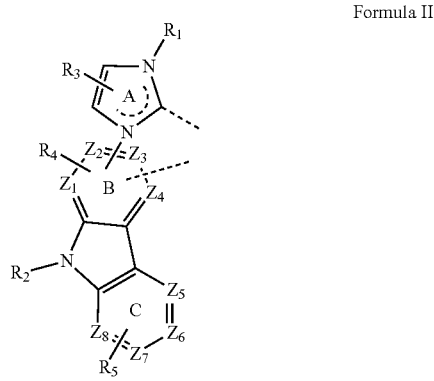

Formula II wherein each of $R_1$, $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R_3$, $R_4$ and $R_5$ may represent mono, di, tri, tetra substitutions, or no substitution;
wherein each of $R_3$, $R_4$ and $R_5$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents are optionally joined to form into a ring;
wherein each of $Z_1$, $Z_2$, $Z_3$, $Z_4$, $Z_6$, $Z_7$, $Z_8$ is independently selected from C, CH or N;
wherein ring A is connected to ring B through N—C bond; and
wherein $Y_1$-$Y_2$ is a different bidentate ligand other than $X_1$-$X_2$.

According to another embodiment, a first device comprising a first organic light emitting device is also provided. The first device can include an anode, a cathode, and an organic layer, disposed between the anode and the cathode. The organic layer can include a compound of Formula I. The first device can be a consumer product, an organic light-emitting device, and/or a lighting panel.

According to still another embodiment, a formulation that includes a compound of Formula I is provided.

BRIEF DESCRIPTION OF THE DRAWINGS

The present disclosure is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawings.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
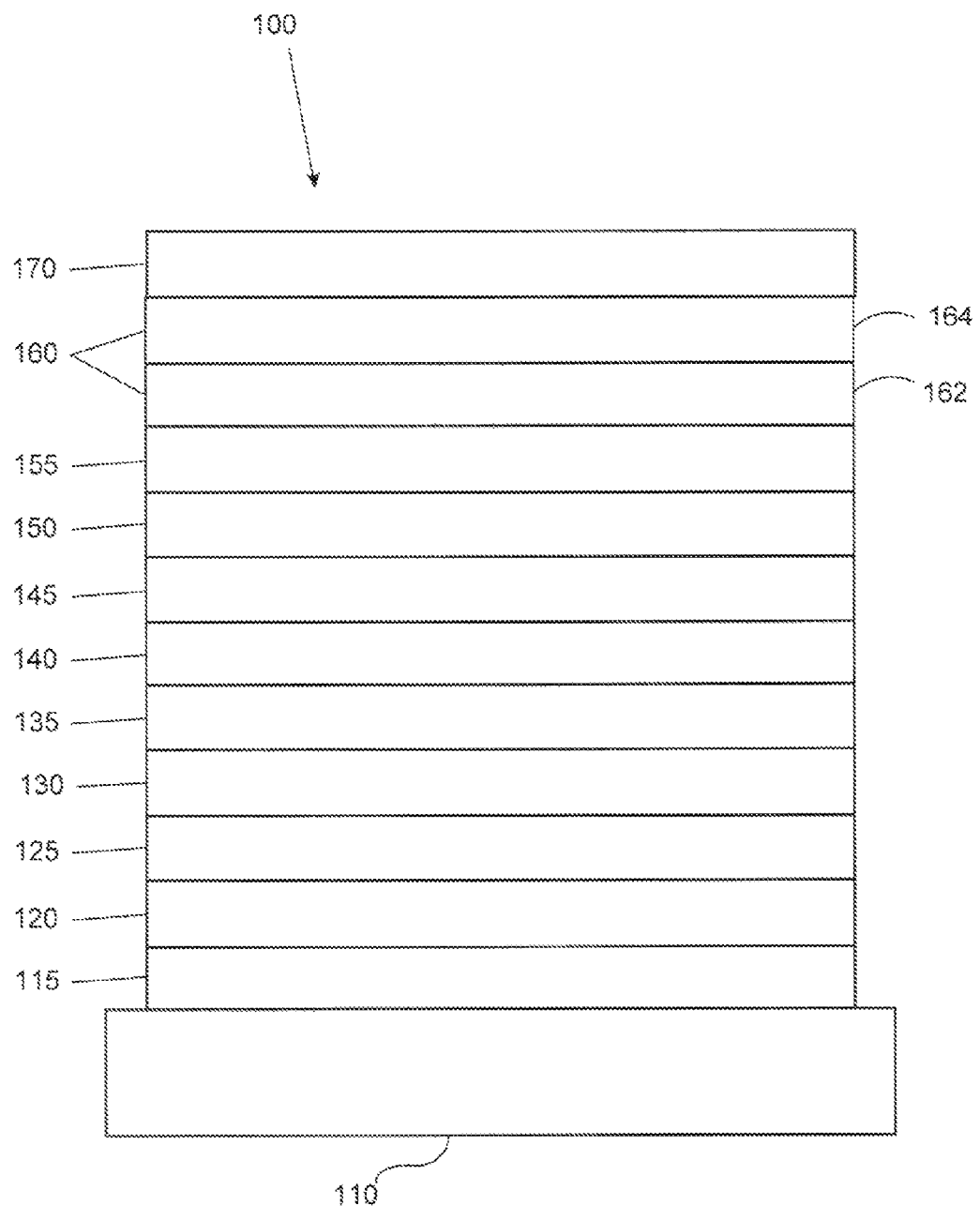
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
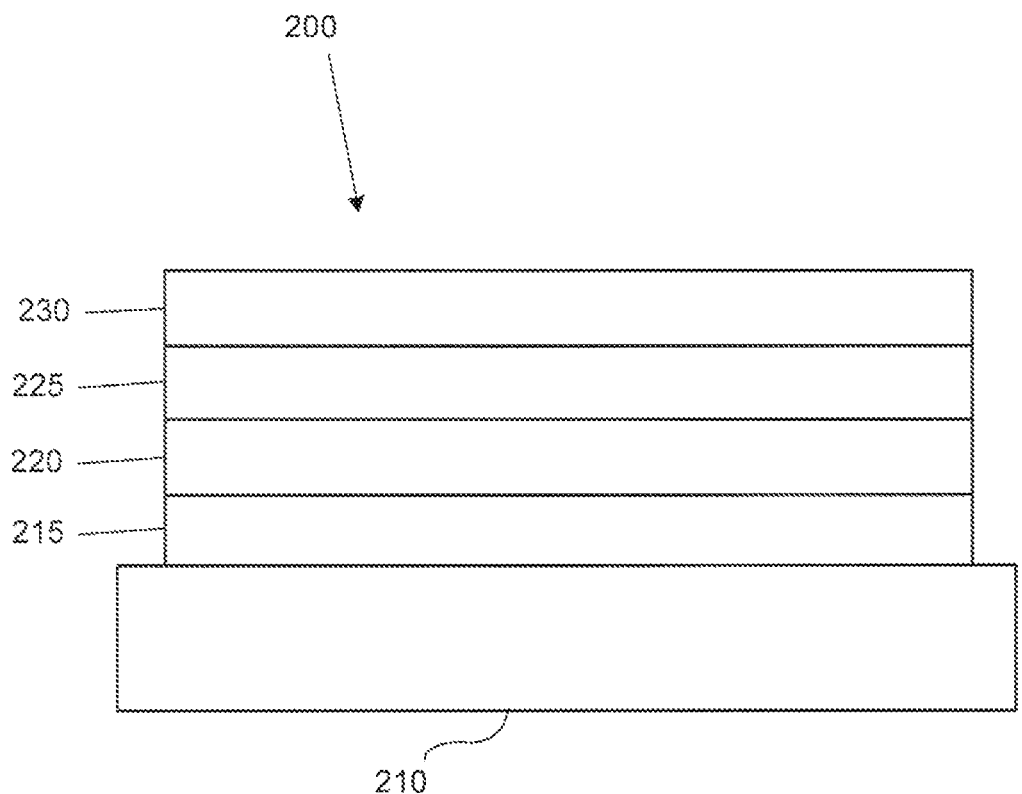
FIG. 2 shows an inverted organic light emitting device that does not have a separate electron transport layer.
Figure 3:
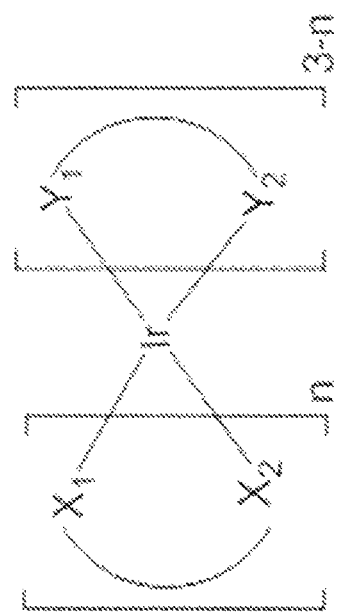
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution proccessability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, alkylaryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^4$ is monosubstituted, then one $R^4$ must be other than H. Similarly, where $R^4$ is disubstituted, the two of $R^4$ must be other than H. Similarly, where $R^4$ is unsubstituted $R^4$ is hydrogen for all available positions.

According to an embodiment, heteroleptic iridium complexes containing carbazole-imidazole-carbene ligands are provided. Metal carbene complexes have been developed as deep-blue emitters in phosphorescent OLEDs. However, devices based on these metal carbene complexes suffer from poor stability. This device instability is attributable to a number of possible factors, such as high sublimation temperature, slow triplet exciton decay, and unbalanced electron/hole fluxes in the device, etc. In this invention, carbene ligands are combined with other ligands to form metal complexes that modulate the HOMO/LUMO energy levels, emission spectra and charge transport properties, while promoting radiative decay of triplet excitons. These properties are further fine-tuned by introducing carbazole group attached to the imidazole-carbene moiety. Through this molecular design strategy, it is possible to integrate all desired merits of different ligands in one molecule. The device is also carefully designed so that it contains high triplet host, HTL, and/or HBL that will not quench the deep blue emitters.

The heteroleptic iridium complexes containing carbazole-imidazole-carbene ligands, which may be advantageously used in OLEDs, have the structure of Formula I:

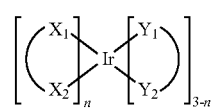

Formula I wherein n=1 or 2;
wherein $X_1$-$X_2$ is a bidentate ligand having Formula II:

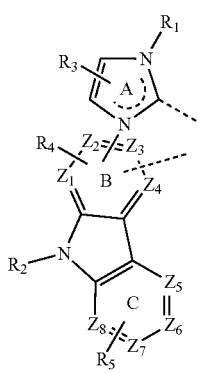

Formula II wherein each of $R_1$, $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_3$, $R_4$ and $R_5$ may represent mono, di, tri, tetra substitutions, or no substitution. Each of $R_3$, $R_4$ and $R_5$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and wherein two adjacent substituents are optionally joined to form into a ring. Each of $Z_1$, $Z_2$, $Z_3$, $Z_4$, $Z_6$, $Z_7$, $Z_8$ is independently selected from C, CH or N; ring A is connected to ring B through N—C bond; and $Y_1$-$Y_2$ is a different bidentate ligand other than $X_1$-$X_2$.

In some embodiments, $X_1$-$X_2$ can be selected from the group consisting of

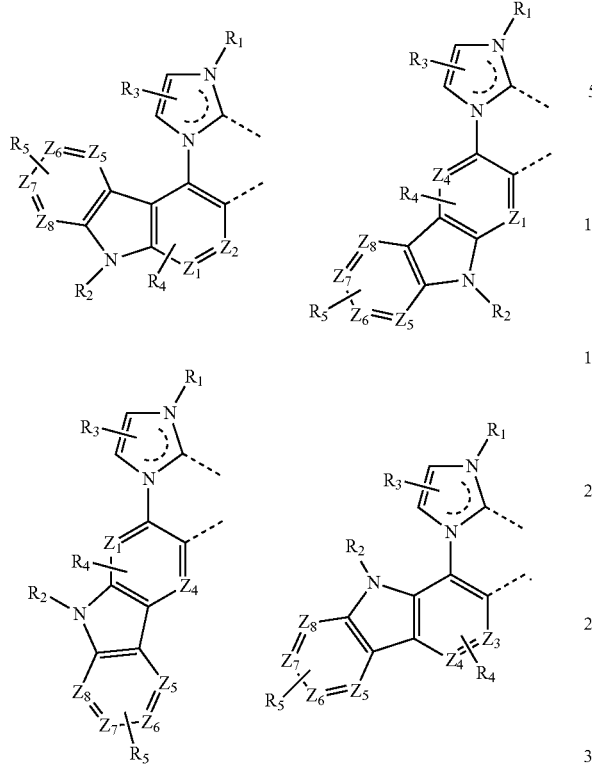

In some embodiments, $Y_1$-$Y_2$ can be selected from the group consisting of:

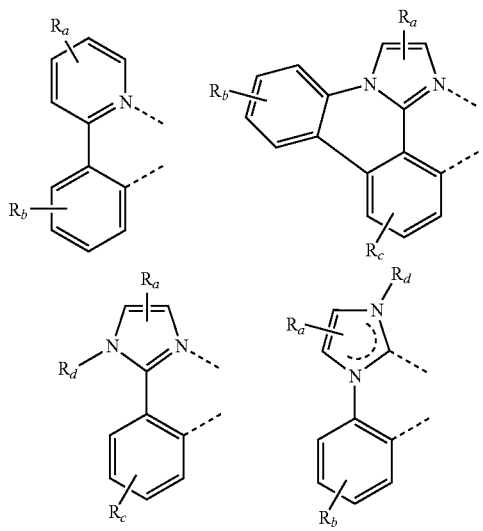

wherein $R_a$, $R_b$, $R_c$, $R_d$ are selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein two adjacent substituents are optionally joined to form into a ring.

More specifically, in some embodiments, $Y_1$-$Y_2$ can be:

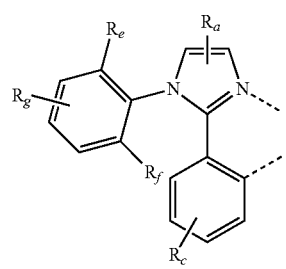

wherein $R_g$ represents mono, di, tri, substitutions or no substitution. $R_e$, $R_f$, and $R_g$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R_e$ and $R_f$ is not hydrogen or deuterium.

In some embodiments, neither $R_e$ nor $R_f$ is hydrogen or deuterium. In some embodiments, ring B is coupled to the central Ir atom of Formula I through an Ir—C bond. In other words, the one of $Z_1$-$Z_4$ that is coupled to the central Ir atom is C.

In some embodiments, $R_1$ can be selected from the group consisting of deuterium, linear, branched or cyclic $C_1$-$C_8$ alkyl, aryl, alkylaryl, heteroaryl and combinations thereof. More specifically, in some embodiments, $R_1$ can be selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof; and wherein each group is optionally partially or fully deuterated.

Examples of $C_1$-$C_8$ alkyl that can be useful in the formulas herein, include methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof; wherein each group is optionally partially or fully deuterated. Examples of aryl or alkyaryl that can be useful in the formulas herein include phenyl, 2,6-dimethylphenyl, 2,4,6-trimethylphenyl, 2,6-diisopropylphenyl, and combinations thereof; and wherein each group is optionally partially or fully deuterated.

In some embodiments, $R_2$ can be selected from the group consisting of deuterium, linear, branched or cyclic $C_1$-$C_8$ alkyl, aryl, alkylaryl, heteroaryl and combinations thereof. More specifically, in some embodiments, $R_2$ can be selected from the group consisting of substituted or unsubstituted benzene and pyridine. The benzene or pyridine can be substituted by deuterium, $C_1$-$C_8$ alkyl, $C_6$-$C_{30}$ aryl, $C_5$-$C_{30}$ heteroaryl, and combinations thereof.

In some embodiments, $R_3$ is disubstituted and $R_3$ comprises two adjacent substituents joined to form an aryl, alkylaryl or heteroaryl ring. In some more specific embodiments, ring A can have the structure selected from the group consisting of:

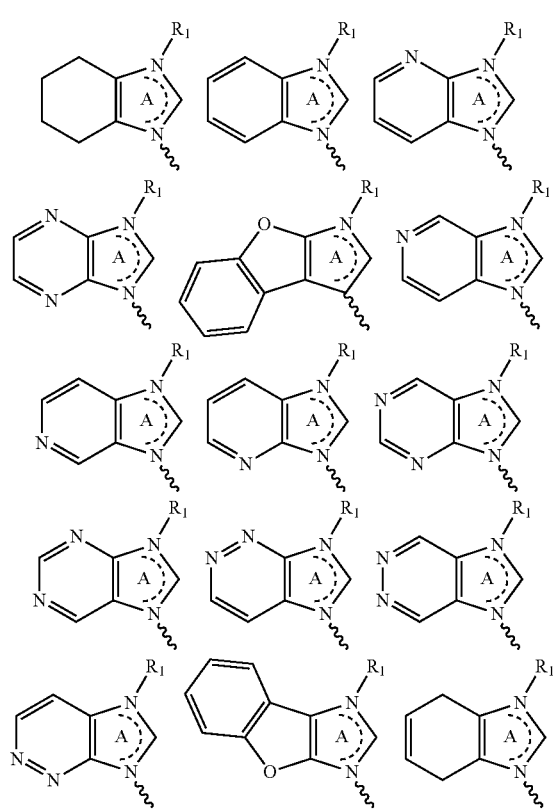

In some embodiments, $R_4$ can be mono, di or trisubstituted, and at least one $R_4$ is selected from the group consisting of $C_1$-$C_8$-alkyl.

In some embodiments, $R_5$ is disubstituted, and $R_5$ comprises two adjacent substituents joined to form an aryl, alkylaryl or heteroaryl ring.

In some embodiments, at least one of $Z_1$-$Z_4$ is N, or at least two of $Z_1$-$Z_4$ are N, or at least three of $Z_1$-$Z_4$ are N. In some embodiment, one of $Z_1$-$Z_4$ is N. In other embodiments, two of $Z_1$-$Z_4$ are N, or three of $Z_1$-$Z_4$ are N. In still other embodiments, each of $Z_1$-$Z_4$ is N.

In some embodiments, at least one of $Z_5$-$Z_8$ is N, or at least two of $Z_5$-$Z_8$ are N, or at least three of $Z_5$-$Z_8$ are N. In some embodiment, one of $Z_5$-$Z_8$ is N. In other embodiments, two of $Z_5$-$Z_8$ are N, or three of $Z_5$-$Z_8$ are N. In still other embodiments, each of $Z_5$-$Z_8$ is N.

In some more specific embodiments, $X_1$-$X_2$ can be selected from the group consisting of:

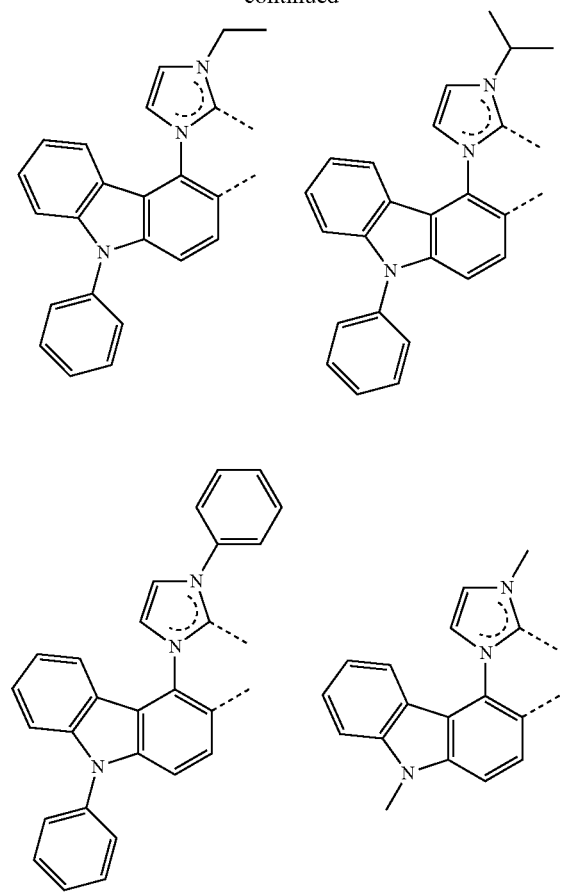

-continued

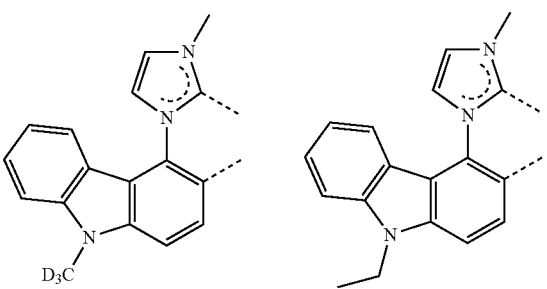

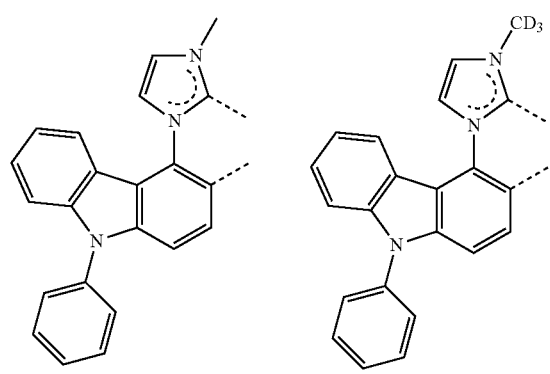

13
-continued
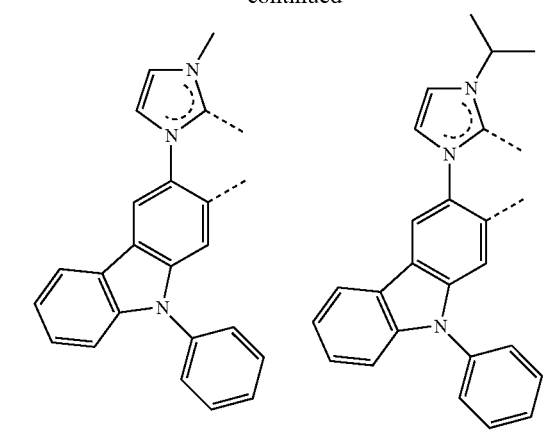
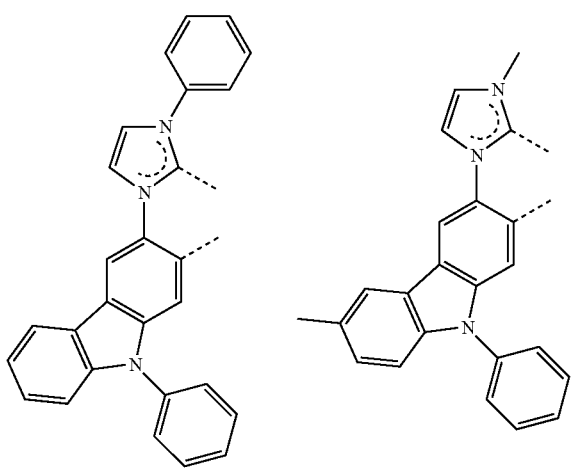
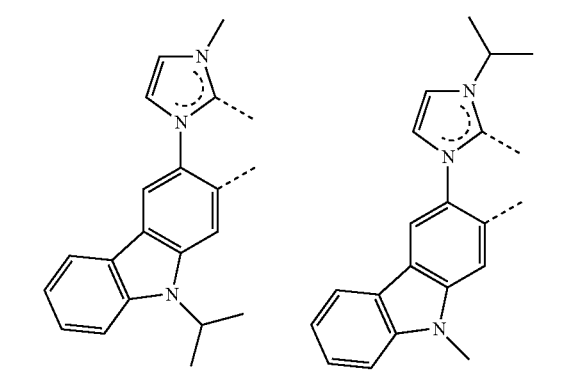
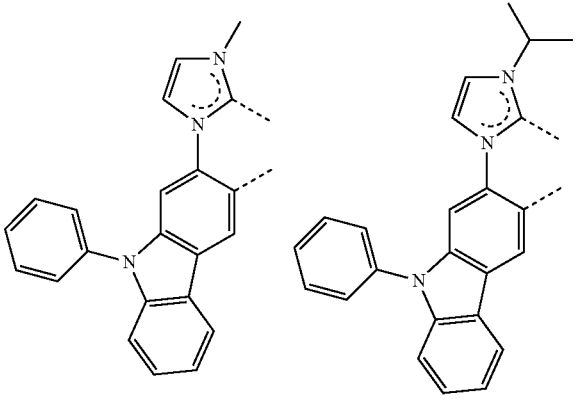
14
-continued
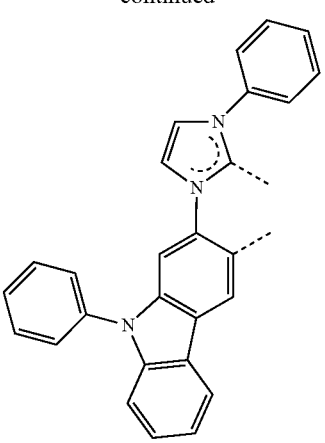
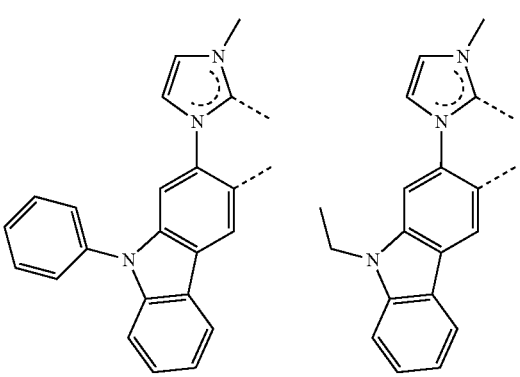
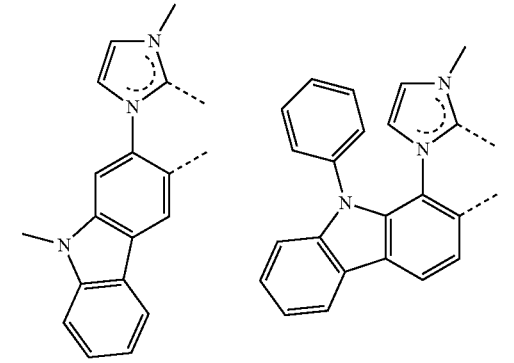
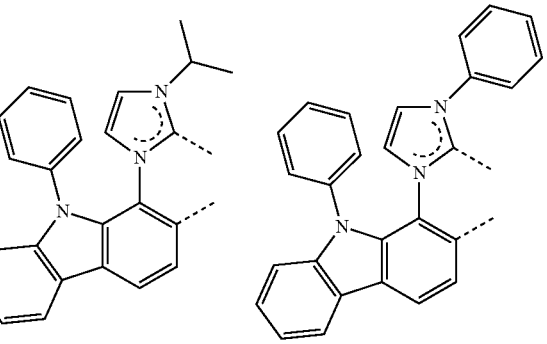

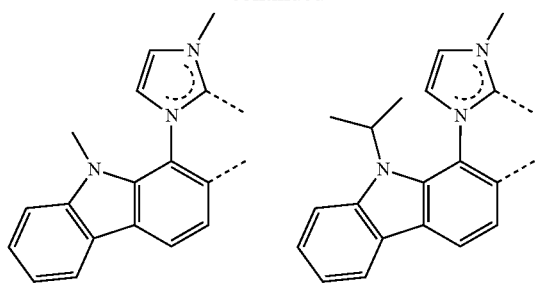
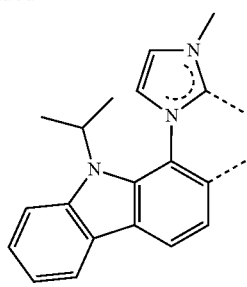
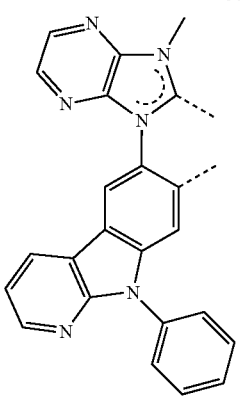
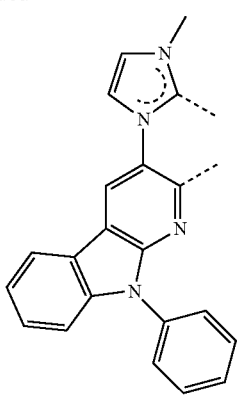
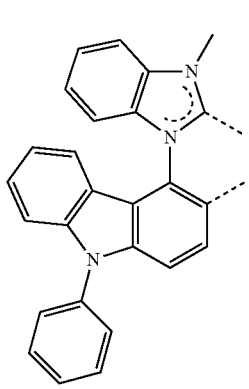
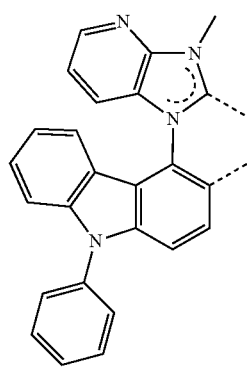
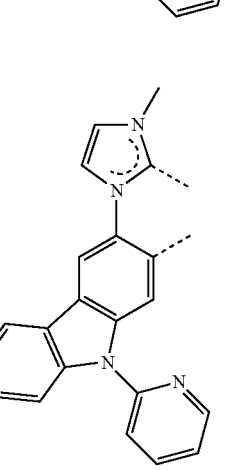
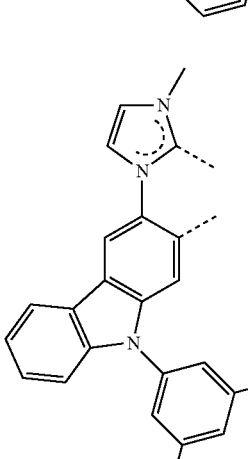
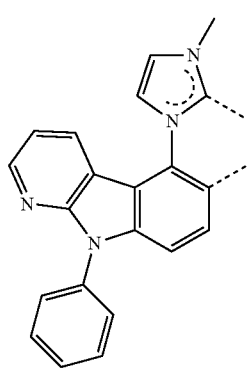
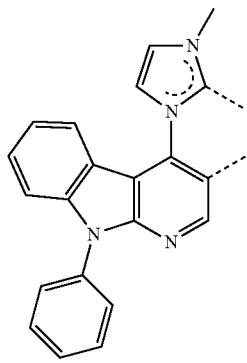
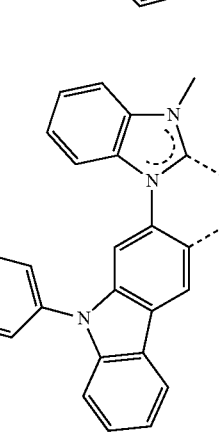
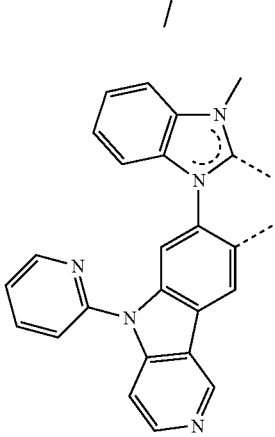
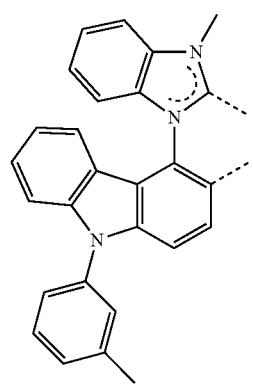
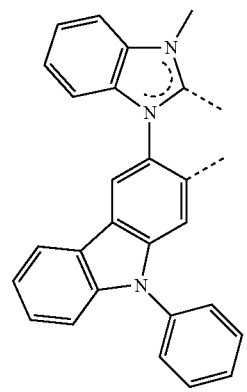
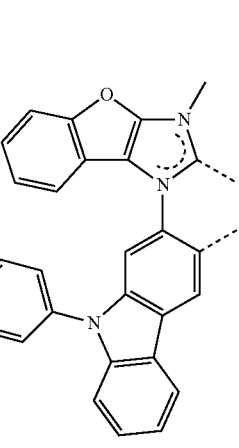
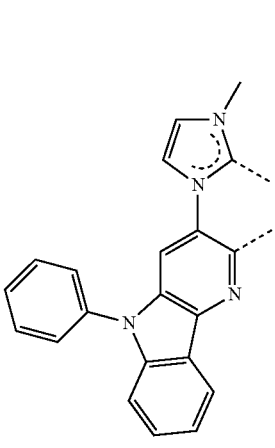

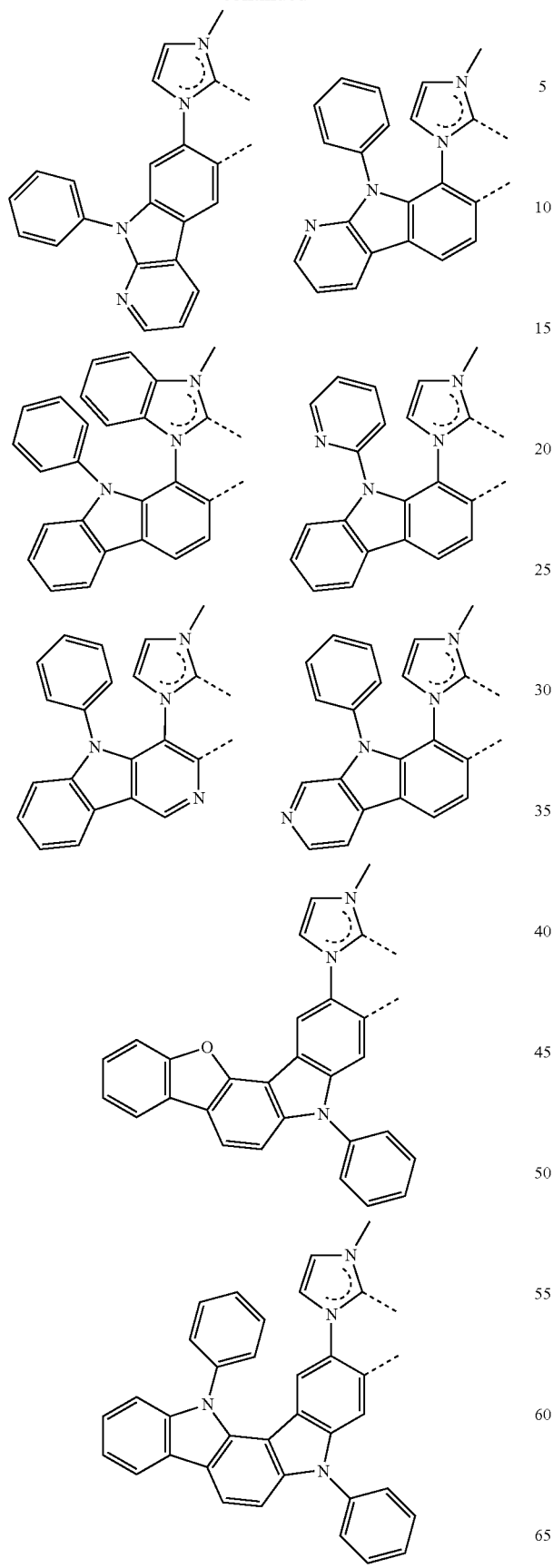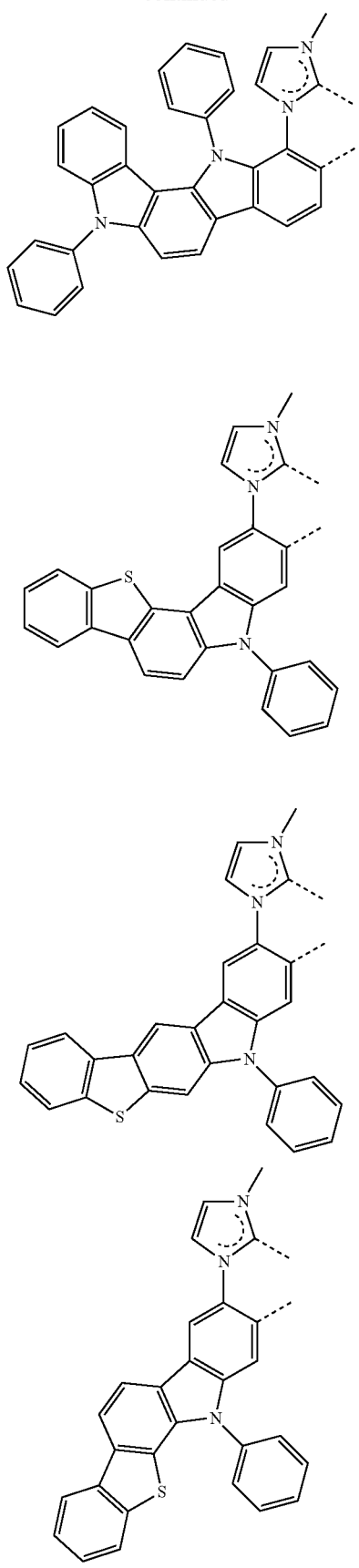

-continued
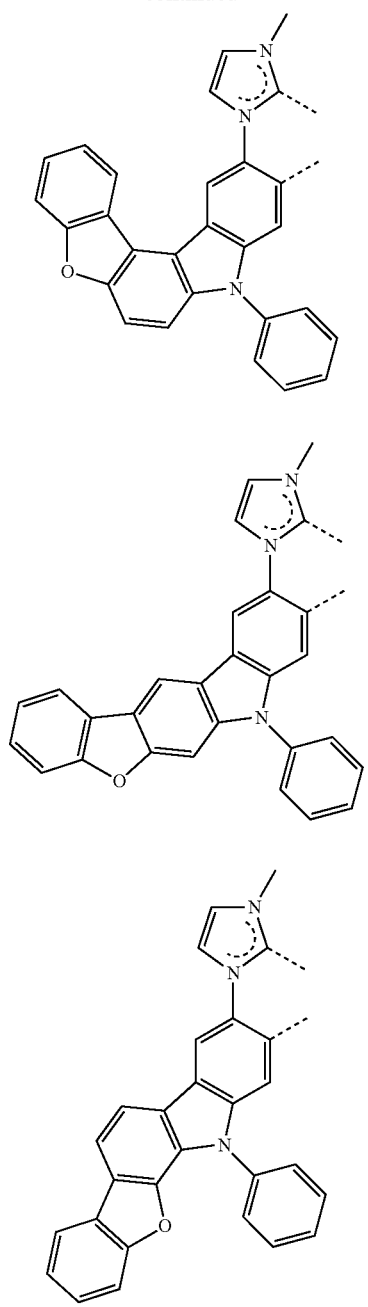
In other more specific embodiments, $Y_1$-$Y_2$ can be selected from the following:
-continued
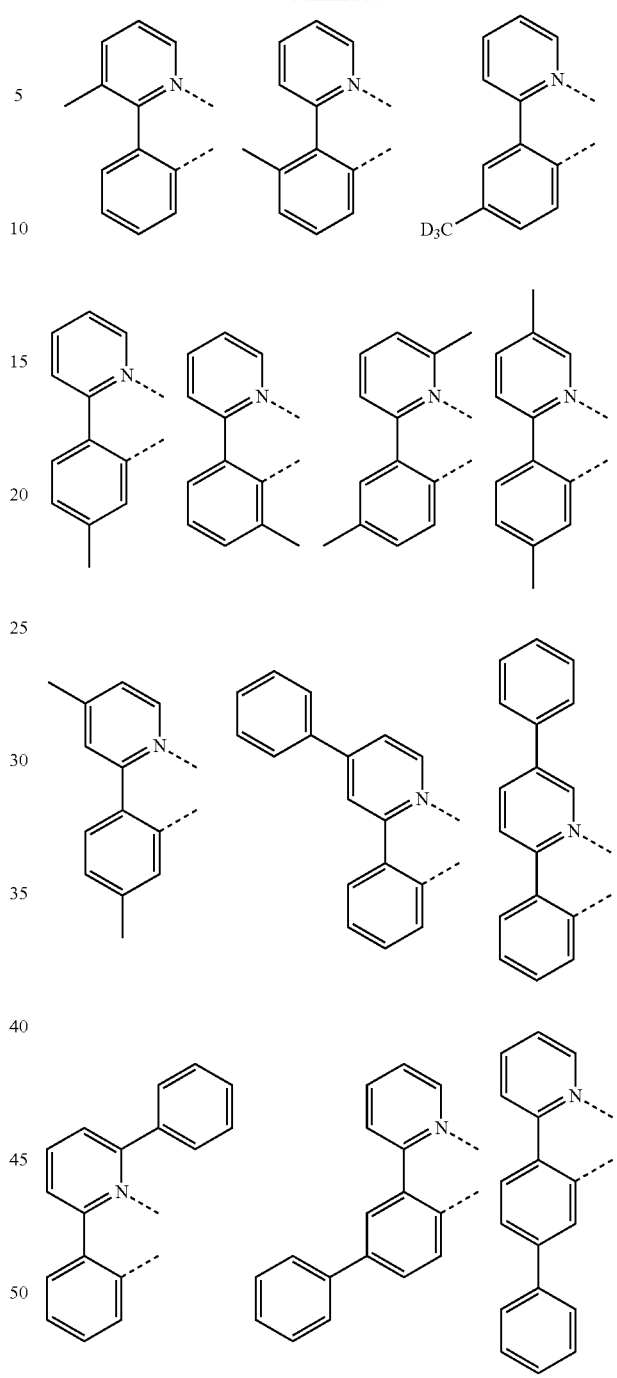
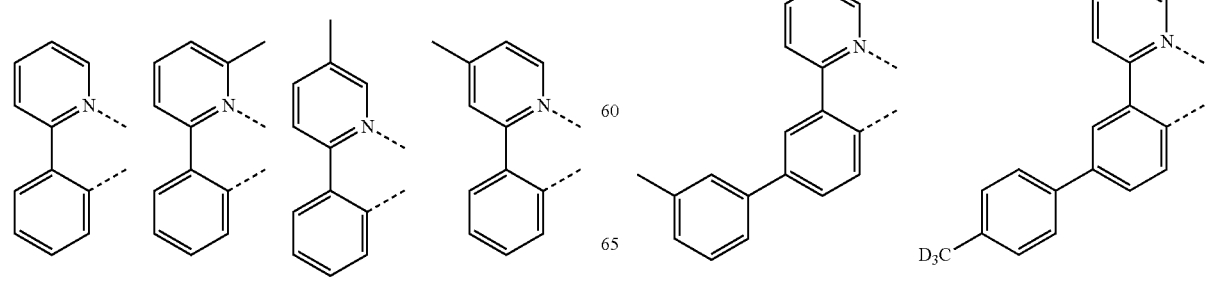

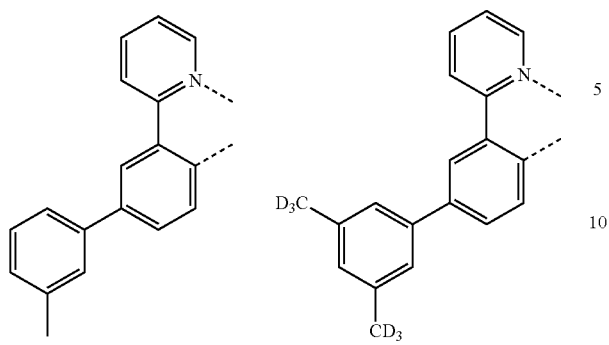
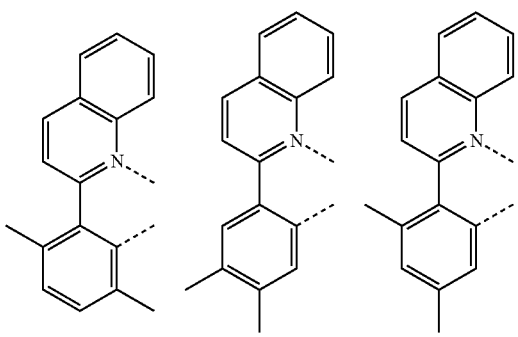

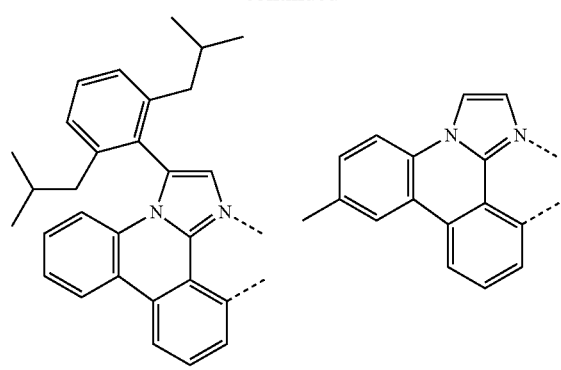
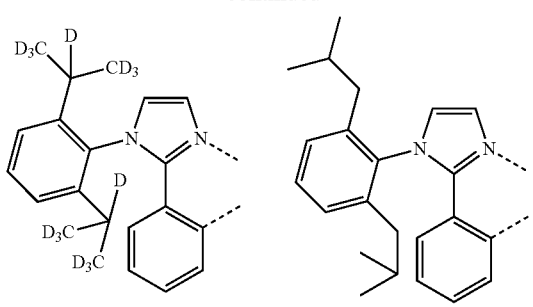
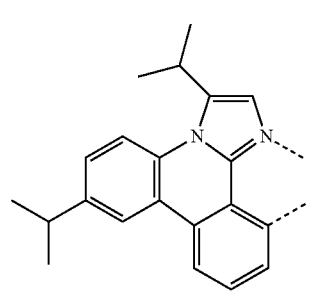
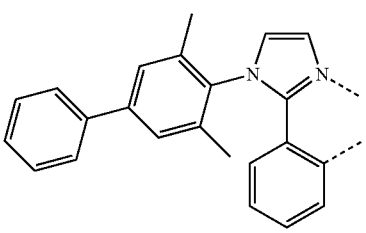
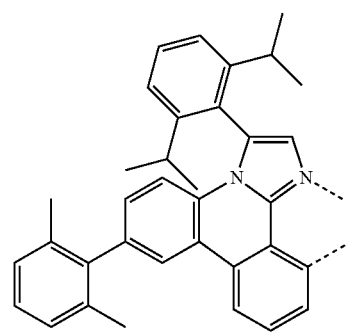
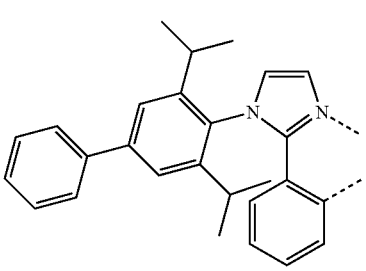
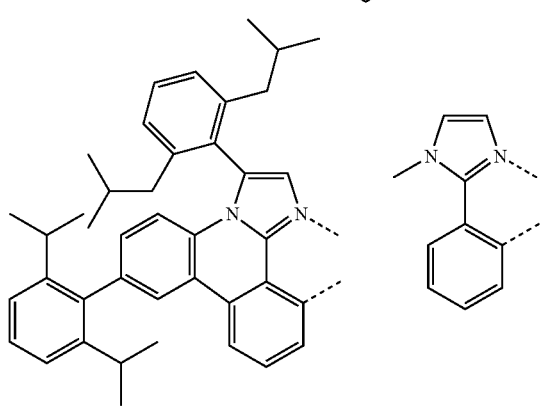
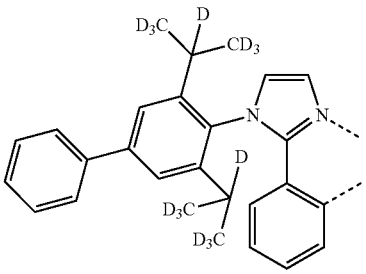
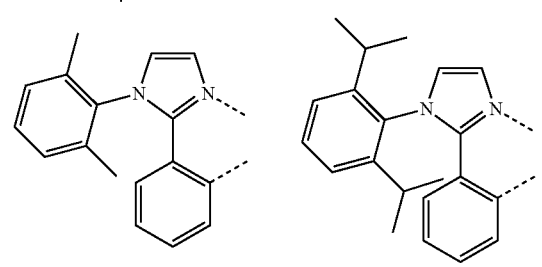
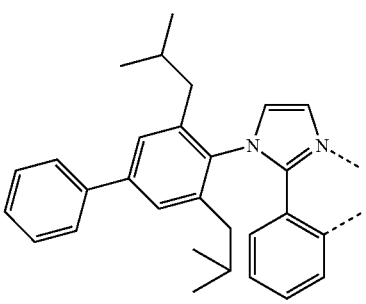
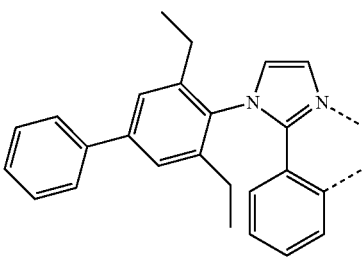

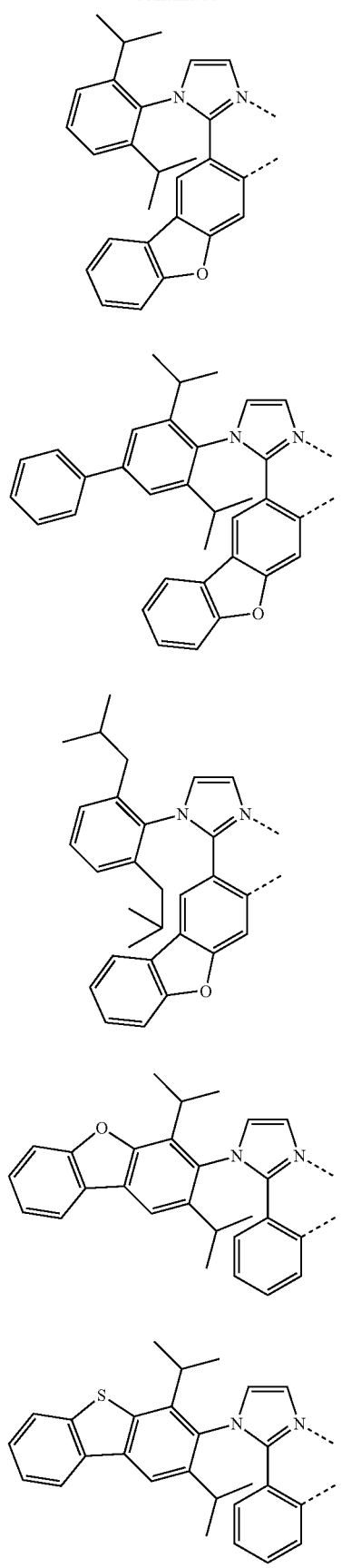
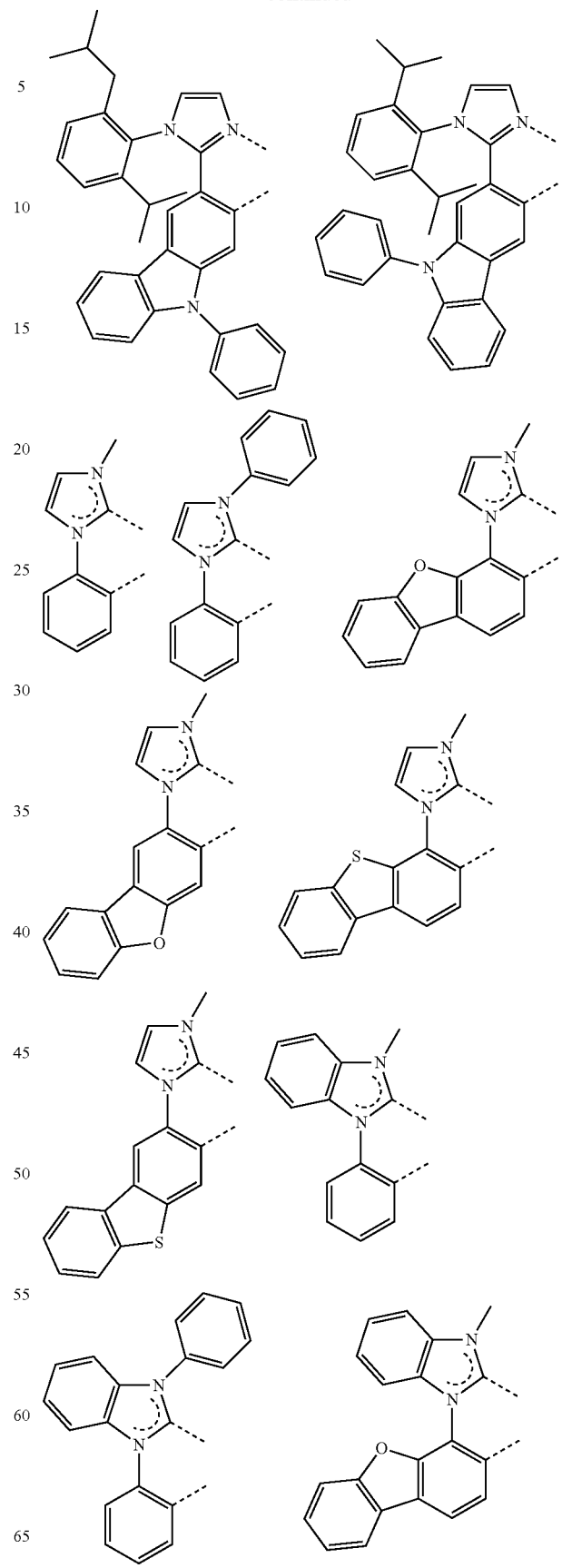

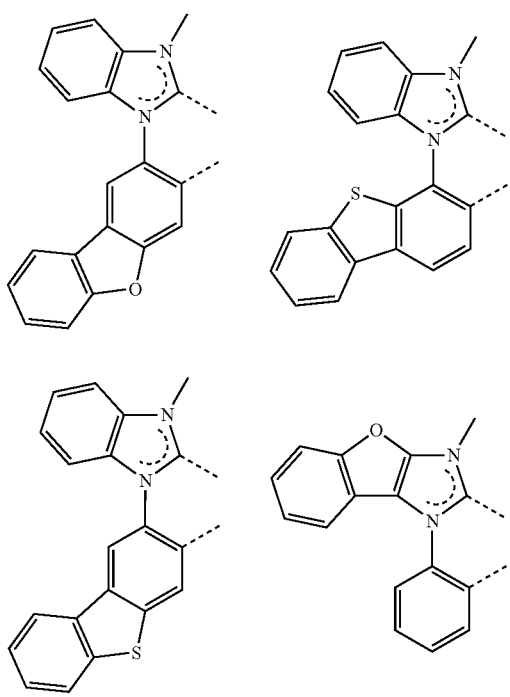
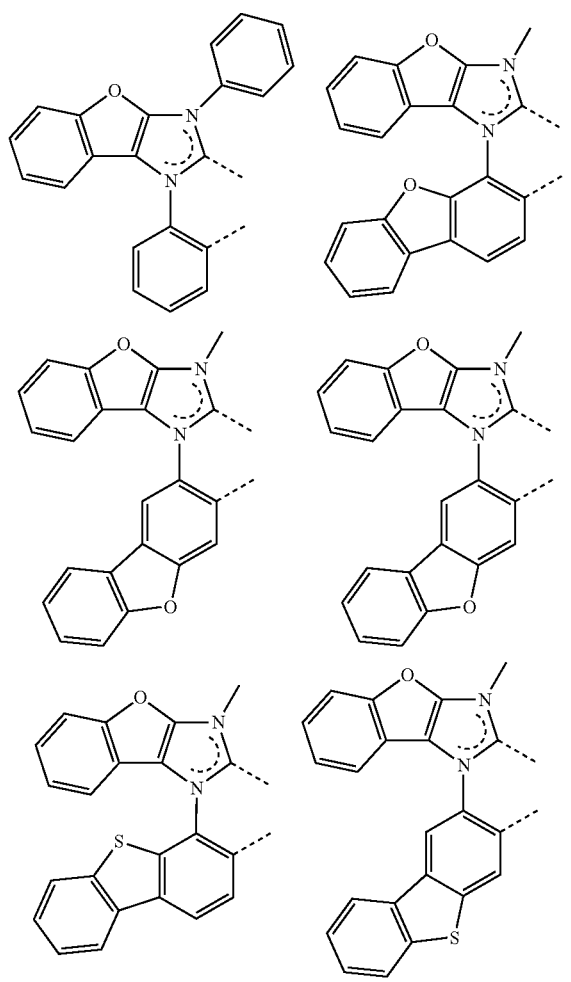
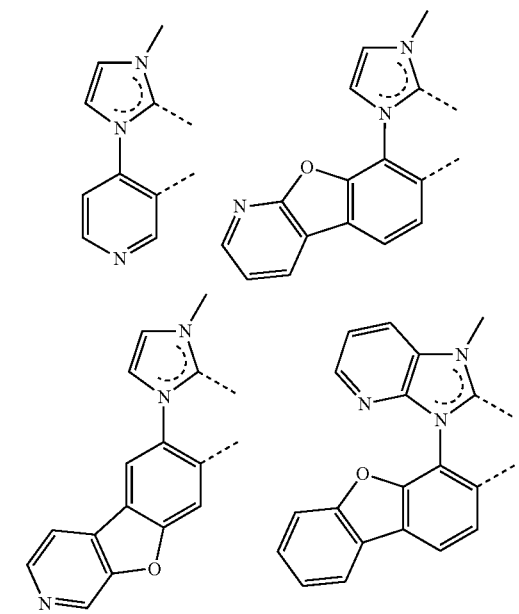
In some embodiments, n can be 1, while n can be 2 in other embodiments.
In some embodiments, the compound can be selected from the group consisting of:
Compound 1
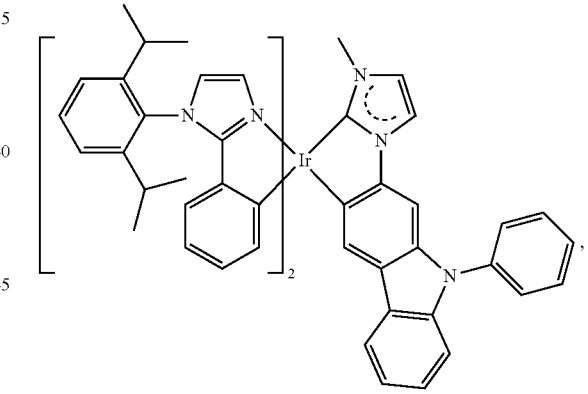
Compound 2
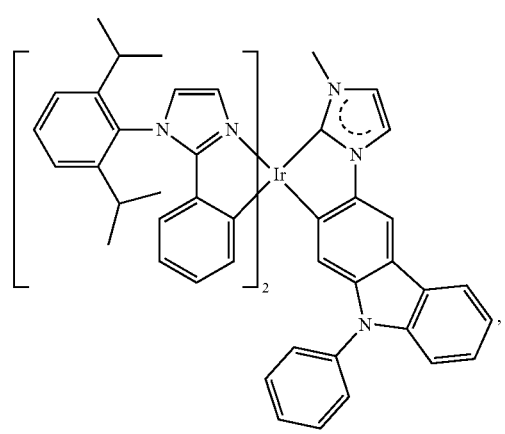

-continued
Compound 3
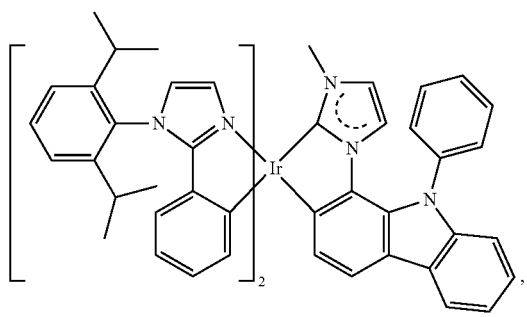
Compound 4
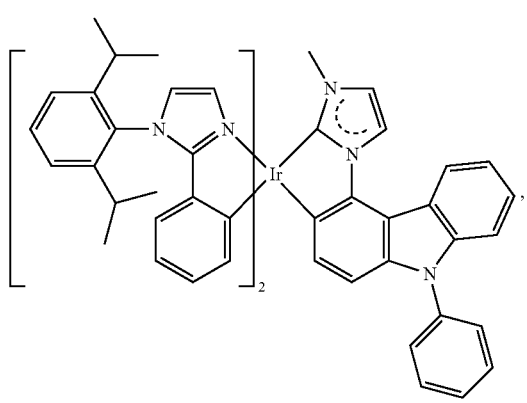
Compound 5
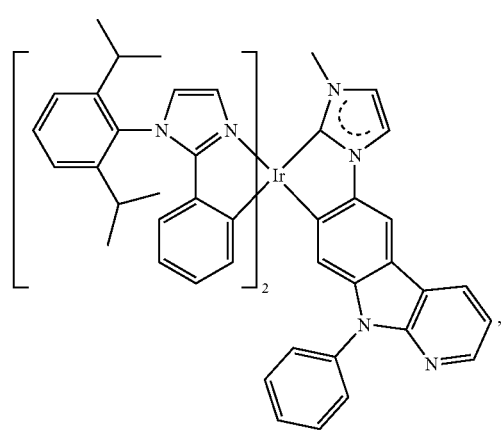
Compound 6
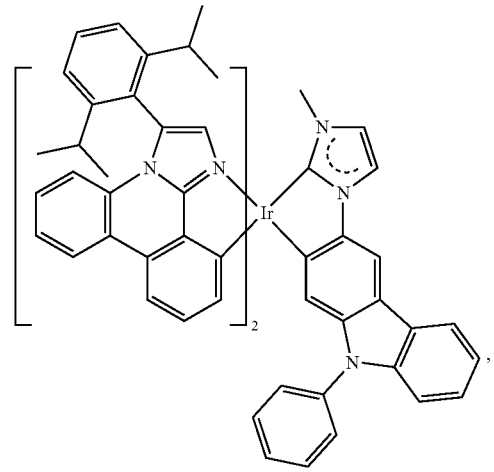
Compound 7
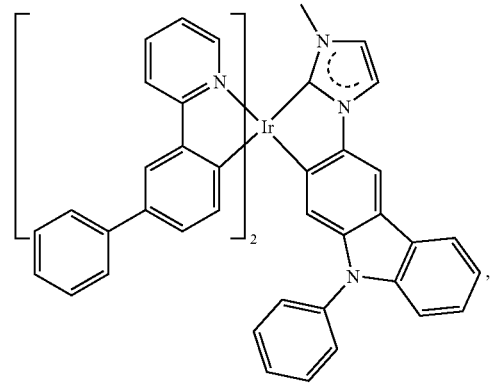
Compound 8
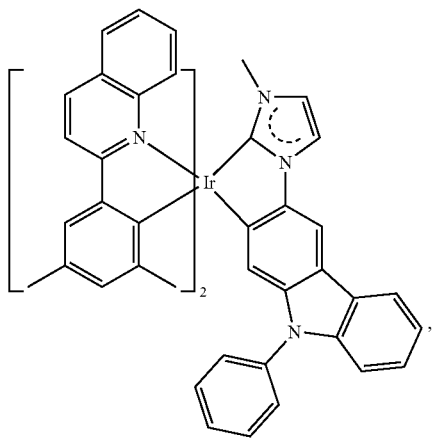

Compound 9
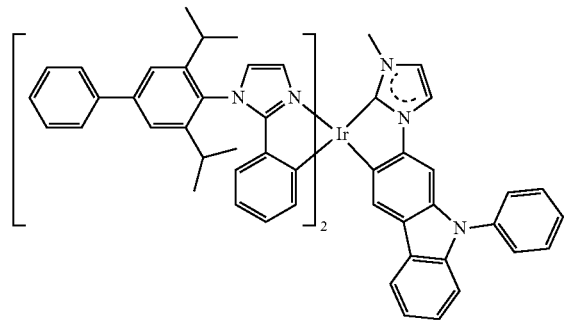
Compound 13
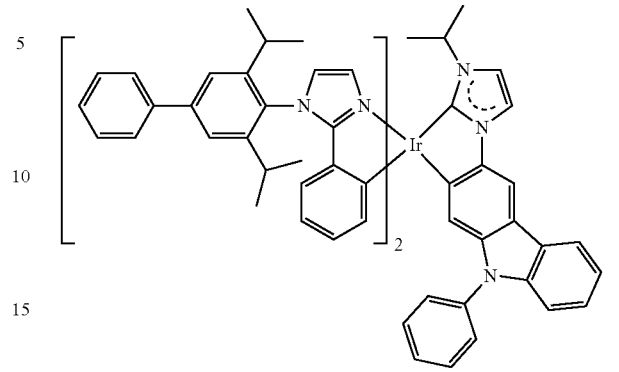
Compound 10
Compound 14
Compound 11
Compound 15
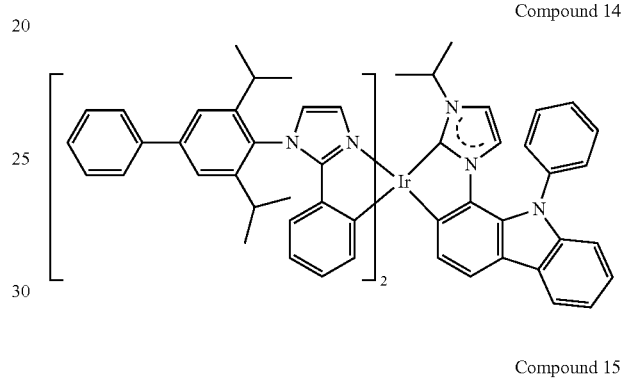
Compound 12
Compound 16
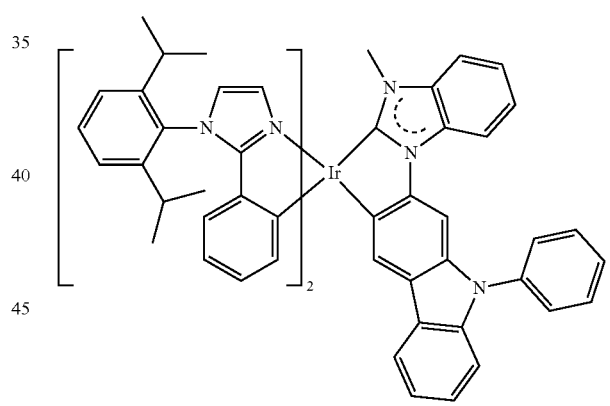
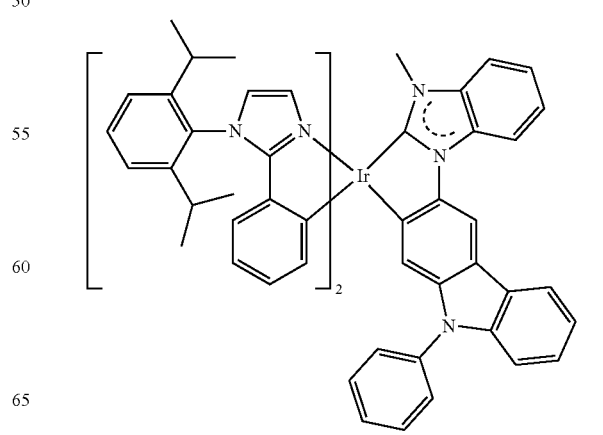

Compound 17
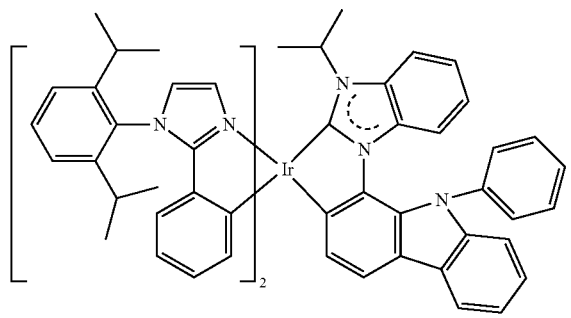
Compound 18
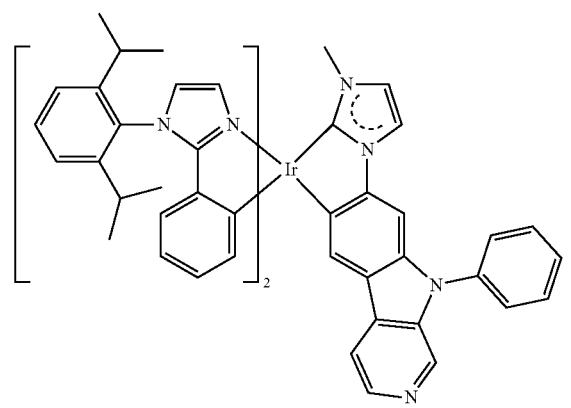
Compound 19
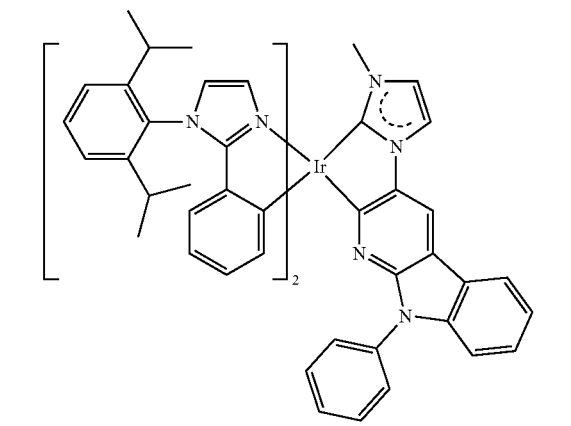
Compound 20
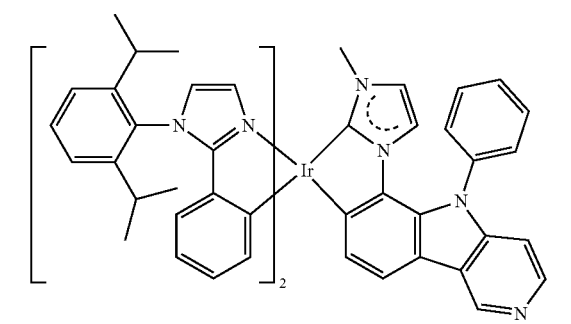
Compound 21
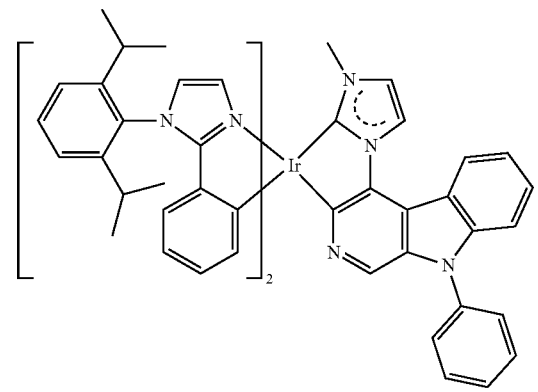
Compound 22
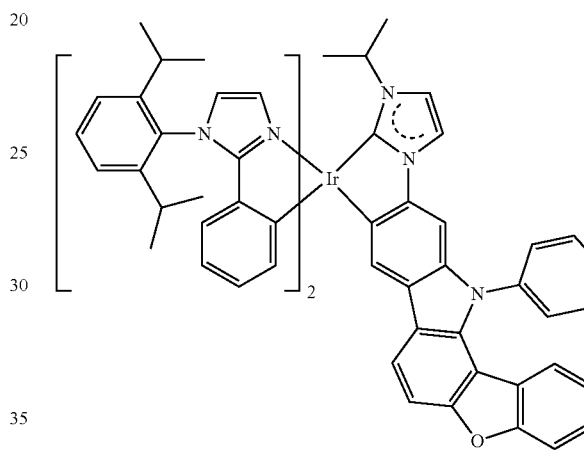
Compound 23
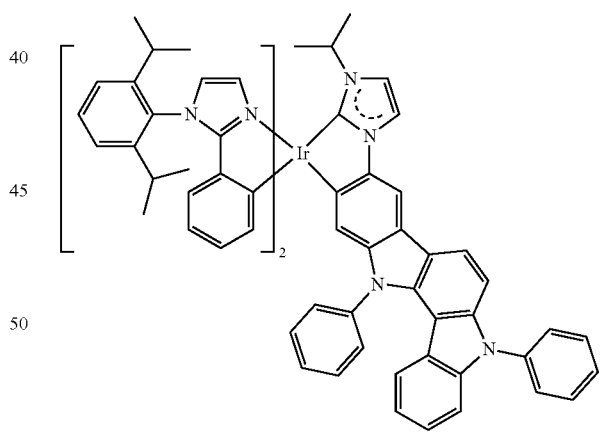
Compound 24
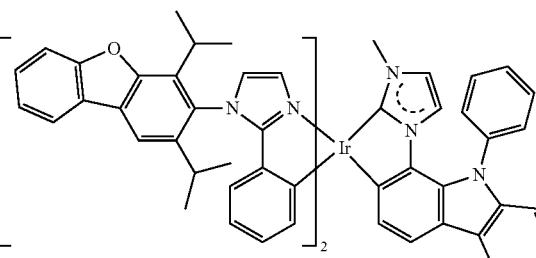

Compound 25
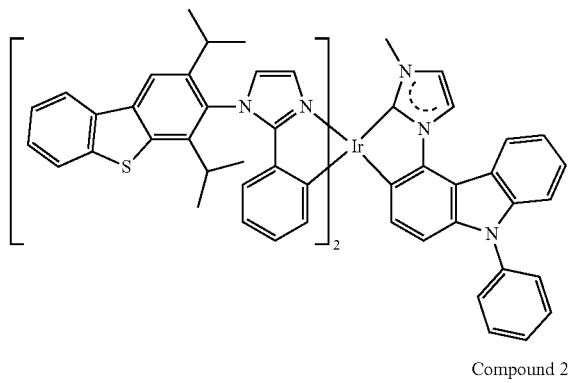
Compound 26
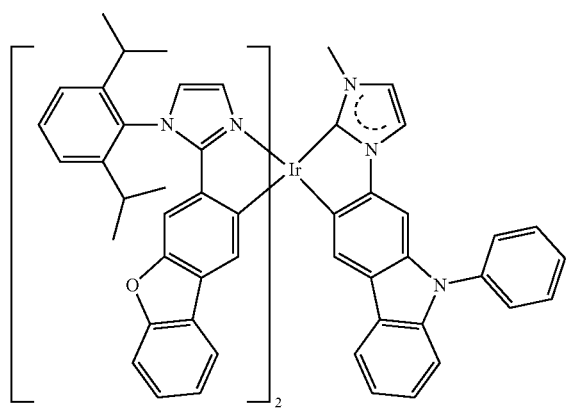
Compound 27
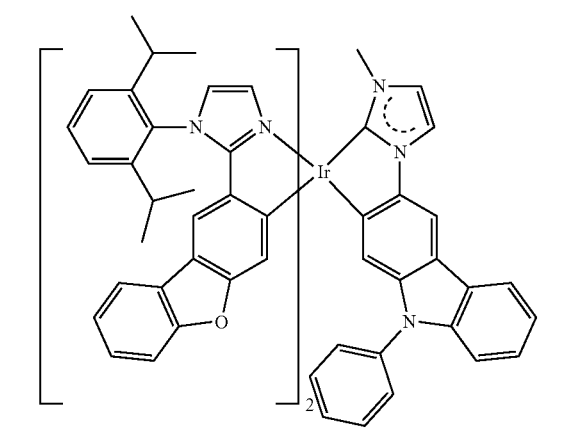
Compound 28
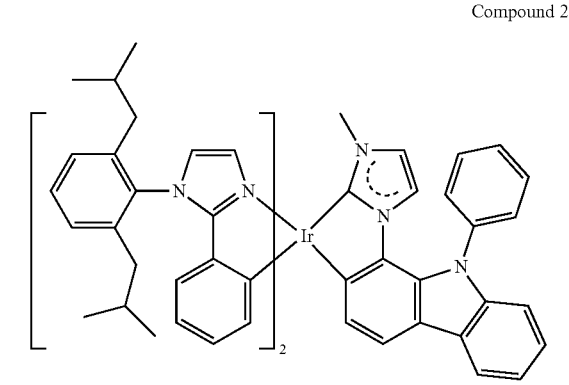
Compound 29
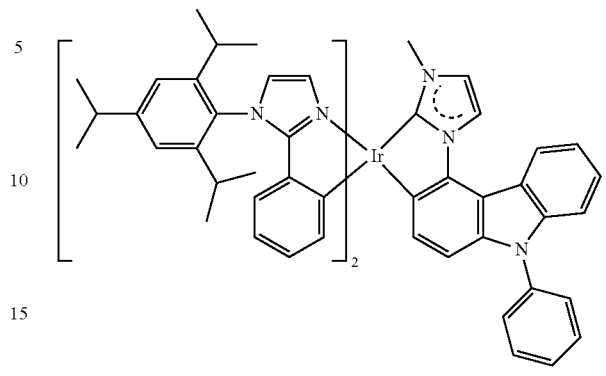
Compound 30
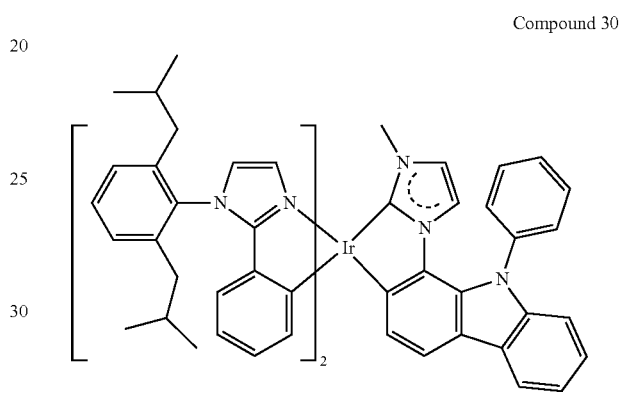
Compound 31
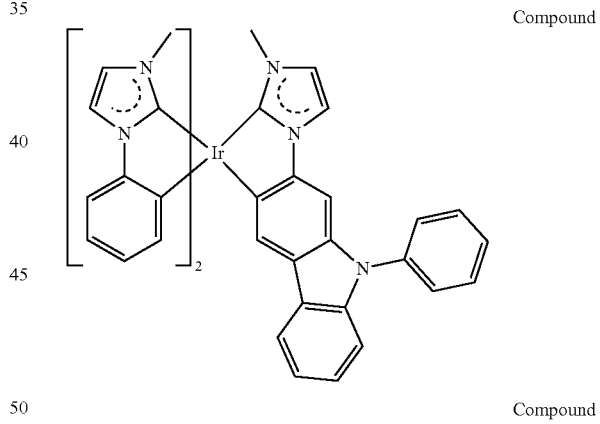
Compound 32
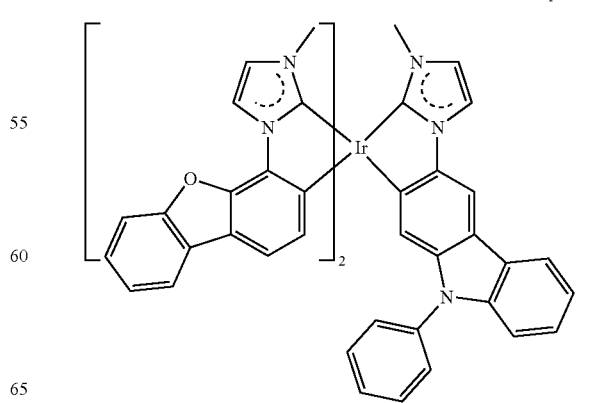

-continued
Compound 33
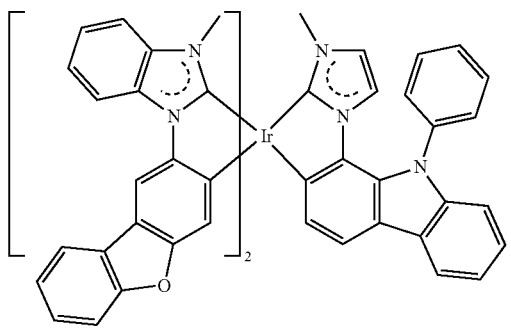
Compound 34
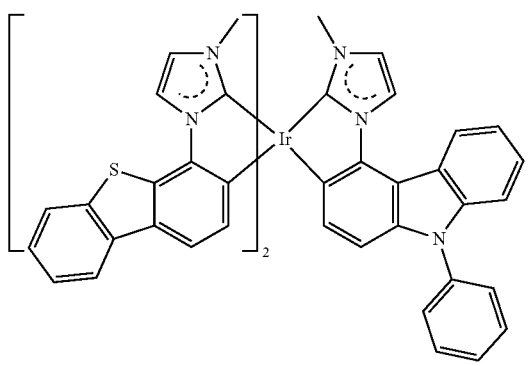
Compound 35
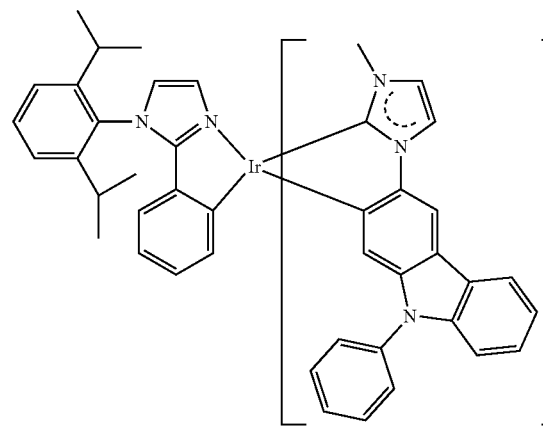
Compound 36
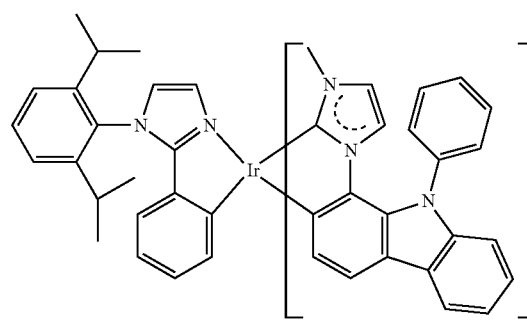
-continued
Compound 37
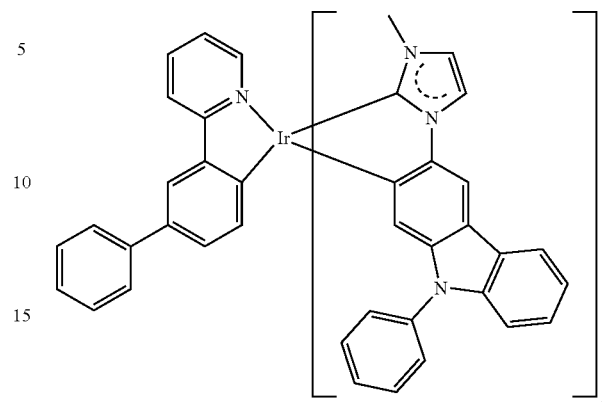
Compound 38
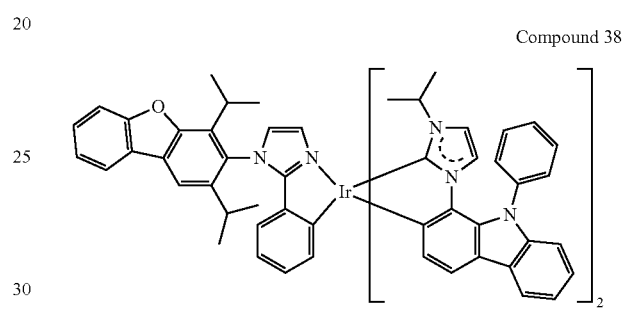
Compound 39
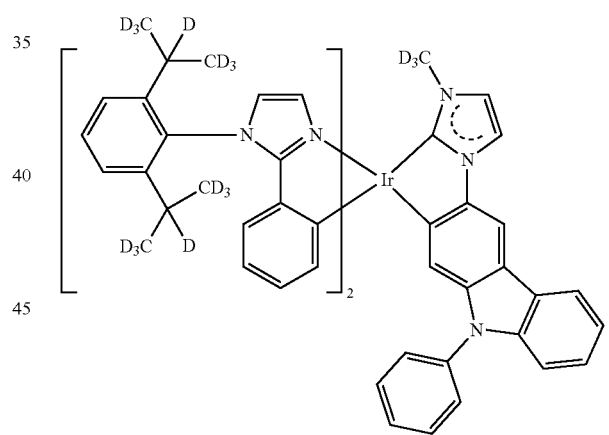
Compound 40
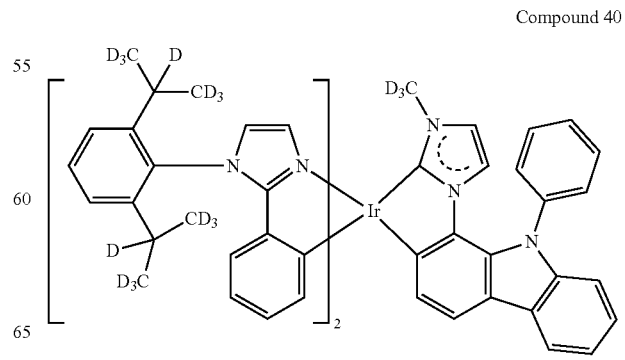

Compound 41
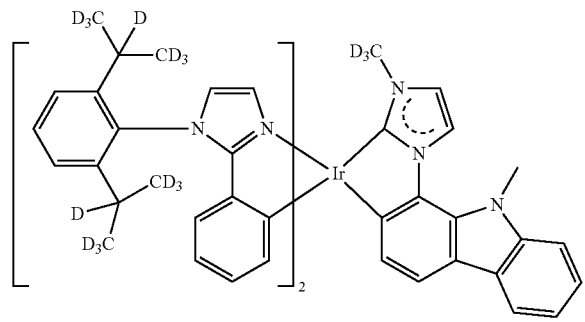

Compound 42
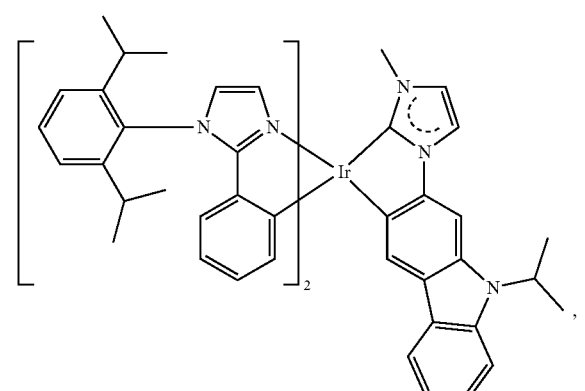

Compound 43

Compound 44
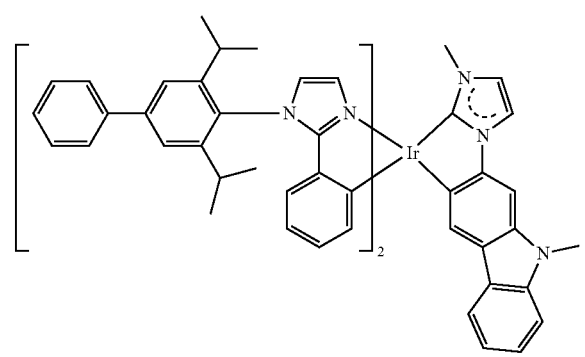

Compound 45
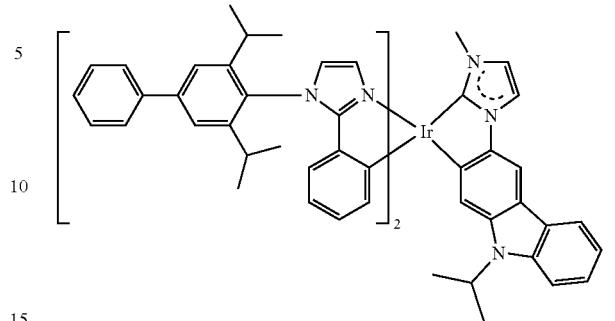

Compound 46

Compound 47
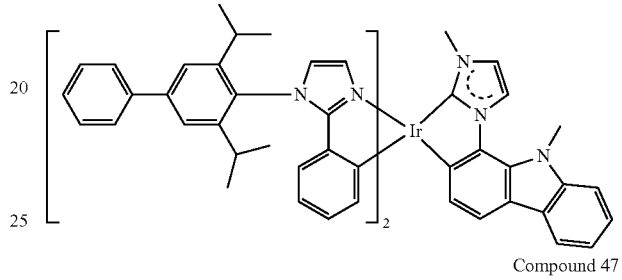

Compound 48
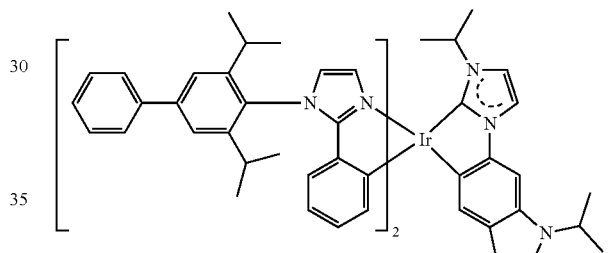

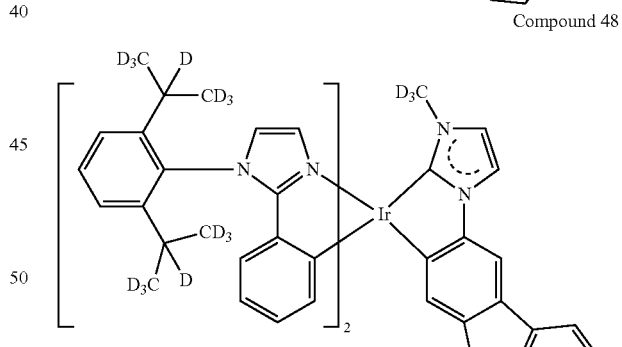

According to another aspect of the present disclosure, a first device is also provided. The first device includes a first organic light emitting device, that includes an anode, a cathode, and an organic layer disposed between the anode and the cathode. The organic layer can include a compound according to Formula I, and its variations as described herein.

The first device can be one or more of a consumer product, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiphene, dibenzofuran, dibenzoselenophene, azacarbazole, aza-dibenzothiophene, aza-dibenzofuran, and aza-dibenzoselenophene. The "aza" designation in the fragments described above, i.e., aza-dibenzofuran, aza-dibenzonethiophene, etc., means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein. The host can include a metal complex. The host can be a specific compound selected from the group consisting of:

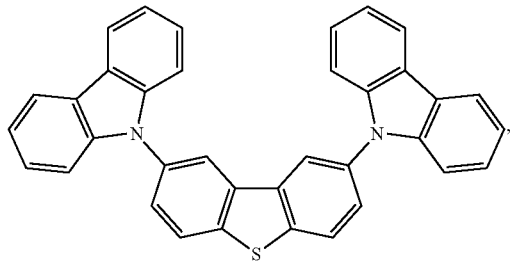

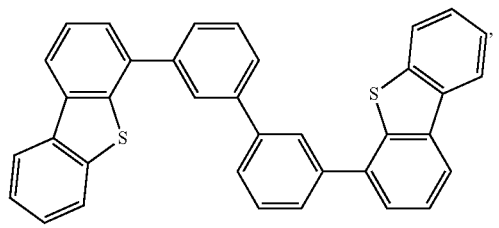

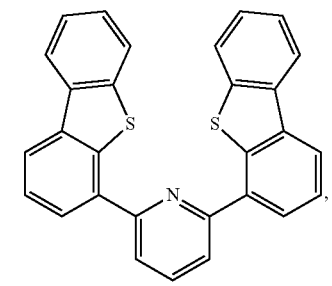

-continued

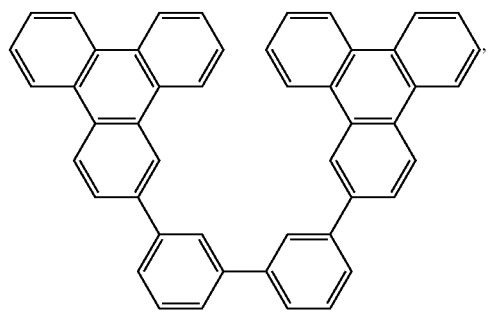

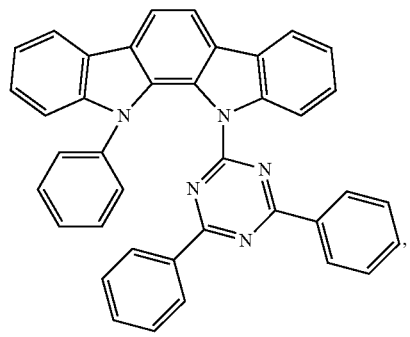

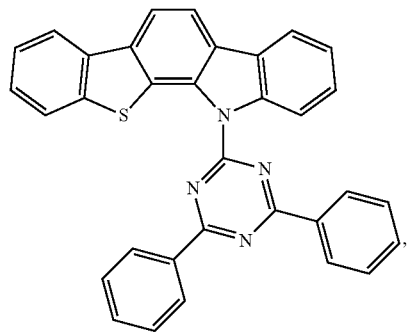

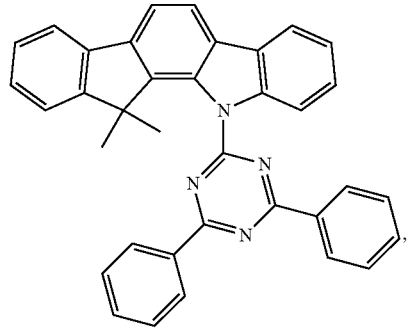

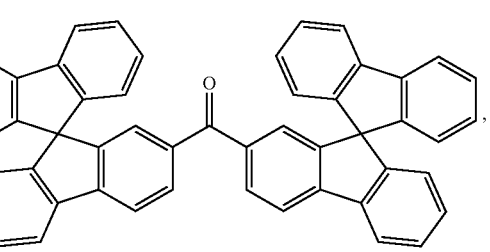

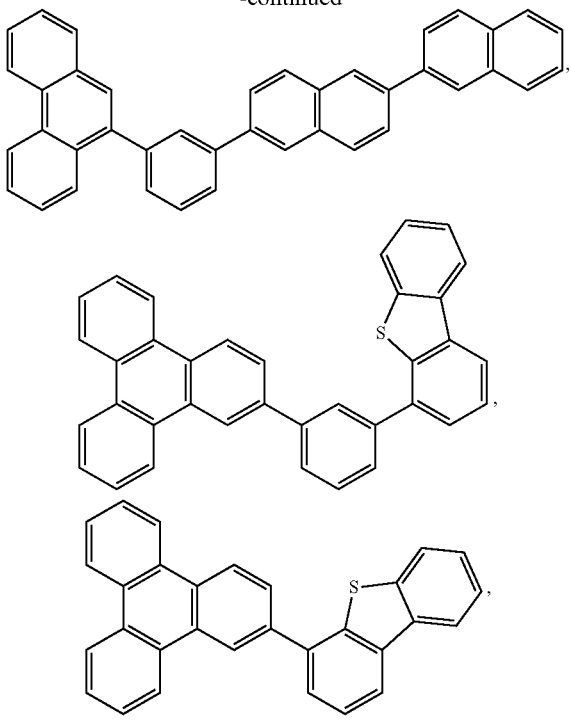

and combinations thereof.

In yet another aspect of the present disclosure, a formulation that includes a compound according to Formula I is described. The formulation can include one or more components selected from the group consisting of a solvent, a host, a hole injection material, hole transport material, an electron transport layer material (see below).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

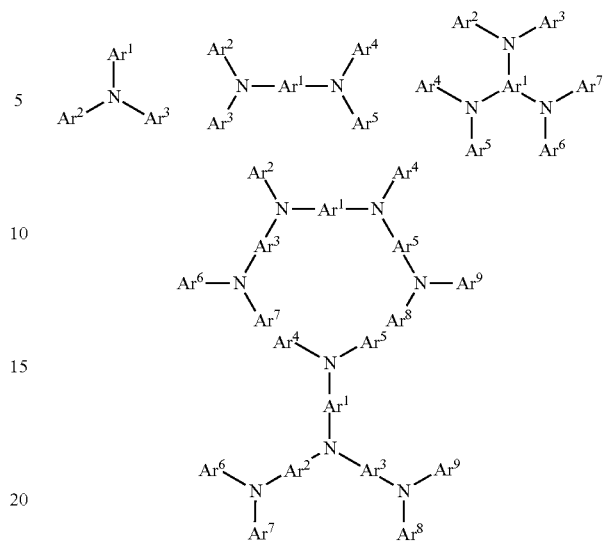

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

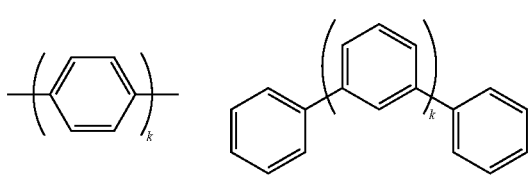

-continued

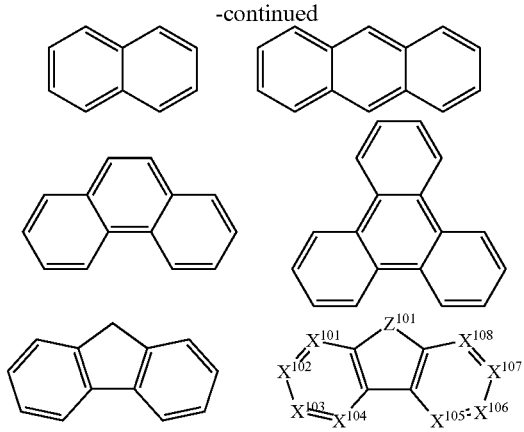

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

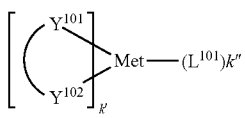

Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

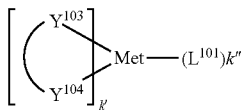

Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

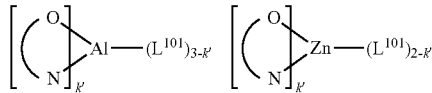

(O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

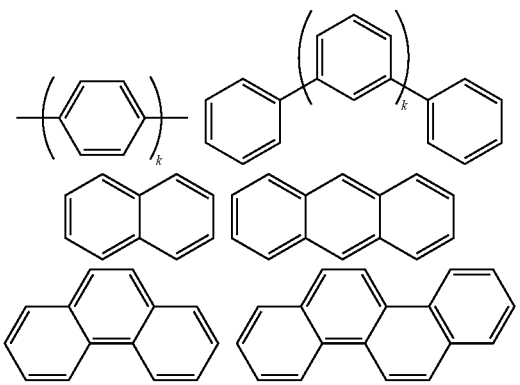

-continued

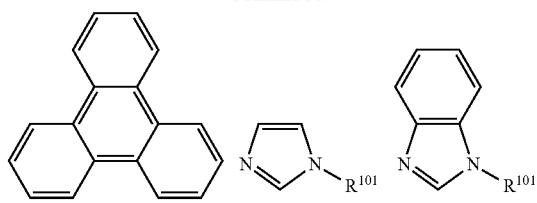

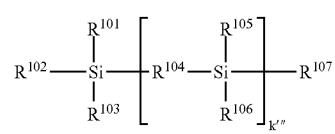

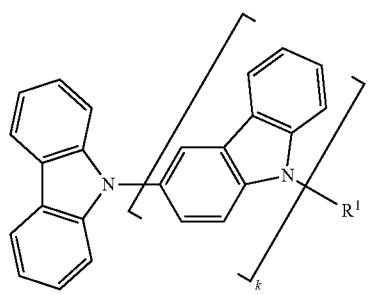

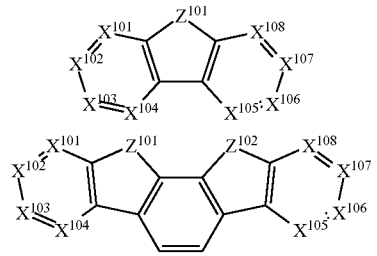

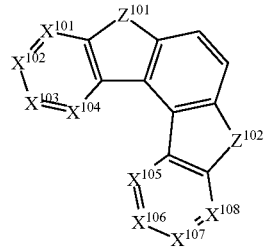

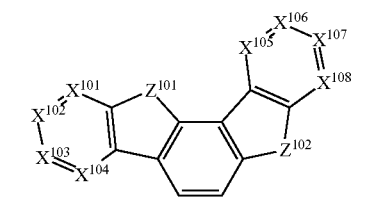

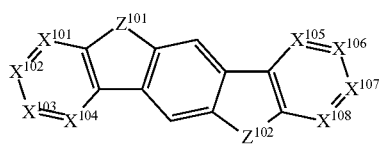

-continued

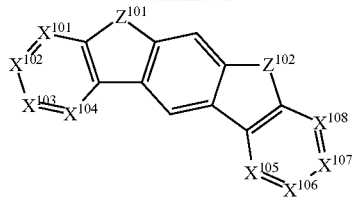

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20 or 1 to 20; k''' is an integer from 0 to 20.

$X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

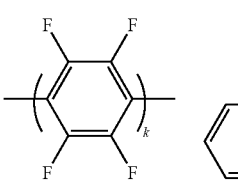
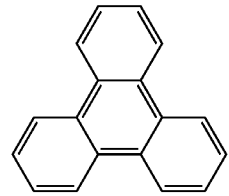
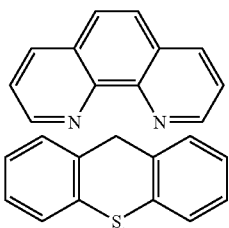
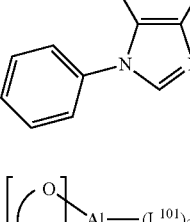
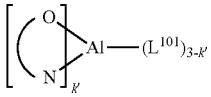

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

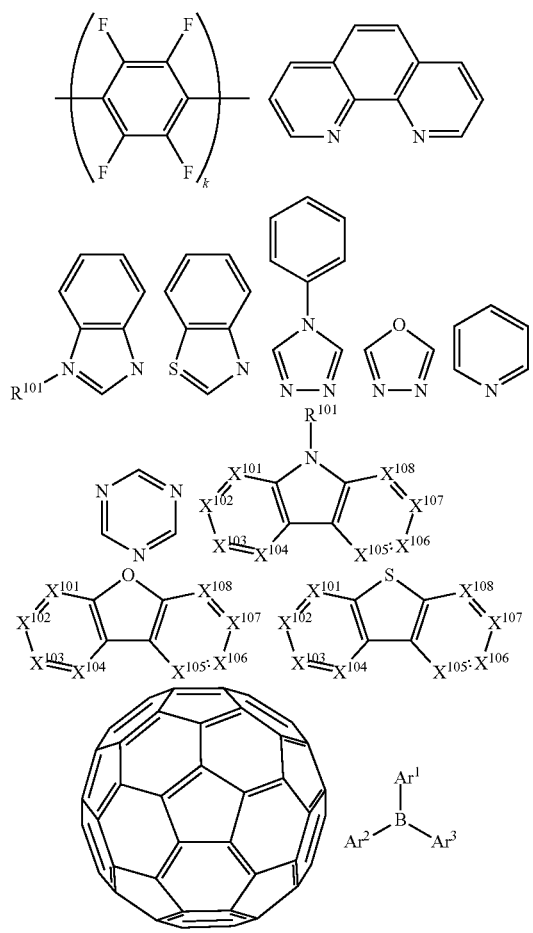

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

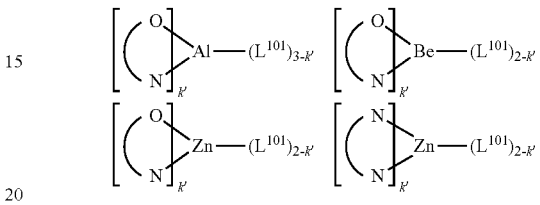

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| | Hole injection materials | |
| Phthalocyanine and porphryin compounds | | Appl. Phys. Lett. 69, 2160 (1996) |

TABLE 1-continued
| MATERIAL | EXAMPLES OF MATERIAL | PUBLICATIONS |
|---|---|---|
| Starburst triarylamines | 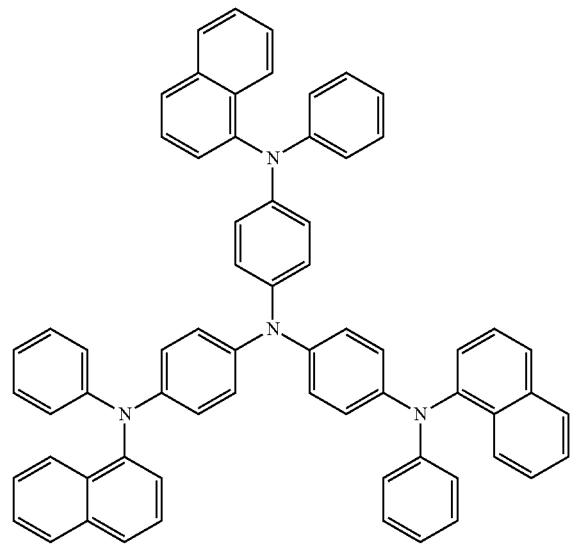 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | 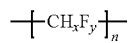 | Appl. Phys. Lett. 78, 673 (2001) |
| Conducting polymers (e.g., PEDOT:PSS, polyaniline, polypthiophene) | 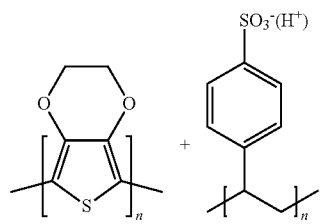 | Synth. Met. 87, 171 (1997) WO2007002683 |
| Phosphonic acid and sliane SAMs | 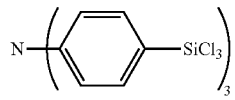 | US20030162053 |

TABLE 1-continued
| MATERIAL | EXAMPLES OF MATERIAL | PUBLICATIONS |
|---|---|---|
| Triarylamine or polythiophene polymers with conductivity dopants | 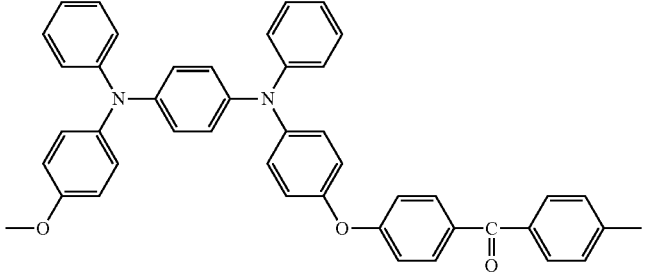 and 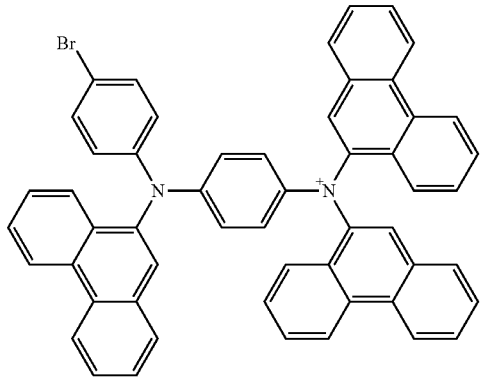 [SMILES: Brc1ccc(N(c2ccc(N(c3cc4ccccc4c4ccccc34)c3cc4ccccc4c4ccccc34)cc2)c2cc3ccccc3c3ccccc23)cc1] 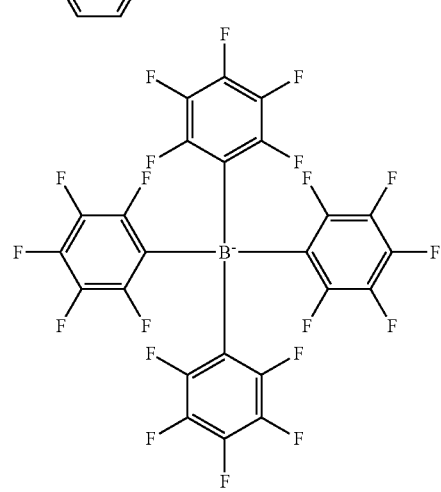 | EP1725079A1 |
| Organic compounds with conductive inorganic compounds, such as molybdenum and tungsten oxides | 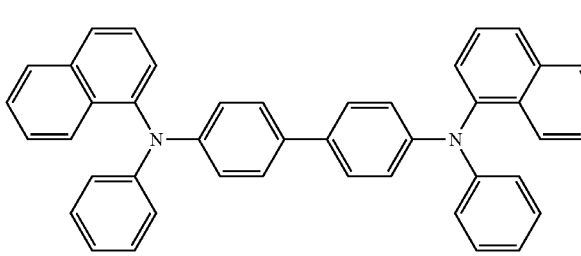 + $MoO_x$ | US20050123751 SID Symposium Digest, 37, 923 (2006) WO2009018009 |

TABLE 1-continued
| MATERIAL | EXAMPLES OF MATERIAL | PUBLICATIONS |
| --- | --- | --- |
| n-type semiconducting organic complexes | 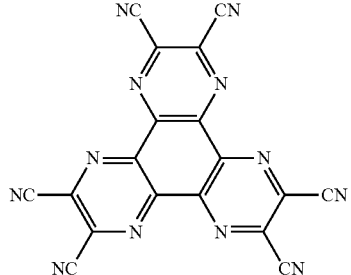 [SMILES: N#Cc1nc2c3nc(C#N)c(C#N)nc3c3nc(C#N)c(C#N)nc3c2nc1C#N] | US20020158242 |
| Metal organometallic complexes | 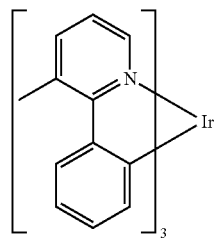 | US20060240279 |
| Cross-linkable compounds | 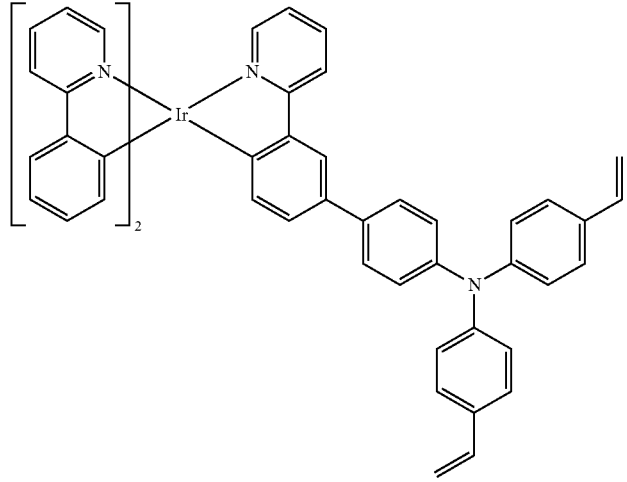 | US20080220265 |
| Polythiophene based polymers and copolymers | 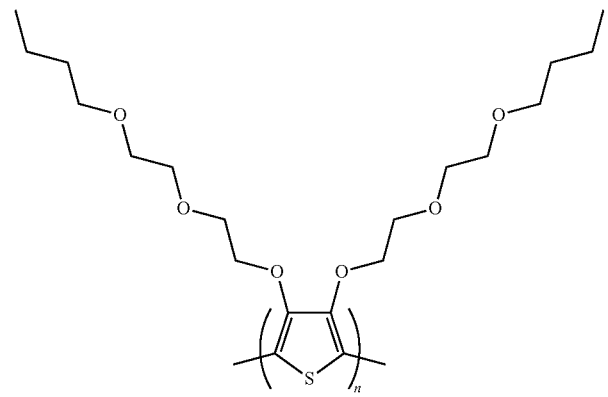 | WO 2011075644<br>EP2350216 |

TABLE 1-continued

| MATERIAL | EXAMPLES OF MATERIAL | PUBLICATIONS |
| --- | --- | --- |
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |
| | | J. Mater. Chem. 3, 319 (1993) |

TABLE 1-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 1-continued
| MATERIAL | EXAMPLES OF MATERIAL | PUBLICATIONS |
|---|---|---|
| Triarylamine with (di)benzothiophene/ (di)benzofuran | 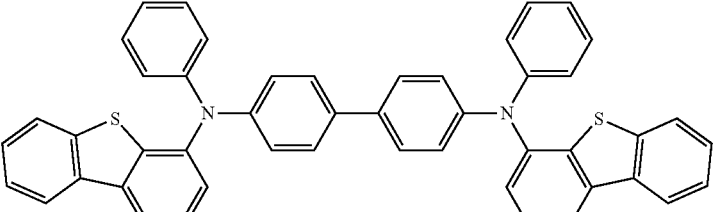 | US20070278938, US20080106190 US20110163302 |
| Indolocarbazoles | 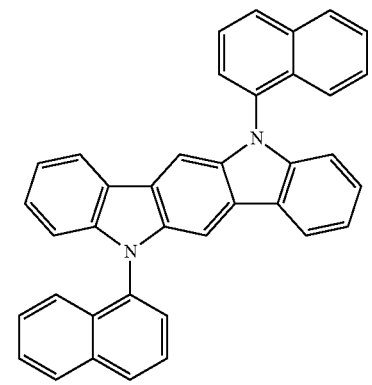 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 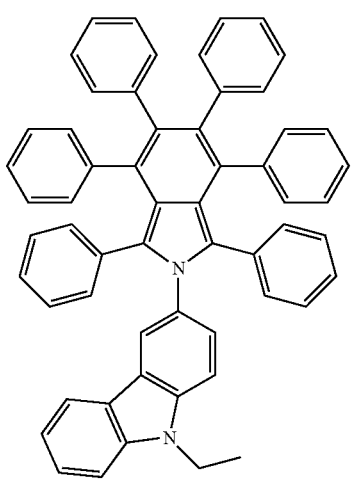 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 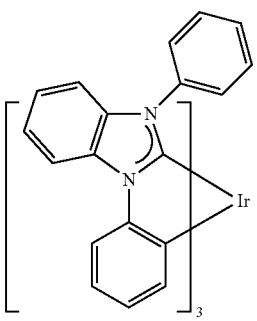 | US20080018221 |

TABLE 1-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., $Alq_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 1-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett. 78, 1622 (2001) |
| | | US20030175553 |
| | | WO2001039234 |

TABLE 1-continued

| MATERIAL | EXAMPLES OF MATERIAL | PUBLICATIONS |
|---|---|---|
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

TABLE 1-continued
| MATERIAL | EXAMPLES OF MATERIAL | PUBLICATIONS |
|---|---|---|
| | 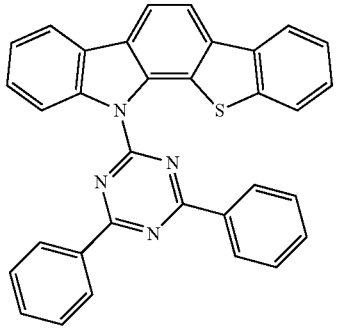 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 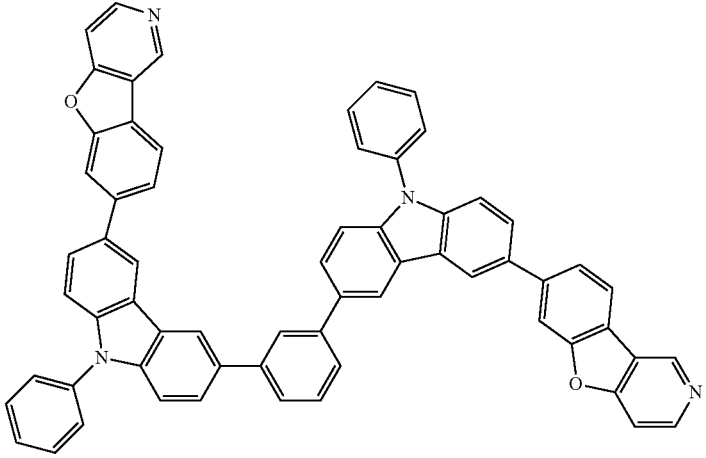 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 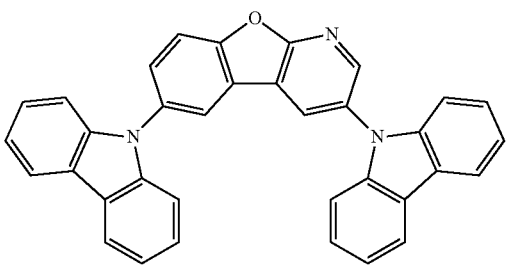 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 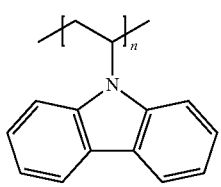 | Appl. Phys. Lett. 77, 2280 (2000) |
| Spirofluorene compounds | 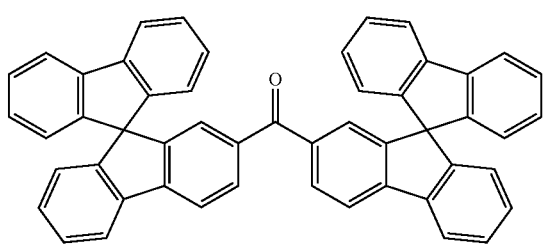 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 1-continued
| MATERIAL | EXAMPLES OF MATERIAL | PUBLICATIONS |
|---|---|---|
| Metal phenoxybenzooxazole compounds | 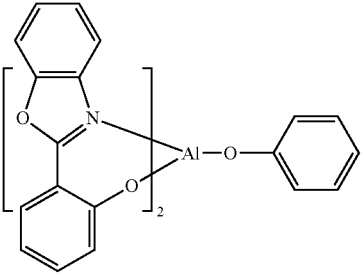 | WO2005089025 |
| | 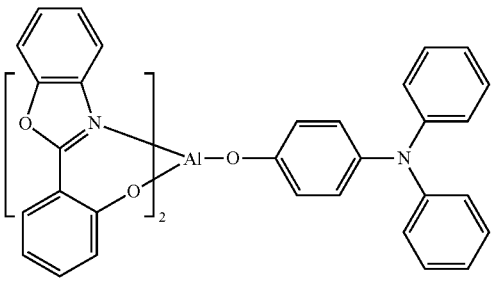 | WO2006132173 |
| | 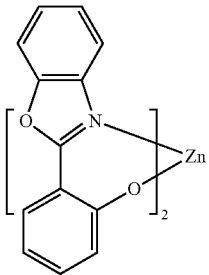 | JP200511610 |
| Spirofluorene-carbazole compounds | 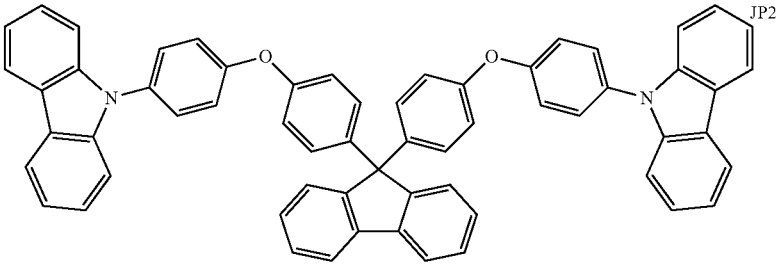 | JP2007254297 |
| | 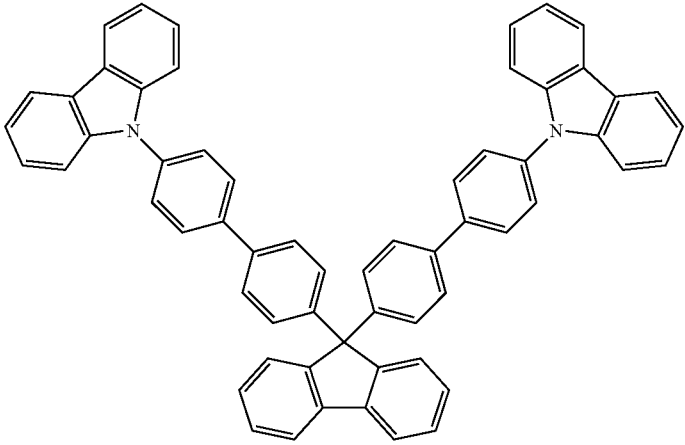 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 1-continued

| MATERIAL | EXAMPLES OF MATERIAL | PUBLICATIONS |
| --- | --- | --- |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 1-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran- carbazole compounds | | WO2006114966, US20090167162 |
| | | US20090167162 |

TABLE 1-continued
| MATERIAL | EXAMPLES OF MATERIAL | PUBLICATIONS |
|---|---|---|
| | 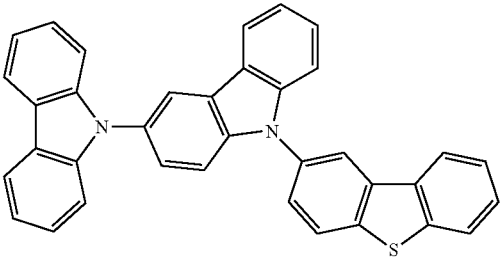 [SMILES: c1ccc2c(c1)sc1ccc(-n3c4ccccc4c4cc(-n5c6ccccc6c6ccccc65)ccc43)cc12] | WO2009086028 |
| | 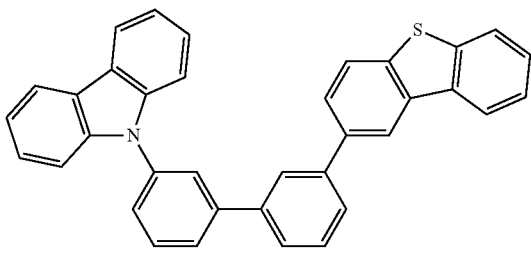 [SMILES: c1cc(-c2cccc(-n3c4ccccc4c4ccccc43)c2)cc(-c2ccc3sc4ccccc4c3c2)c1] | US20090030202, US20090017330 |
| | 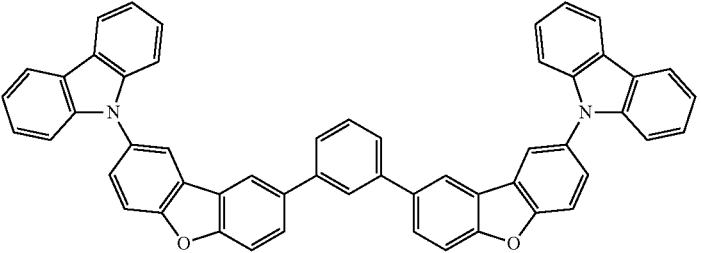 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 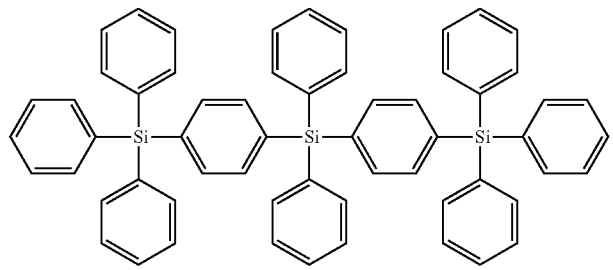 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 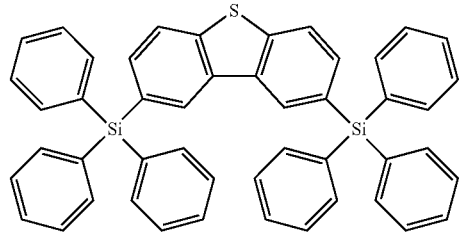 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
| --- | --- | --- |
| Silicon/ Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 1-continued
| MATERIAL | EXAMPLES OF MATERIAL | PUBLICATIONS |
|---|---|---|
| | Phosphorescent dopants | |
| | Red dopants | |
| Heavy metal porphyrins (e.g., PtOEP) | 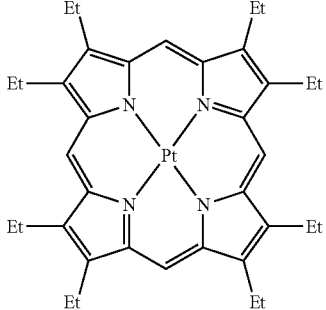 | Nature 395, 151 (1998) |
| Iridium(III) organometallic complexes | 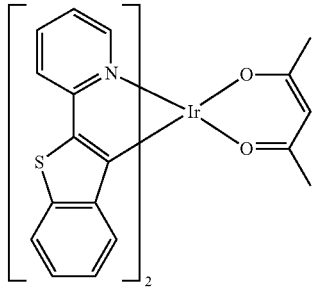 | Appl. Phys. Lett. 78, 1622 (2001) |
| | 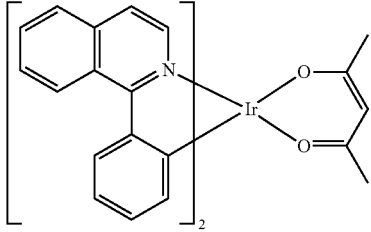 | US2006835469 |
| | 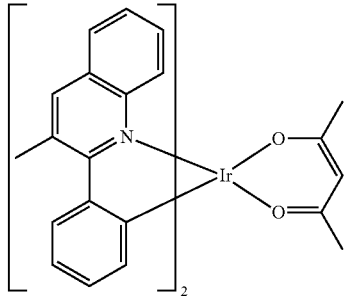 | US2006835469 |
| | 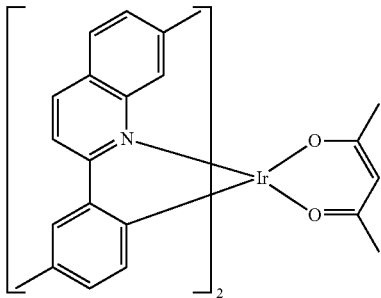 | US20060202194 |

TABLE 1-continued

| MATERIAL | EXAMPLES OF MATERIAL | PUBLICATIONS |
| --- | --- | --- |
|  |  | US20060202194 |
|  |  | US20070087321 |
|  |  | US20080261076<br>US20100090591 |
|  |  | US20070087321 |
|  |  | Adv. Mater. 19, 739 (2007) |

TABLE 1-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 1-continued

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |
| Green dopans | | |
| Iridium(III) organometallic complexes | and its derivatives | Inorg. Chem. 40, 1704 (2001) |
| | | US20020034656 |

TABLE 1-continued
| MATERIAL | EXAMPLES OF MATERIAL | PUBLICATIONS |
|---|---|---|
| | 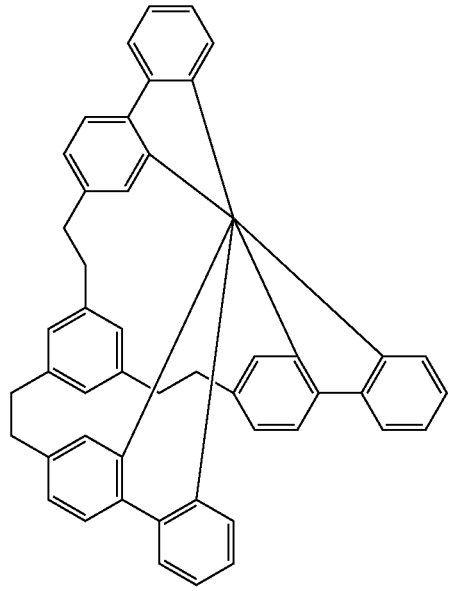 | U.S. Pat. No. 7,332,232 |
| | 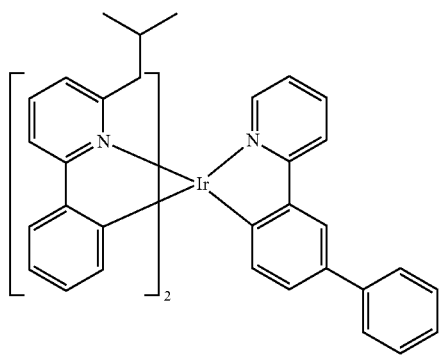 | US20090108737 |
| | 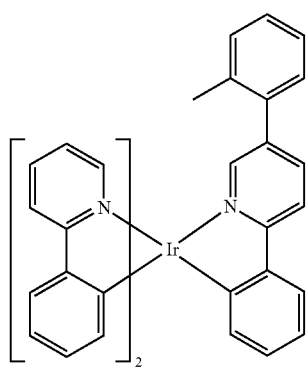 | WO2010028151 |

TABLE 1-continued
| MATERIAL | EXAMPLES OF MATERIAL | PUBLICATIONS |
|---|---|---|
| | 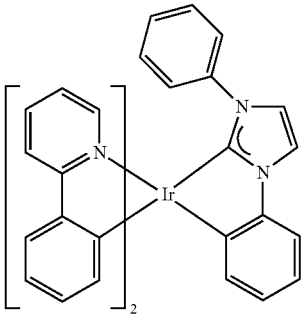 | EP1841834B |
| | 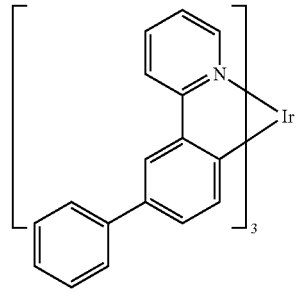 | US20060127696 |
| | 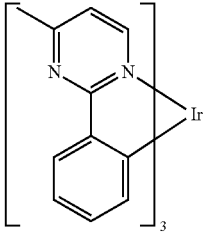 | US20090039776 |
| | 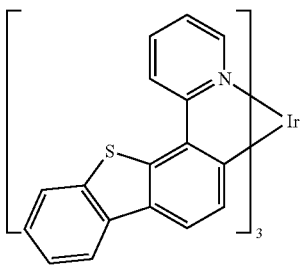 | U.S. Pat. No. 6,921,915 |
| | 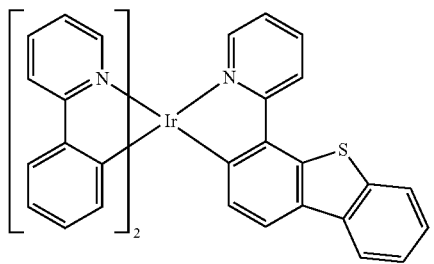 | US20100244004 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US20060008670 JP2007123392 |
| | | WO2010086089, WO2011044988 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 1-continued

| MATERIAL | EXAMPLES OF MATERIAL | PUBLICATIONS |
|---|---|---|
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 1-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 1-continued
| MATERIAL | EXAMPLES OF MATERIAL | PUBLICATIONS |
|---|---|---|
| Gold complexes | 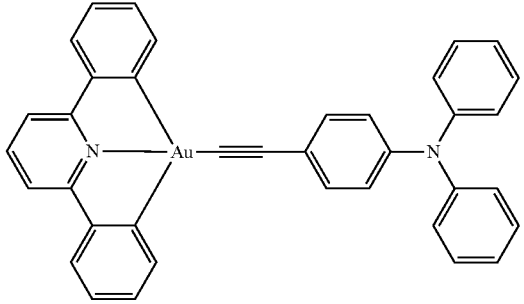 | Chem. Commun. 2906 (2005) |
| Rhenium(III) complexes | 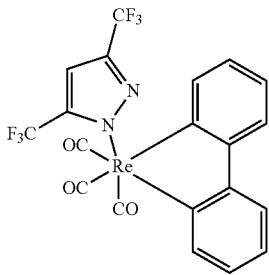 | Inorg. Chem. 42, 1248 (2003) |
| Osmium(II) complexes | 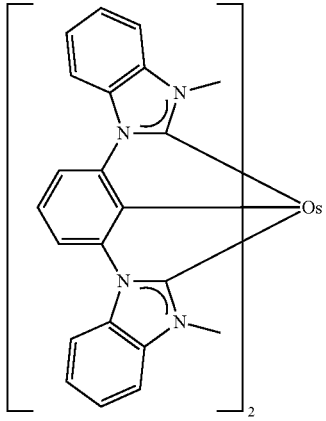 | U.S. Pat. No. 7,279,704 |
| Deuterated organometallic complexes | 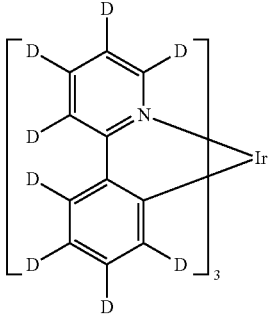 | US20030138657 |

TABLE 1-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |

Blue dopants

| | | |
|---|---|---|
| Iridium(III) organometallic complexes | | WO2002002714 |
| | | WO2006009024 |
| | | US20060251923<br>US20110057559<br>US20110204333 |

TABLE 1-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 1-continued

| MATERIAL | EXAMPLES OF MATERIAL | PUBLICATIONS |
|---|---|---|
|  |  | U.S. Pat. No. 7,338,722 |
|  |  | US20020134984 |
|  |  | Angew. Chem. Int. Ed. 47, 1 (2008) |
|  |  | Chem. Mater. 18, 5119 (2006) |
|  |  | Inorg. Chem. 46, 4308 (2007) |

TABLE 1-continued

| MATERIAL | EXAMPLES OF MATERIAL | PUBLICATIONS |
| --- | --- | --- |
| | | WO2005123873 |
| | | WO2005123873 |
| | | WO2007004380 |
| | | WO2006082742 |
| Osmium(II) complexes | | U.S. Pat. No. 7,279,704 |

TABLE 1-continued

| MATERIAL | EXAMPLES OF MATERIAL | PUBLICATIONS |
|---|---|---|
| | 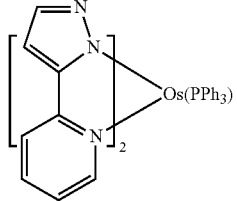 | Organometallics 23, 3745 (2004) |
| Gold complexes | 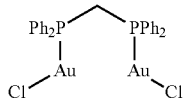 | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | 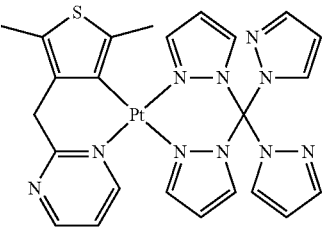 | Appl. Phys. Lett. 75, 4 (1999) |
| | 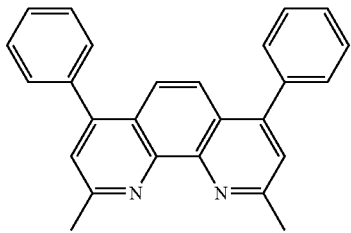 [SMILES: Cc1cc(-c2ccccc2)c2ccc3c(-c4ccccc4)cc(C)nc3c2n1] | Appl. Phys. Lett. 79, 449 (2001) |
| Metal 8-hydroxyquinolates (e.g., BAlq) | 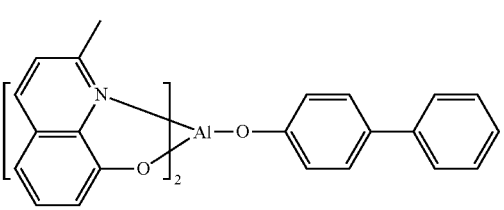 | Appl. Phys. Lett. 81, 162 (2002) |

TABLE 1-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 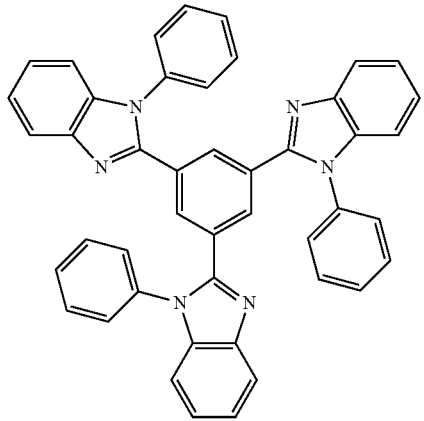 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 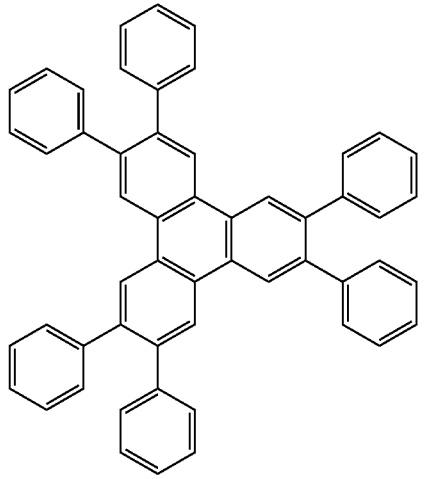 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 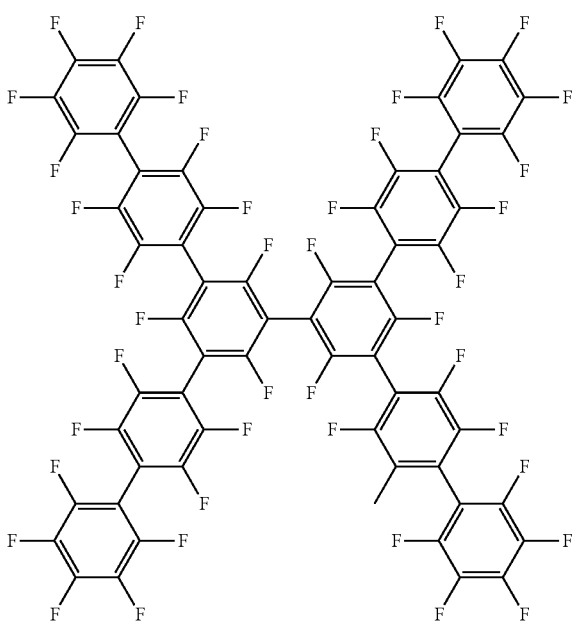 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 1-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE 1-continued

| MATERIAL | EXAMPLES OF MATERIAL | PUBLICATIONS |
|---|---|---|
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 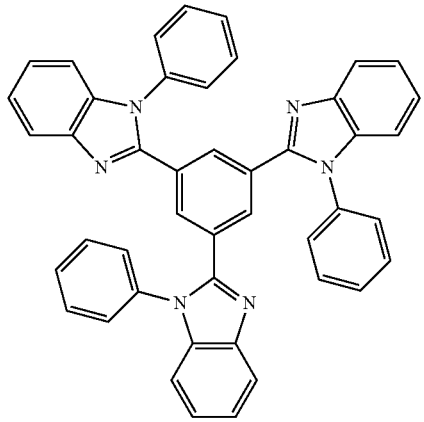 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 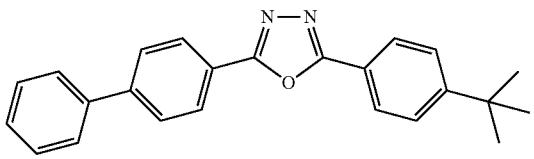 [SMILES: CC(C)(C)c1ccc(-c2nnc(-c3ccc(-c4ccccc4)cc3)o2)cc1] | Appl. Phys. Lett. 55, 1489 (1989) |
| | 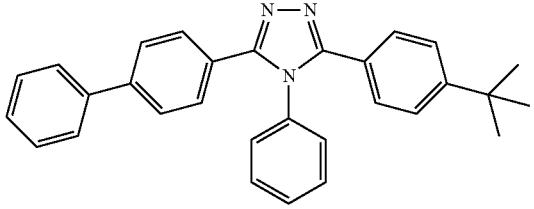 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 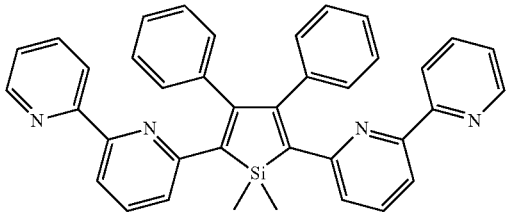 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 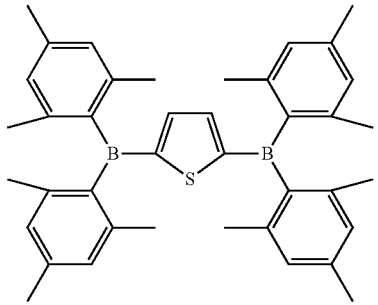 | J. Am. Chem. Soc. 120, 9714 (1998) |
| Fluorinated aromatic compounds | 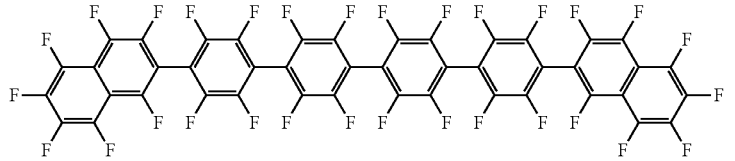 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 1-continued

| MATERIAL | EXAMPLES OF MATERIAL | PUBLICATIONS |
|---|---|---|
| Fullerene (e.g., C60) | 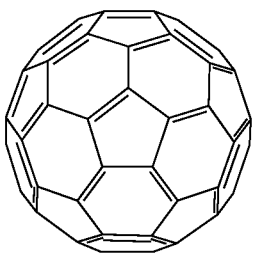 | US20090101870 |
| Triazine complexes | 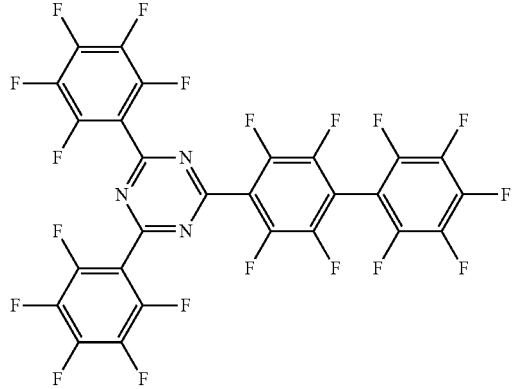 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 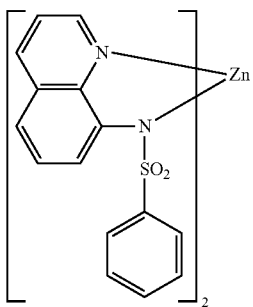 | U.S. Pat. No. 6,528,187 |

EXPERIMENTAL

Synthesis of Compound 1

A mixture solution of 2-bromo-9H-carbazole (10.0 g, 40.6 mmol), iodobenzene (12.43 g, 61.0 mmol), CuI (0.774 g, 4.06 mmol), (1R,2S)-cyclohexane-1,2-diamine (0.987 ml, 8.13 mmol), and $K_3PO_4$ (17.25 g, 81 mmol) in dioxane (150 ml) was refluxed under nitrogen for 48 h.

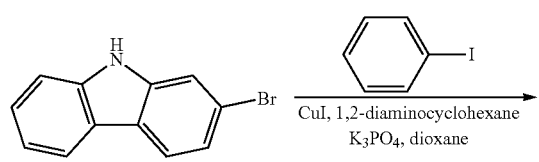

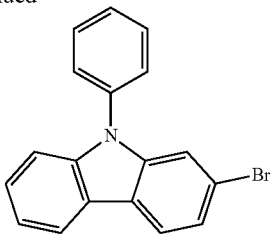

After cooling to room temperature, the mixture was filtered through a plug of Celite® and the solid was washed with DCM. The combined filtrate was evaporated and purified by column chromatography on silica gel with hexane/DCM (9/1, v/v) as eluent to yield 2-bromo-9-phenyl-9H-carbazole (7.4 g, 54%) as a white solid.

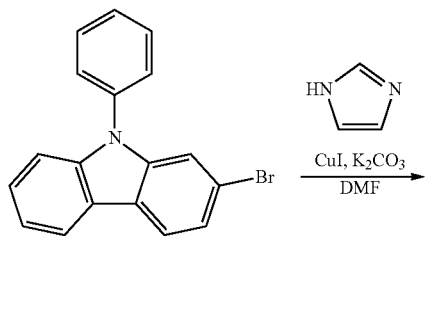
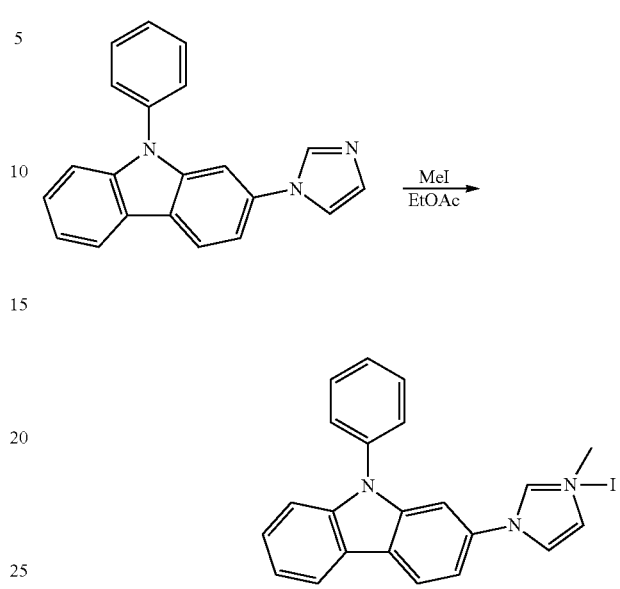

A mixture of 2-bromo-9-phenyl-9H-carbazole (11.6 g, 36.0 mmol), imidazole (3.68 g, 54.0 mmol), CuI (1.371 g, 7.20 mmol) and $K_2CO_3$ (7.46 g, 54.0 mmol) in DMF (150 ml) was heated under nitrogen at 140° C. overnight. After cooling to room temperature, the mixture was quenched with water and extracted with DCM. The combined extracts were filtered through a short plug of Celite®. The filtrate was washed with water and dried over $Na_2SO_4$. Upon evaporation of the solvent, the residue was purified by column chromatography on silica gel with DCM/MeOH (10/0 to 95/5, v/v) as eluent to yield 2-(1H-imidazol-1-yl)-9-phenyl-9H-carbazole (11.1 g, 99%) as a liquid.

A solution of 2-(1H-imidazol-1-yl)-9-phenyl-9H-carbazole (3.5 g, 11.31 mmol) and iodomethane (3.52 ml, 56.6 mmol) in EtOAc (100 ml) was stirred at room temperature for 48 hours. The white precipitate was collected by filtration, washed with EtOAc and recrystallized from ethanol to yield 1-iodo-1-methyl-3-(9-phenyl-9H-carbazol-2-yl)-2,3-dihydro-1H-imidazol-1-ium-2-ide (3.5 g, 68%) as white crystals.

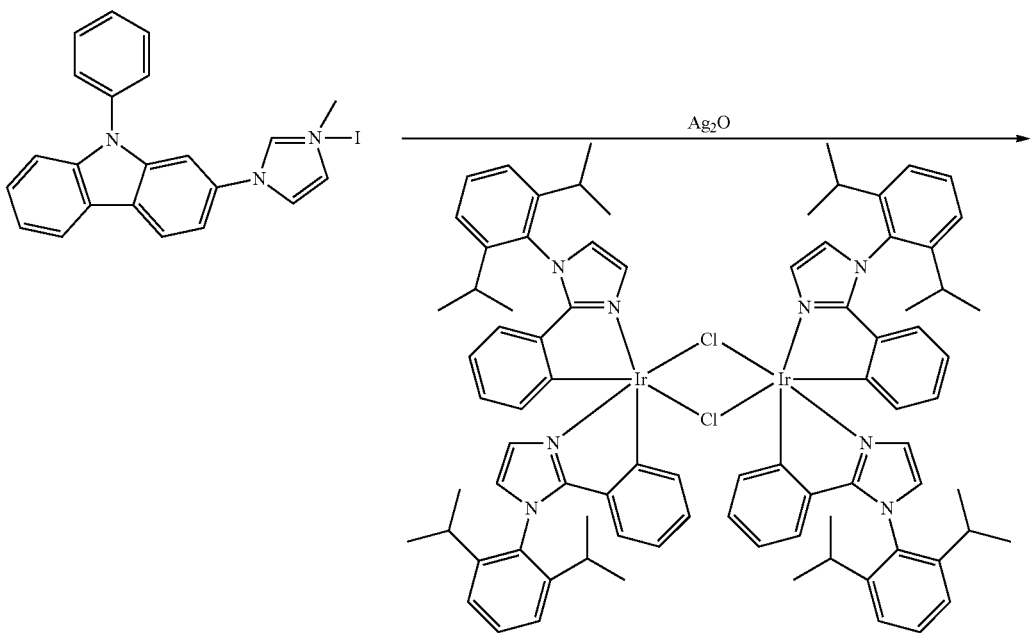

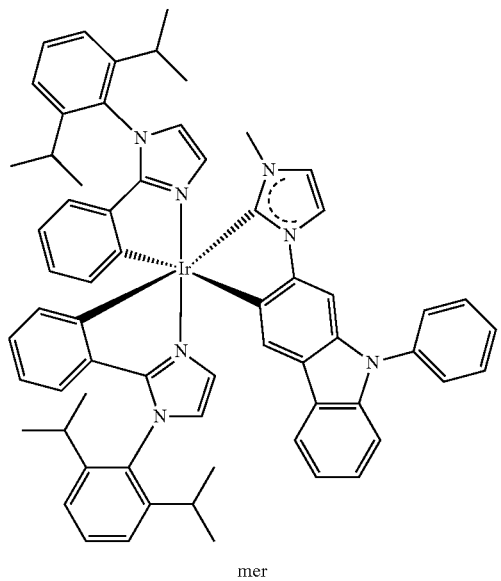

mer

A solution of 1-iodo-1-methyl-3-(9-phenyl-9H-carbazol-2-yl)-2,3-dihydro-1H-imidazol-1-ium-2-ide (2.5 g, 5.54 mmol) and Ag$_2$O (0.642 g, 2.77 mmol) in acetonitrile (150 ml) was stirred under nitrogen at room temperature overnight to yield a white suspension. The acetonitrile was evaporated off, and the residue was re-dissolved together with Ir-dimer (2 g, 1.198 mmol) in THF (150 ml). The resultant solution was refluxed under nitrogen overnight. After cooling to room temperature, the solution was filtered through a short plug of Celite® and washed with DCM. Upon evaporation of the solvent, the residue was purified by column chromatography on triethylamine-treated silica gel with hexane/DCM (9/1 to 4/1, v/v) as eluent to yield the mer form of the Compound 1 (2.3 g, 83%) as yellow crystals.

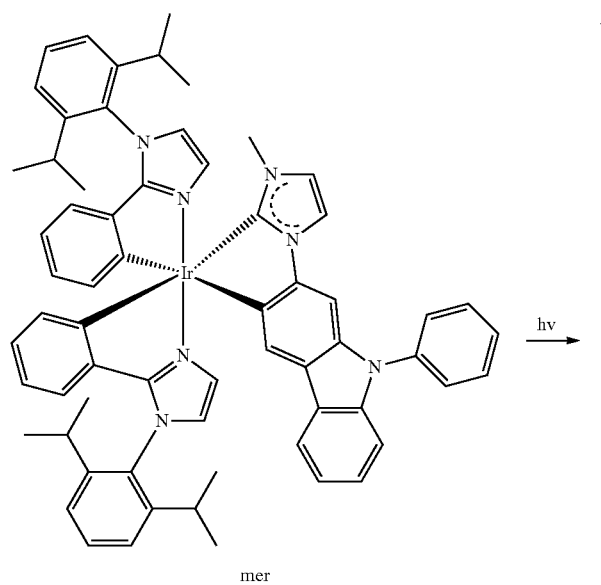

mer hv →

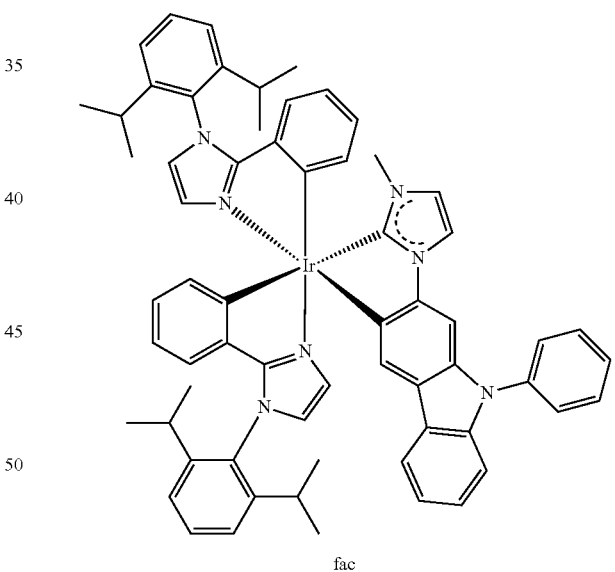

fac

A solution of mer form of Compound 1 (2 g, 1.782 mmol) in DMSO (400 ml) was irradiated (360 nm) with UV light under nitrogen for 4 h. Upon evaporation of the solvent, the residue was purified by column chromatography on triethylamine-treated silica gel with hexane/DCM (9/1 to 4/1, v/v) as eluent to yield Compound 1 (1.4 g, 70%) as yellow crystals.

Compound 1

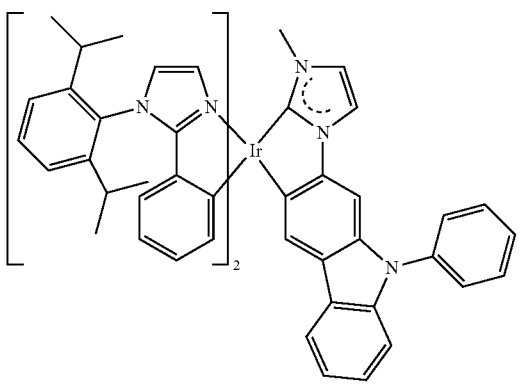

Synthesis of Compound 2

A mixture solution of 3-bromo-9-phenyl-9H-carbazole (7.9 g, 24.52 mmol), 1H-imidazole (2.504 g, 36.8 mmol), CuI (1.401 g, 7.36 mmol) and K$_2$CO$_3$ (5.08 g, 36.8 mmol) in DMF (100 ml) was heated at 140° C. under nitrogen overnight.

After cooling to room temperature, the mixture solution was filtered through a short plug of Celite®. The filtrate was poured into water, extracted with DCM and dried over Na$_2$SO$_4$. Upon evaporation of the solvent, the residue was purified by column chromatography on silica gel with DCM/EtOAc (4/1, v/v) as eluent to yield 3-(1H-imidazol-1-yl)-9-phenyl-9H-carbazole (7 g, 92%) as a white powder.

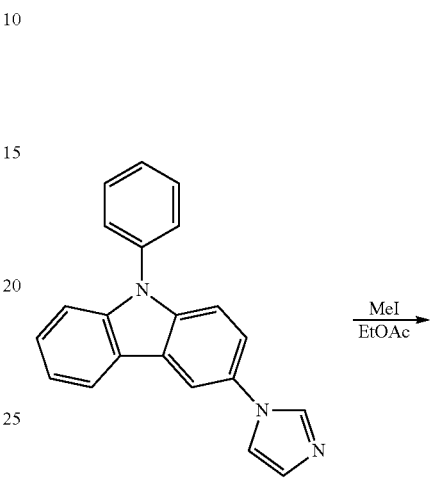

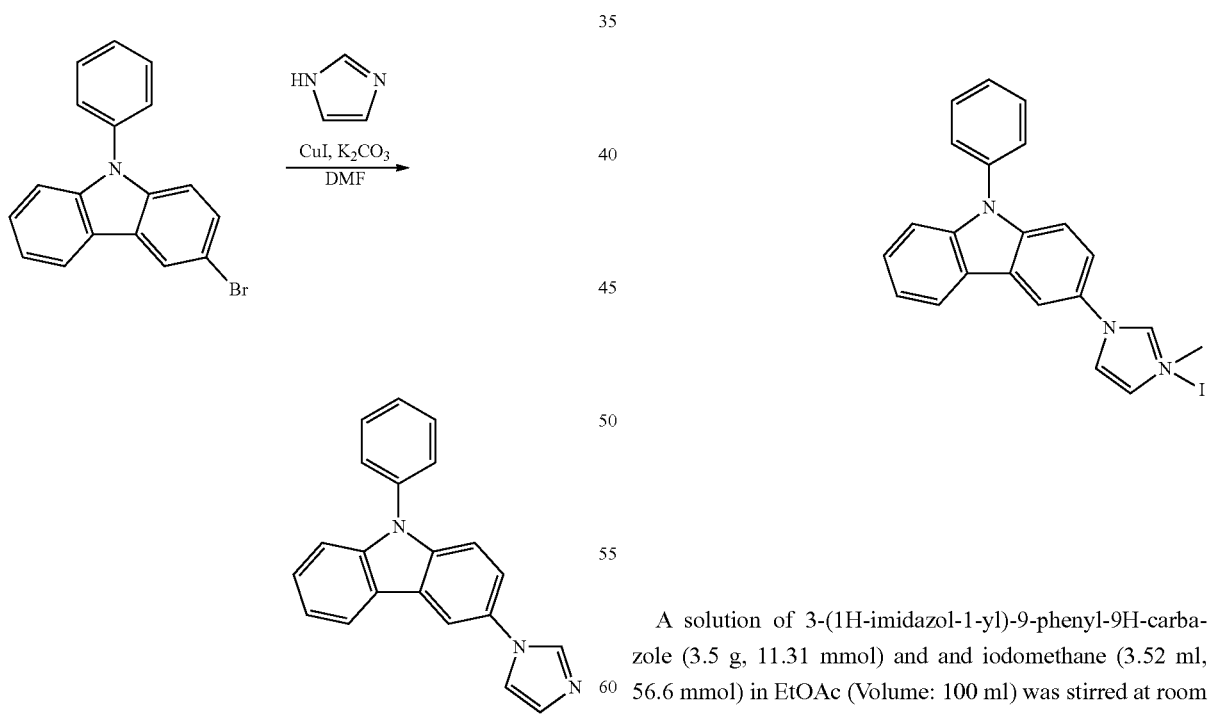

A solution of 3-(1H-imidazol-1-yl)-9-phenyl-9H-carbazole (3.5 g, 11.31 mmol) and and iodomethane (3.52 ml, 56.6 mmol) in EtOAc (Volume: 100 ml) was stirred at room temperature for 72 h. The white precipitate was collected by filtration, washed with EtOAc and recrystallized from ethanol to yield 1-iodo-1-methyl-3-(9-phenyl-9H-carbazol-3-yl)-2,3-dihydro-1H-imidazol-1-ium-2-ide (3.4 g, 67%) as white crystals.

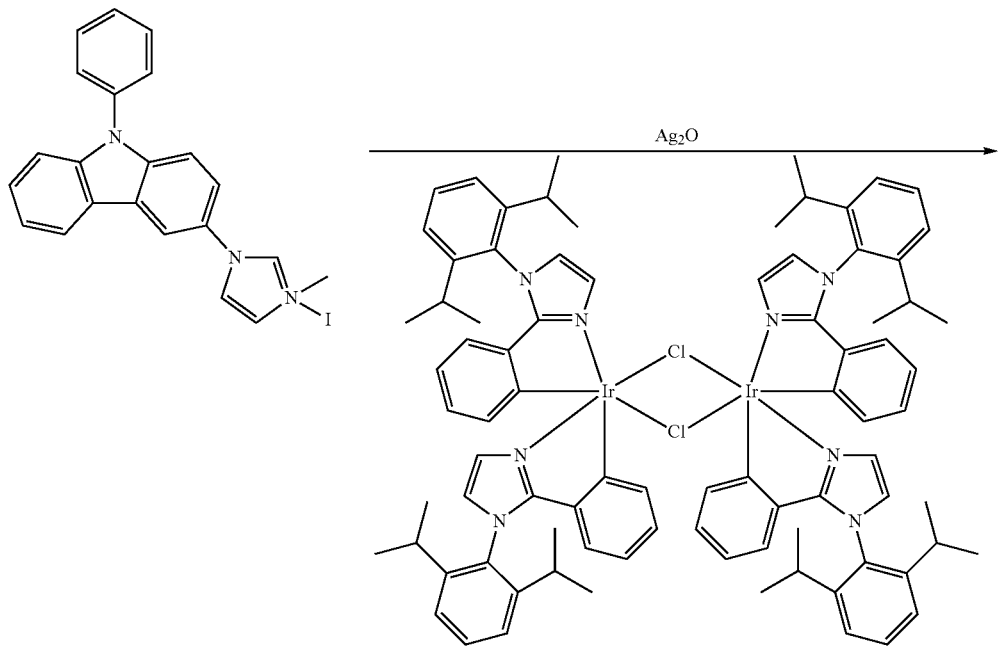

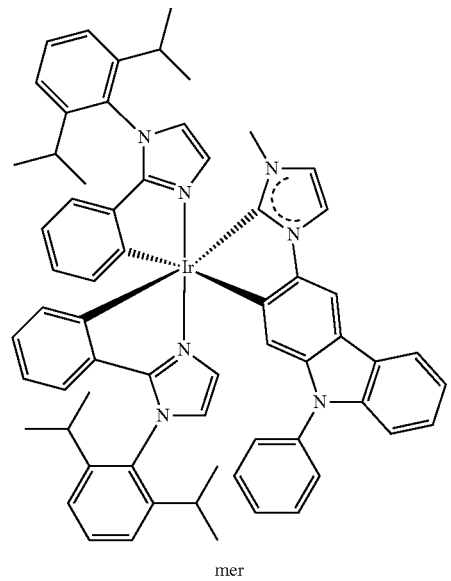

mer

A mixture of 1-iodo-1-methyl-3-(9-phenyl-9H-carbazol-3-yl)-2,3-dihydro-1H-imidazol-1-ium-2-ide (2.5 g, 5.54 mmol) and Ag$_2$O (0.642 g, 2.77 mmol) in acetonitrile (150 ml) was stirred under nitrogen at room temperature overnight. The acetonitrile was evaporated under reduced pressure. The solid was re-dissolved together with Ir-dimer (2 g, 1.20 mml) in THF (150 ml) and refluxed under nitrogen overnight. After cooling to room temperature, the reaction mixture was filtered through a short plug of Celite® and the filtrate was evaporated. The residue was purified by column chromatography on triethylamine-treated silica gel with hexane/DCM (9/1 to 3/1, v/v) as eluent to yield the mer-form of Compound 2 (2.3 g, 85%) as yellow crystals.

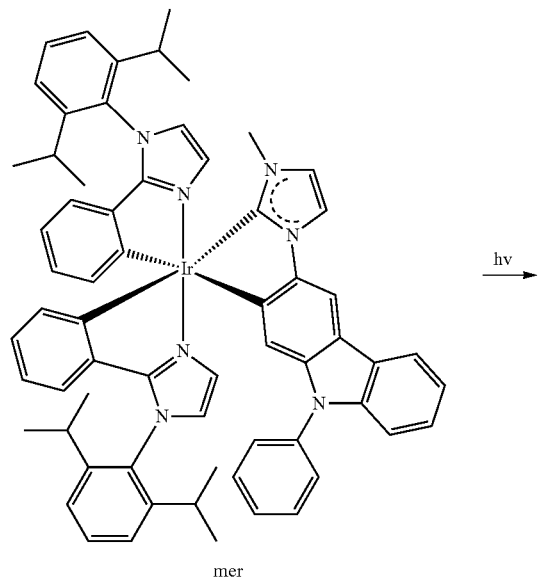

mer

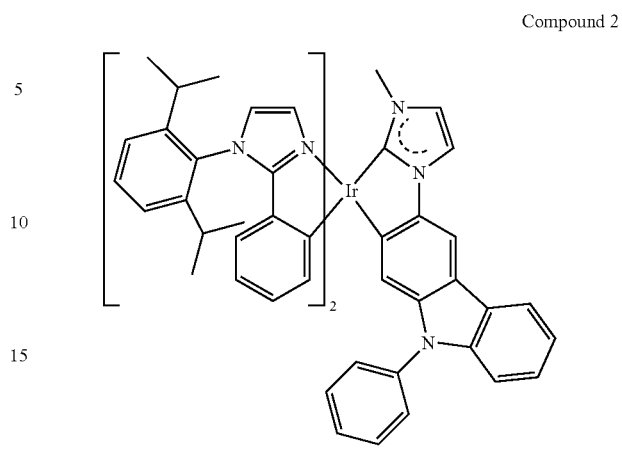

Compound 2

Synthesis of Compound 5

Into a suspension of 9H-pyrido[2,3-b]indole (8 g, 47.6 mmol) in DCM (350 ml) was added dropwise a solution of bromine (2.92 ml, 57.1 mmol) in DCM (60 ml) at room temperature during a period of 4 h.

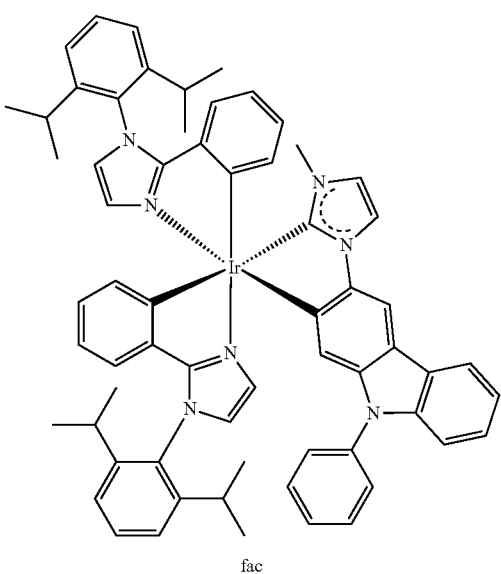

fac

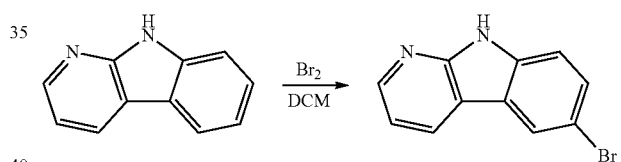

The reaction mixture was stirred at room temperature overnight, quenched with an aqueous solution of $Na_2S_2O_3$. The solid was isolated by filtration. The filtrate was washed with water and evaporated to obtain another solid. The combined solids were recrystallized from EtOAc to yield 6-bromo-9H-pyrido[2,3-b]indole (9.0 g, 77%) as white crystals.

A solution of mer-form of Compound 2 (2.3 g, 2.049 mmol) in DMSO (200 ml) was irradiated (360 nm) with UV light under nitrogen for 3 h. Upon evaporation of the solvent, the residue was purified by column chromatography on triethylamine-treated silica gel with hexane/DCM (9/1 to 4/1, v/v) as eluent to yield fac-form of Compound 2 (1.6 g, 70%) as yellow crystals.

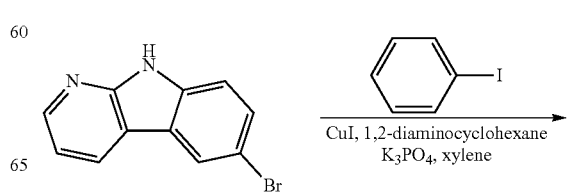

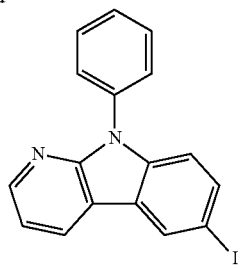

A solution of 6-bromo-9H-pyrido[2,3-b]indole (4.42 g, 17.89 mmol), iodobenzene (2.94 ml, 26.8 mmol), CuI (3.41 g, 17.89 mmol), cyclohexane-1,2-diamine (0.435 ml, 3.58 mmol) and K$_3$PO$_4$ (7.59 g, 35.8 mmol) in xylene (250 ml) was refluxed overnight. After cooling to room temperature, the solution was filtered through a short plug of Celite® and the solid was washed with DCM. The combined filtrates were evaporated and the residue was purified by column chromatography on silica gel with DCM as eluent to yield 6-iodo-9-phenyl-9H-pyrido[2,3-b]indole (1.4 g, 21%) as a white solid.

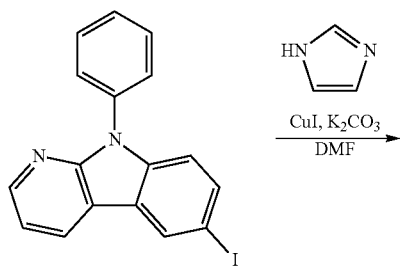

A mixture solution of 6-iodo-9-phenyl-9H-pyrido[2,3-b]indole (1.15 g, 3.11 mmol), 1H-imidazole (0.32, 4.66 mmol), CuI (0.12 g, 0.62 mmol), cyclohexane-1,2-diamine (0.15 ml, 1.24 mmol) and K$_2$CO$_3$ (0.64 g, 4.63 mmol) in DMF (40 ml) was heated at 140° C. overnight. After cooling to room temperature, the mixture solution was poured into water (50 ml) and extracted with DCM. The combined extracts were washed with brine, dried over Na$_2$SO$_4$ and evaporated. The residue was purified by column chromatography on silica gel with DCM/EtOAc (3/1, v/v) as eluent to yield 6-(1H-imidazol-1-yl)-9-phenyl-9H-pyrido[2,3-b]indole (0.6 g, 62%) as a white solid.

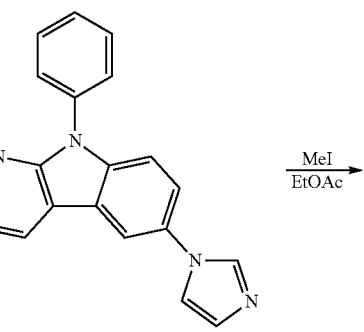

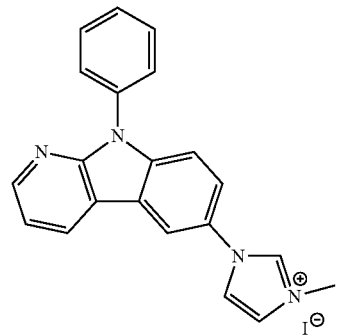

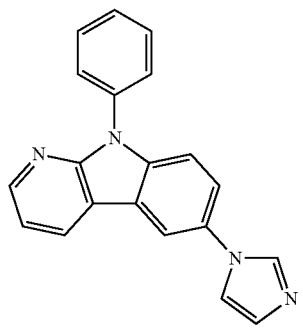

A solution of 6-(1H-imidazol-1-yl)-9-phenyl-9H-pyrido[2,3-b]indole (0.6 g, 1.933 mmol) and iodomethane (0.60 ml, 9.67 mmol) in EtOAc (200 ml) was stirred at room temperature for 60 h. The precipitate was isolated and washed with EtOAc to yield 3-methyl-1-(9-phenyl-9H-pyrido[2,3-b]indol-6-yl)-1H-imidazol-3-ium iodide (0.48 g, 55%) as a white solid.

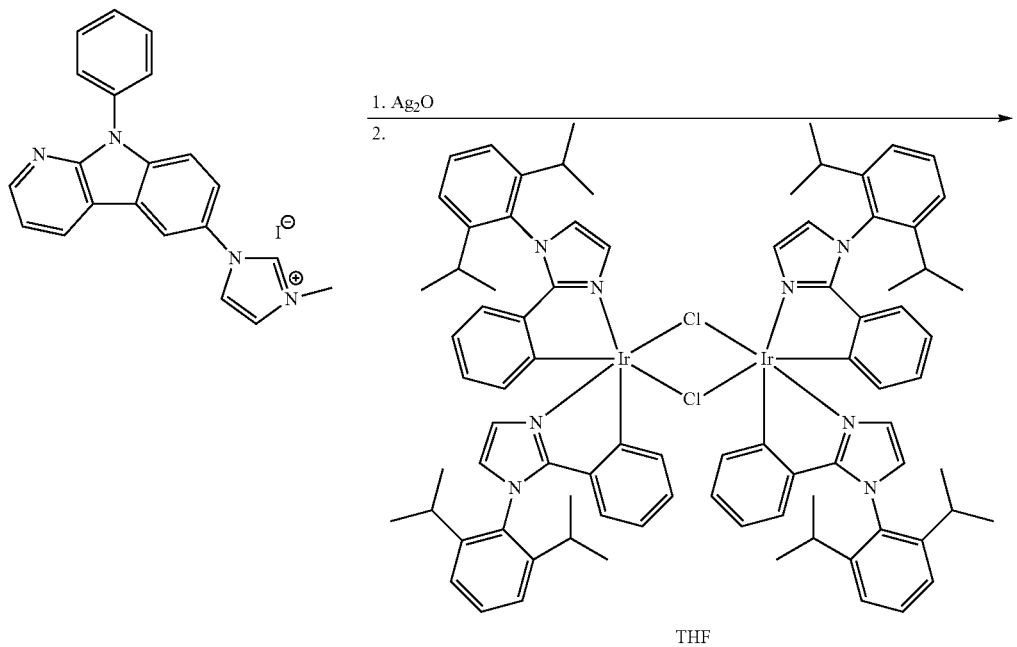

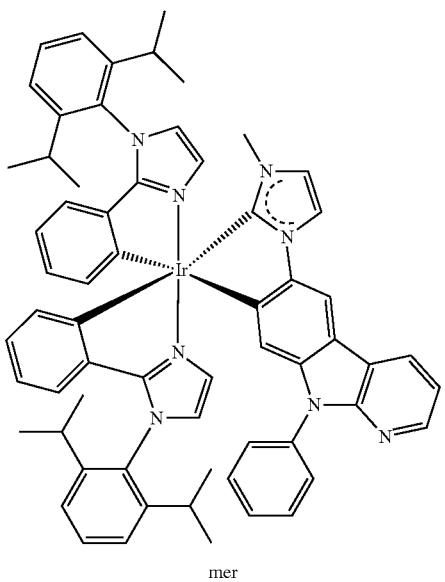

mer

A suspension of 3-methyl-1-(9-phenyl-9H-pyrido[2,3-b]indol-6-yl)-1H-imidazol-3-ium iodide (0.48 g, 1.061 mmol) and Ag$_2$O (0.123 g, 0.531 mmol) in acetonitrile (50 ml) was stirred under nitrogen at room temperature overnight. The solvent was evaporated, and the residue was refluxed overnight under nitrogen together with the Ir-dimer (0.59 g, 0.35 mmol) in THF (50 ml). The solid was filtered off and the residue was purified by column chromatography on TEA-treated silica gel with hexane/DCM (4/1, v/v) as eluent to yield mer-form of Compound 5 (0.3 g, 38%) as a yellow solid.

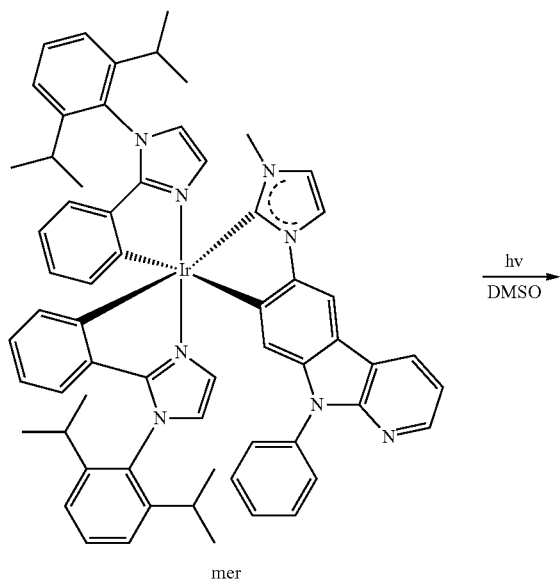

mer

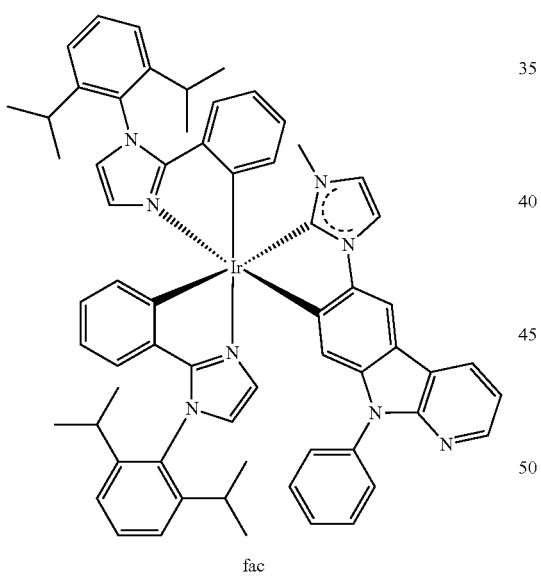

fac

A solution of mer-form of Compound 5 (0.3 g, 0.267 mmol) in DMSO (50 ml) was irradiated with UV for 4 h. Upon evaporation off the solvent, the residue was purified by column chromatography on triethylamine-treated silica gel with hexane/DCM (4/1 to 2/1, v/v) as eluent to yield fac-form of Compound 5 as yellow crystals.

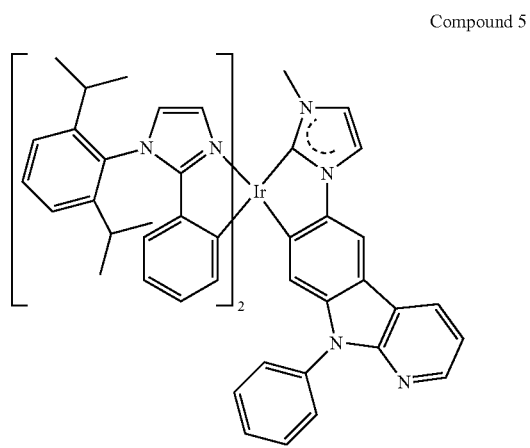

Compound 5

Computational Results

The HOMO/LUMO energy levels and triplet energy (T1) of selected compounds were calculated using the Gaussian software package at the B3LYP/cep-31g functional and basis set, and the results are presented in Table 2. Some of the heteroleptic iridium complexes described herein were compared with similar heteroleptic iridium complexes: comparative compound 1 (CC-1) and comparative compound 2 (CC-2):

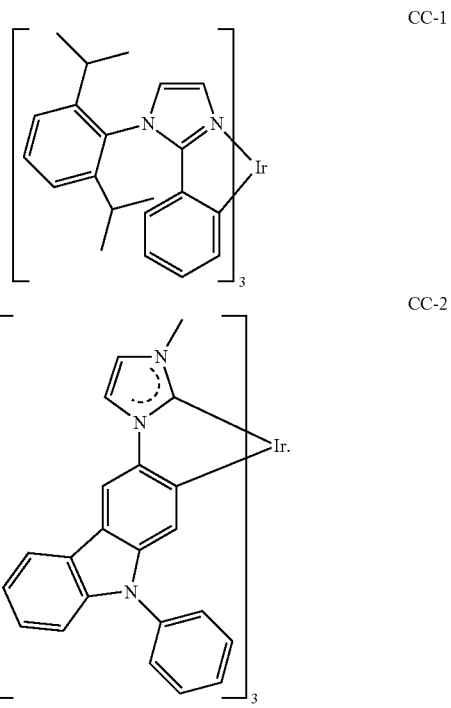

Compared to homoleptic compound CC-1, the heteroleptic Compound 2 has higher triplet energy, 2.73 eV vs 2.67 eV, suggesting that the carbazole-imidazole-carbene ligand could effectively blue-shift the emission spectra. Furthermore, compared to homoleptic compound CC-2, the heteroleptic Compound 2 has elevated HOMO level, −4.46 eV vs −4.66 eV, which is attributable to the introduction of phenylimidzole ligand in Compound 2. A shallower HOMO level facilitates hole trapping and promotes charge recombination in the emitting layer, both of which are desirable for efficient and stable devices. In essence, the heteroleptic structures enable modulation of HOMO/LUMO levels, emission spectra and charge transport properties, and thus offers the opportunity to develop efficient and long-lasting phosphorescent OLEDs with blue emission.

TABLE 2

| Compound | HOMO (eV) | LUMO (eV) | T1 (eV) |
|---|---|---|---|
| CC-1 | −4.42 | −0.63 | 2.67 |
| CC-2 | −4.66 | −0.51 | 2.81 |
| Compound 2 | −4.46 | −0.68 | 2.73 |

Device Examples

The structures of the materials used in the device examples are shown below:

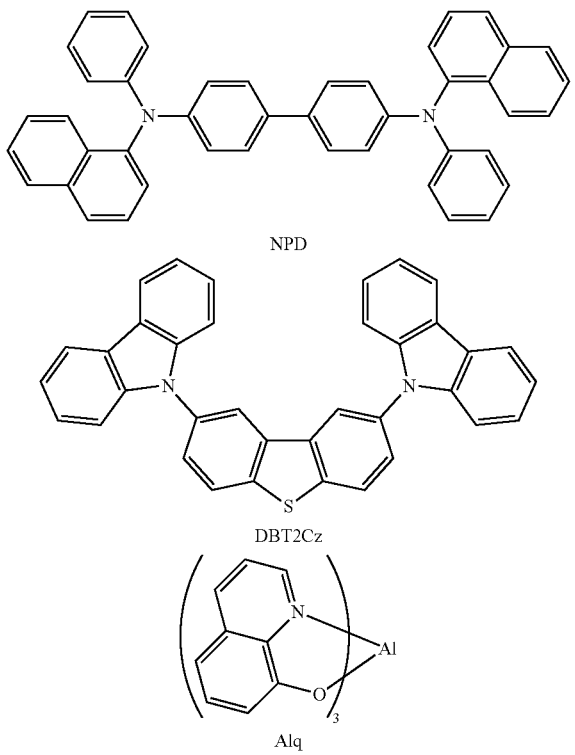

NPD

DBT2Cz

Alq

All example devices were fabricated by high vacuum (<10$^{-7}$ Torr) thermal evaporation (VTE). The anode electrode was 800 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the OLED device used in the Examples and Comparative Device Examples had the following structure: from the ITO surface, 100 Å of LG101 (purchased from LG Chem.) as the hole injection layer, 300 Å of NPD as the hole transporting layer (HTL), 300 Å of Compound DBT2Cz doped with 15 weight percent of a compound of Formula I or comparative compound CC-2 as the emissive layer (EML), 50 Å of compound DBT2Cz as the blocking layer (BL), and 400 Å of Alq as the electron transporting layer (ETL).

Table 3 is a summary of the device data. The driving voltage (V), luminous efficiency (LE) and external quantum efficiency (EQE) were measured at 1000 nits, while the lifetime (LT$_{80}$%) was defined as the time required for the device to decay to 80% of its initial luminance under a constant current density of 20 mA/cm$^2$. The electroluminescence spectra of the devices are consistent with the trend of the calculated triplet energies of emitters, i.e. emitters with higher triplet energies exhibit electroluminescent spectra peaked at shorter wavelength. This suggests that the heteroleptic chemical structure described herein could effectively adjust the emission color of final compounds. On the other hand, compared to device (Device CC-2) with homoleptic compound CC-2 as the emitter, devices (Devices 1 and 2) with compounds of Formula I (Compounds 1 and 2) as emitters require less driving voltage while achieving significantly enhanced efficiency and lifetime. This improvement in device performance is attributable to the more desirable energy levels and charge transport properties derived from the heteroleptic compounds of Formula I.

TABLE 3

| Device | | | | At 1000 nits | | | At 20 mA/cm$^2$ |
|---|---|---|---|---|---|---|---|
| Examples | Emitter | λ$_{max}$ (nm) | CIE x | CIE y | V (V) | LE (cd/A) | EQE (%) | Relative LT$_{80\%}$ |
| Device 1 | Compound 1 | 472 | 0.165 | 0.318 | 5.7 | 14.9 | 7.5 | 17 |
| Device 2 | Compound 2 | 464 | 0.167 | 0.292 | 5.4 | 21.7 | 11.2 | 17 |
| Device CC-2 | CC-2 | 450 | 0.177 | 0.352 | 9.7 | 1.0 | 0.8 | 1 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having the formula:

Formula I

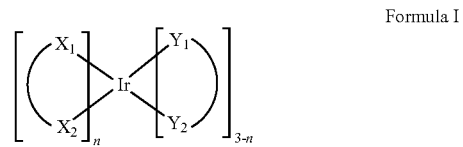

wherein n=1 or 2;

wherein $X_1$-$X_2$ is a bidentate ligand having the formula:

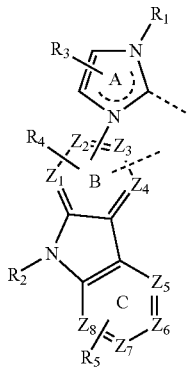

Formula II wherein each of $R_1$, $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R_3$, $R_4$ and $R_5$ may represent mono, di, tri, tetra substitutions, or no substitution;

wherein each of $R_3$, $R_4$ and $R_5$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof, and wherein two adjacent substituents are optionally joined to form into a ring;

wherein each of $Z_1$, $Z_2$, $Z_3$, $Z_4$, $Z_5$, $Z_6$, $Z_7$, and $Z_8$ is independently selected from C, CH or N;

wherein at least one of $Z_1$-$Z_4$ is N;

wherein ring A is connected to ring B through N—C bond; and wherein $Y_1$-$Y_2$ is a different bidentate ligand other than $X_1$-$X_2$.

2. The compound of claim 1, wherein $X_1$-$X_2$ is selected from the group consisting of

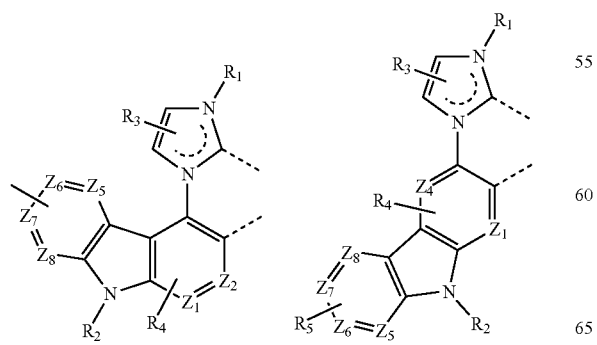

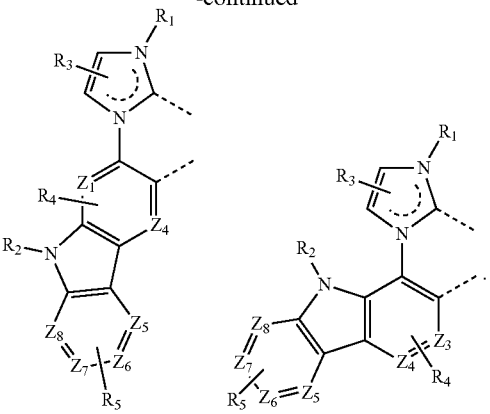

3. The compound of claim 1, wherein $Y_1$-$Y_2$ is selected from the group consisting of

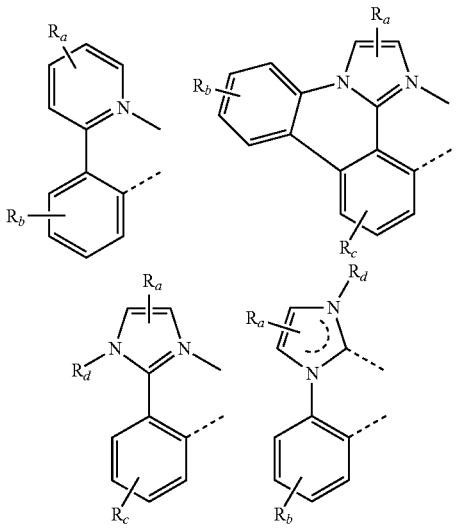

wherein $R_a$ $R_b$ $R_c$ $R_d$ are selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein two adjacent substituents are optionally joined to form into a ring.

4. The compound of claim 3, wherein $Y_1$-$Y_2$ is

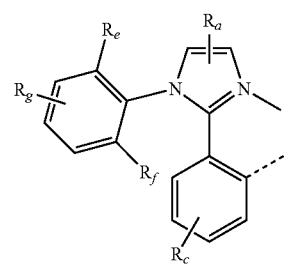

wherein $R_g$ represents mono, di, tri, substitutions or no substitution;

wherein $R_e$, $R_f$ and $R_g$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of $R_e$ and $R_f$ is not hydrogen or deuterium.

5. The compound of claim 1, wherein ring B is coupled to the central Ir atom of Formula I through an Ir—C bond.

6. The compound of claim 1, wherein $R_1$ is selected from the group consisting of deuterium, linear, branched or cyclic $C_1$-$C_8$ alkyl, aryl, alkylaryl, heteroaryl and combinations thereof.

7. The compound of claim 6, wherein $R_1$ is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof; and wherein each group is optionally partially or fully deuterated.

8. The compound of claim 1, wherein $R_2$ is selected from the group consisting of deuterium, linear, branched or cyclic $C_1$-$C_8$ alkyl, aryl, alkylaryl, heteroaryl and combinations thereof.

9. The compound of claim 8, wherein $R_2$ is selected from the group consisting of substituted or unsubstituted benzene and pyridine.

10. The compound of claim 9, wherein $R_3$ is disubstituted and $R_3$ comprises two adjacent substituents joined to form an aryl, alkylaryl or heteroaryl ring.

11. The compound of claim 10, wherein ring A has the structure selected from the group consisting of:

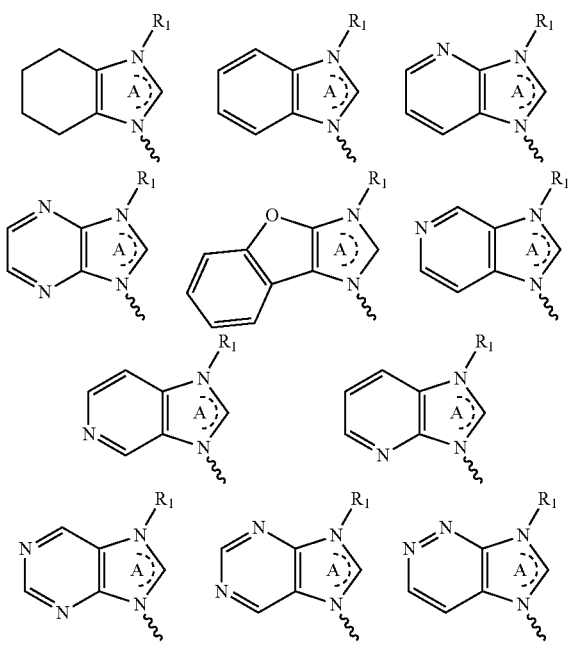
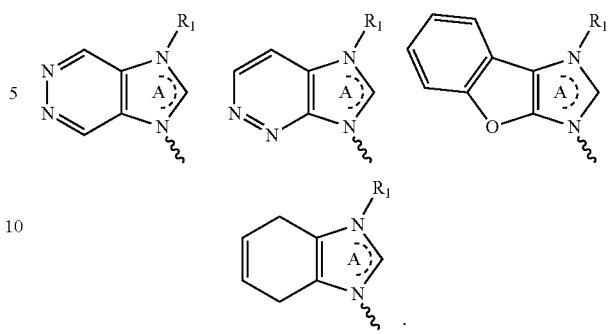

12. The compound of claim 10, wherein ring A has the structure selected from the group consisting of:

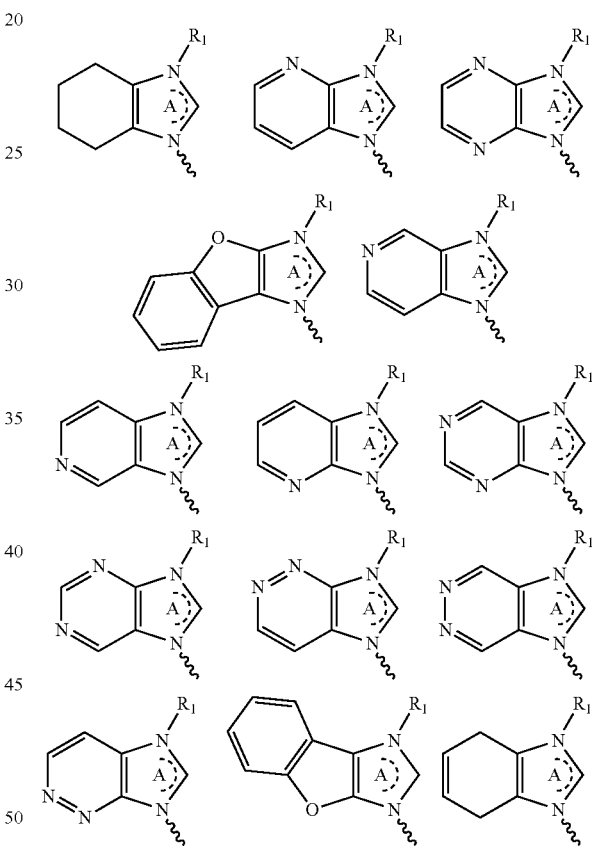

13. The compound of claim 1, wherein $R_3$ is disubstituted and $R_3$ comprises two adjacent substituents joined to form an aryl, alkylaryl or heteroaryl ring.

14. The compound of claim 13, wherein ring A has the structure selected from the group consisting of:

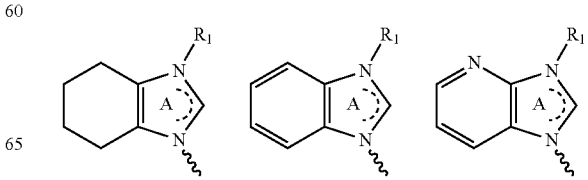

-continued
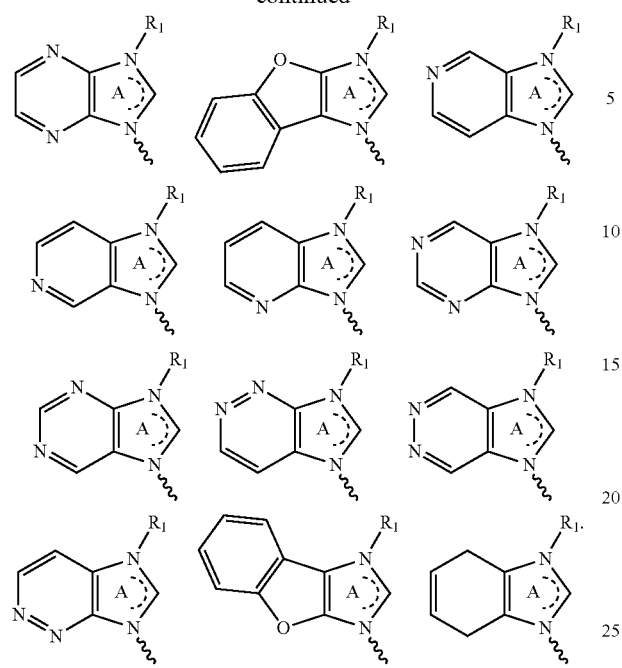
15. The compound of claim 1, wherein $R_5$ is disubstituted, and $R_5$ comprises two adjacent substituents joined to form an aryl, alkylaryl or heteroaryl ring.
16. The compound of claim 1, wherein one of $Z_1$-$Z_4$ is N.
17. The compound of claim 1, wherein at least one of $Z_5$-$Z_8$ is N.
18. The compound of claim 1, wherein one of $Z_5$-$Z_8$ is N.
19. The compound of claim 1, wherein $Y_1$-$Y_2$ is
-continued
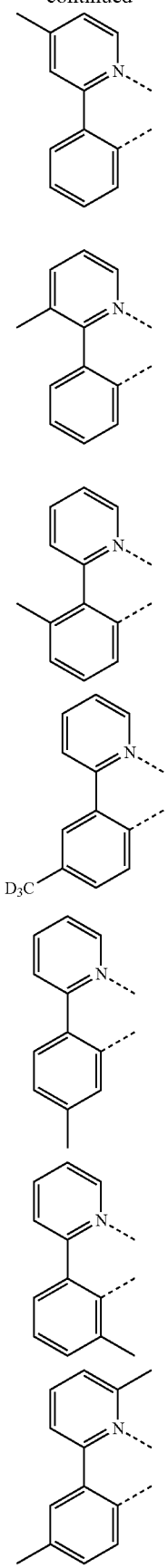

147
-continued
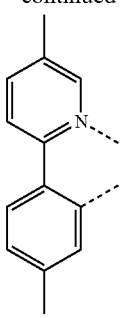
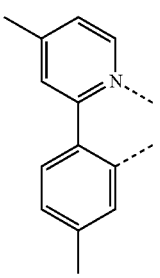
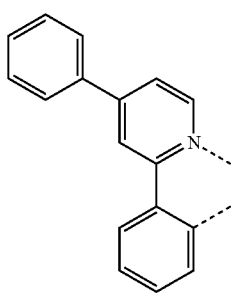
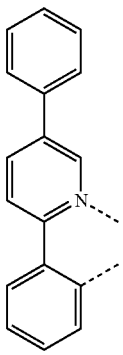
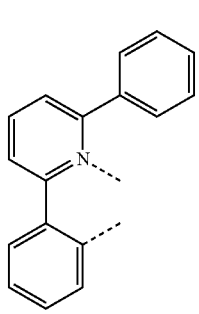
148
-continued
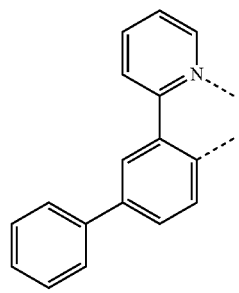
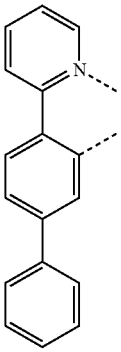
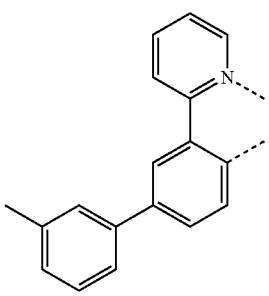
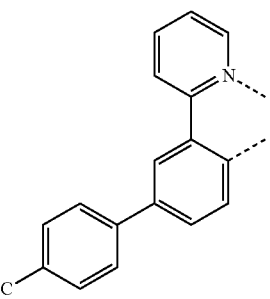
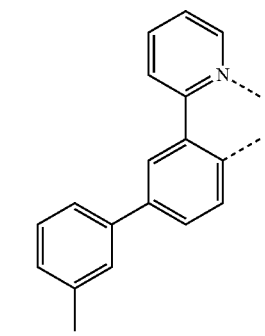

149
-continued
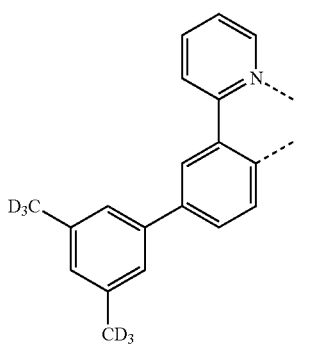
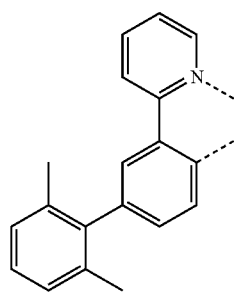
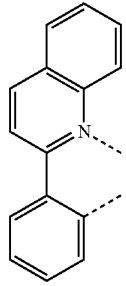
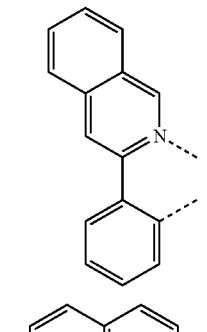
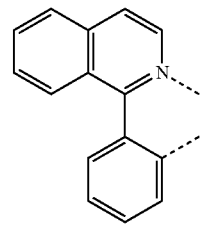
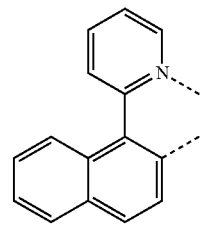
150
-continued
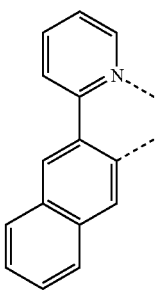
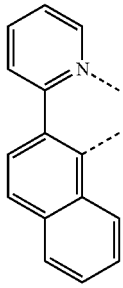
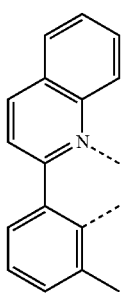
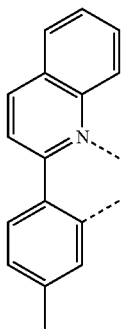
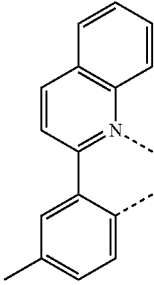

151
-continued
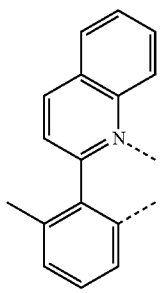
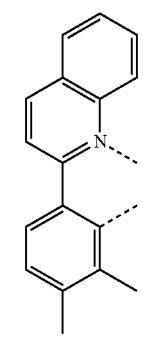
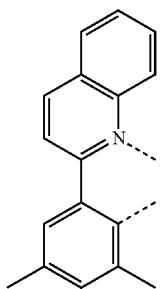
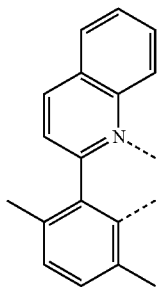
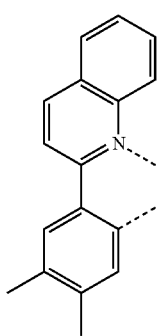
152
-continued
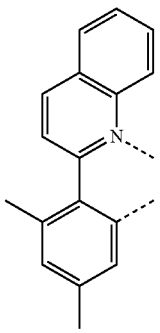
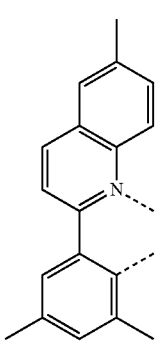
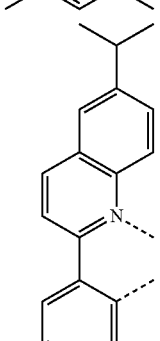
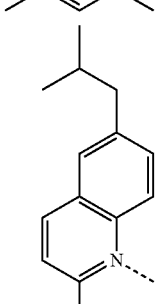
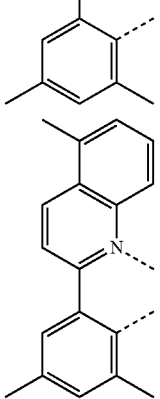

153
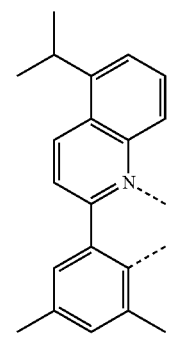
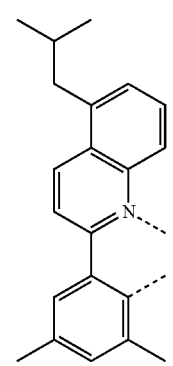
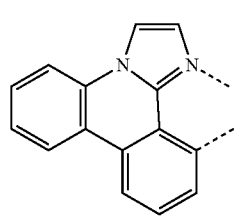
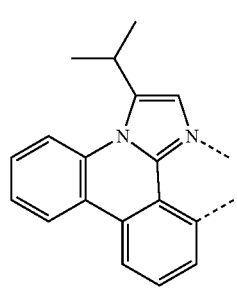
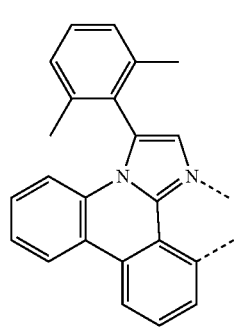
154
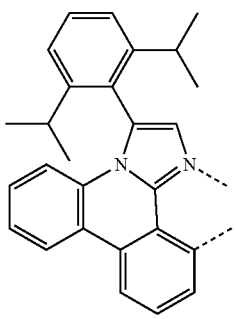
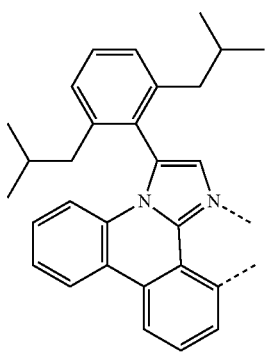
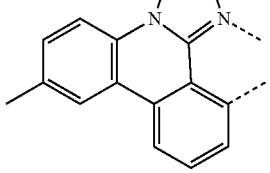
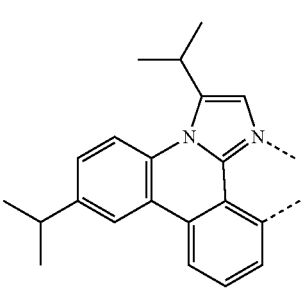
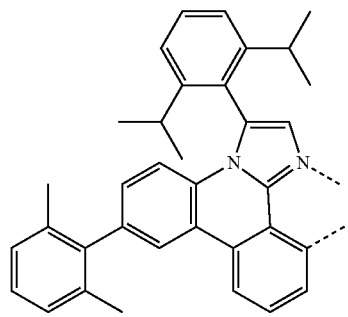

155
-continued
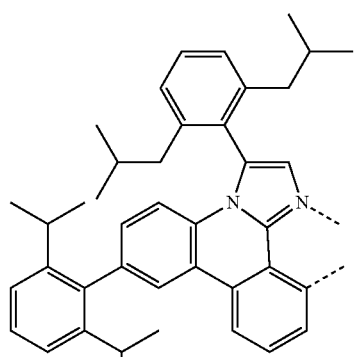
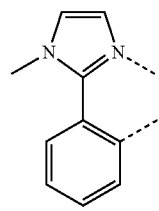
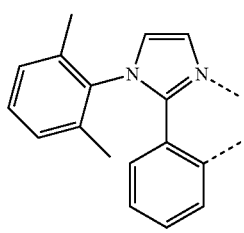
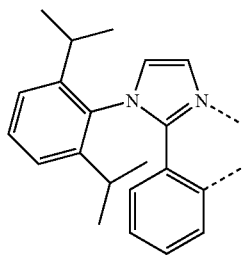
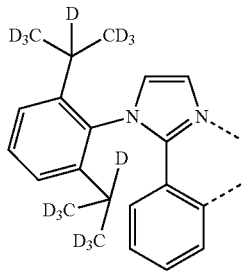
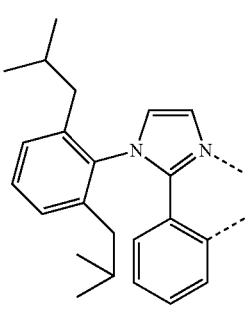
156
-continued
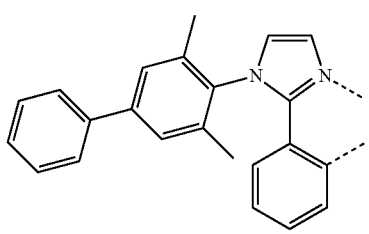
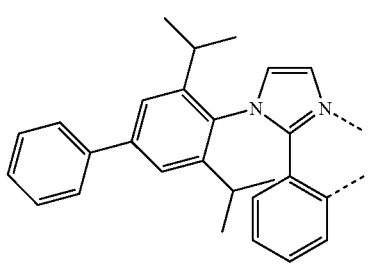
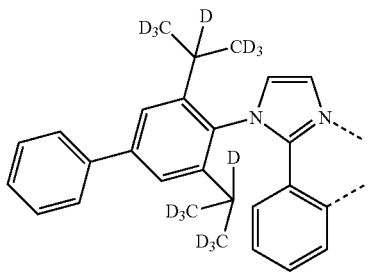
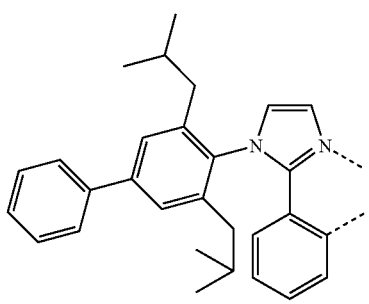
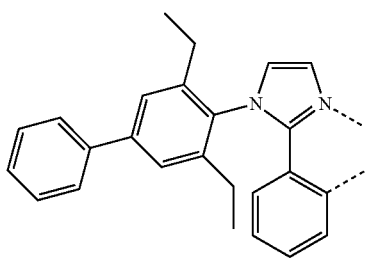
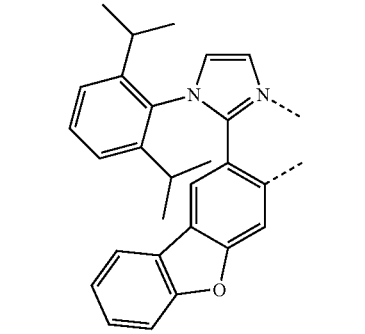

157
-continued
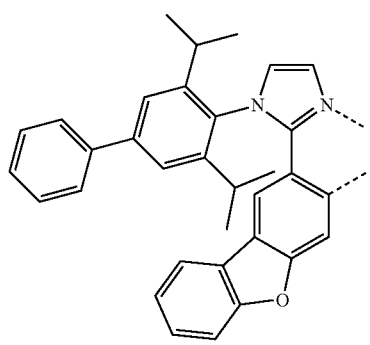
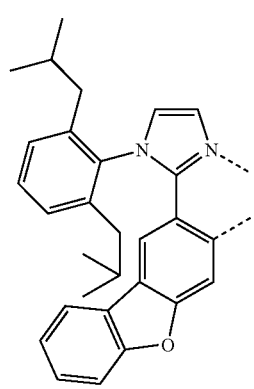
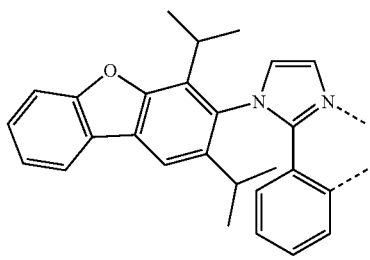
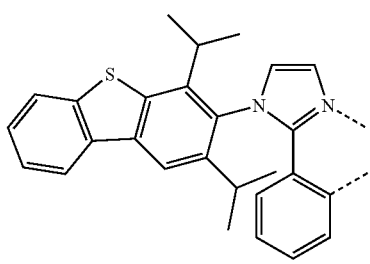
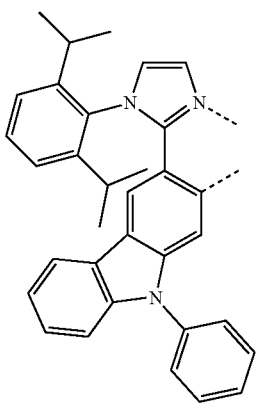
158
-continued
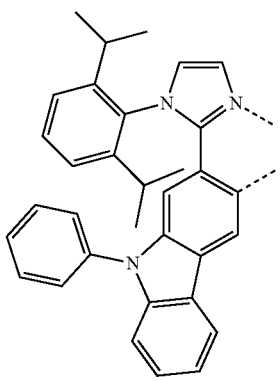
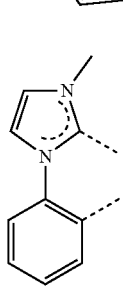
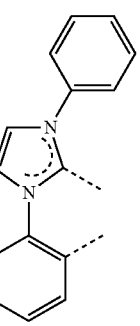
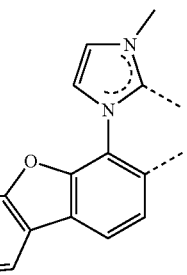
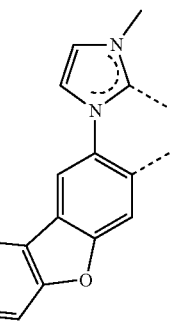

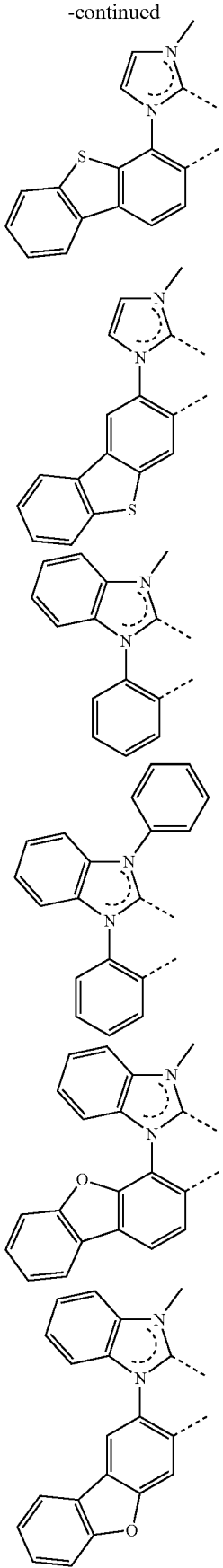
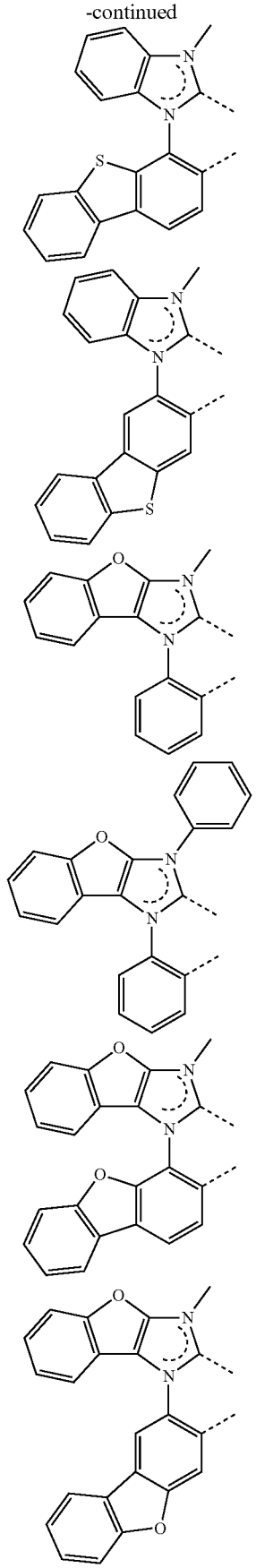

-continued
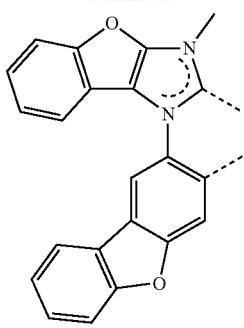
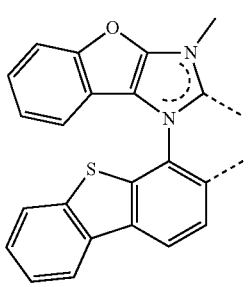
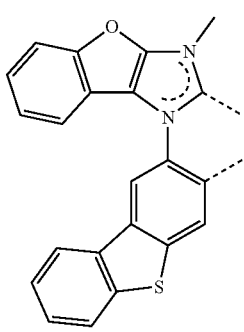
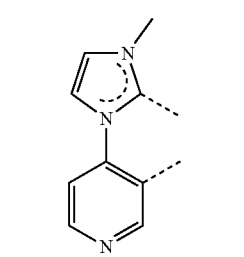
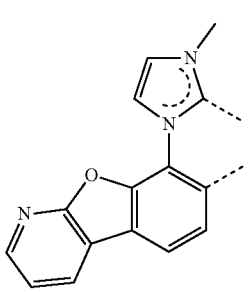
-continued
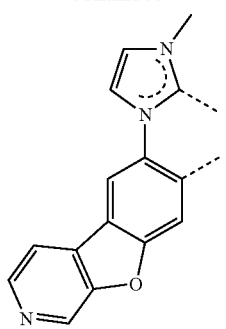
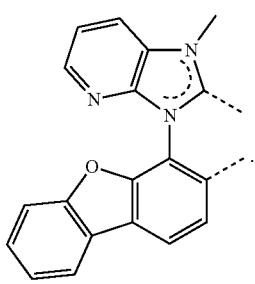
20. The compound of claim 1, wherein n=1.
21. The compound of claim 1, wherein n=2.
22. The compound of claim 1, wherein $X_1$-$X_2$ is selected from the group consisting of
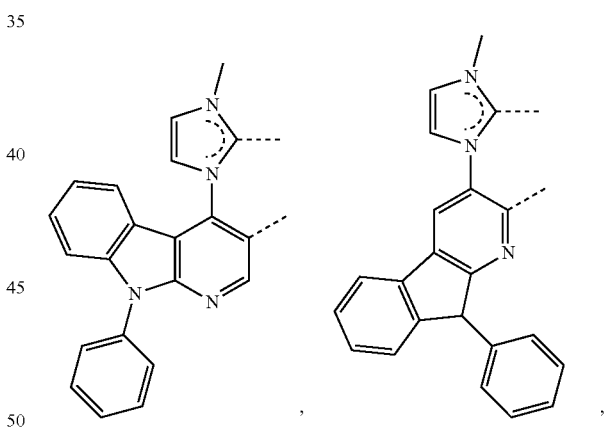
,
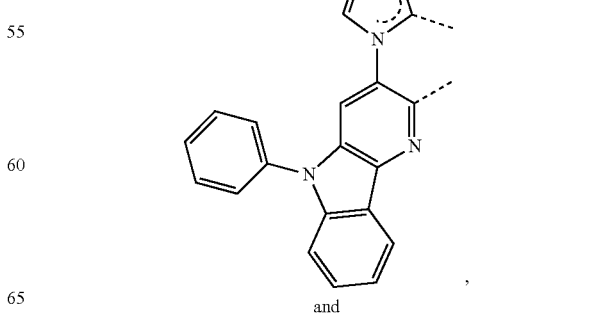
,
and -continued

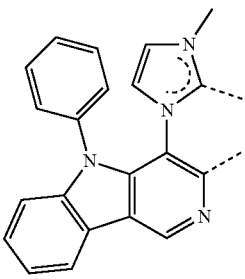

23. The compound of claim 1, wherein the compound is selected from the group consisting of Compound 19

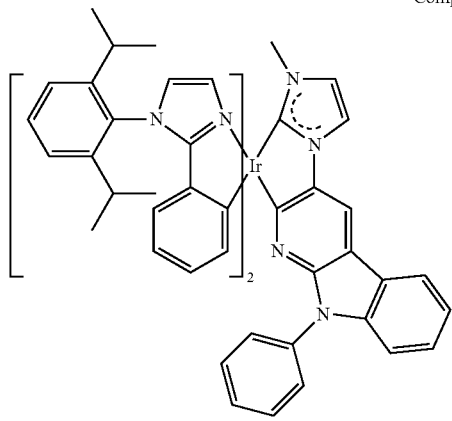

and

Compound 21

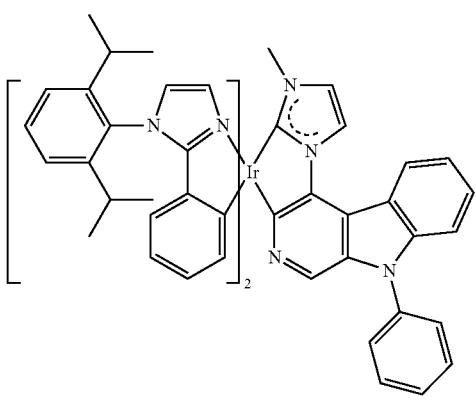

24. The compound of claim 1, wherein ring A is connected to ring B through $Z_1$ and Ring B is connected to the iridium atom by $Z_2$.

25. A first device comprising a first organic light emitting device, further comprising:
an anode;
a cathode; and
an organic layer, disposed between the anode and the cathode, comprising a compound having the formula:

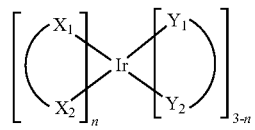

Formula I wherein n=1 or 2;
wherein $X_1$-$X_2$ is a bidentate ligand having the formula:

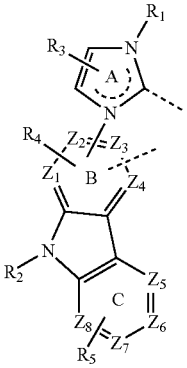

Formula II wherein each of $R_1$, $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R_3$, $R_4$ and $R_5$ may represent mono, di, tri, tetra substitutions, or no substitution;
wherein each of $R_3$, $R_4$ and $R_5$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof, and wherein two adjacent substituents are optionally joined to form into a ring;
wherein each of $Z_1$, $Z_2$, $Z_3$, $Z_4$, $Z_5$, $Z_6$, $Z_7$, and $Z_8$ is independently selected from C, CH or N;
wherein at least one of $Z_1$-$Z_4$ is N;
wherein ring A is connected to ring B through N—C bond; and
wherein $Y_1$-$Y_2$ is a different bidentate ligand other than $X_1$-$X_2$.

26. The first device of claim 25, wherein the first device comprises a device selected from the group consisting of a consumer product, an organic light-emitting device, and a lighting panel.

27. The first device of claim 25, wherein the organic layer is an emissive layer and the compound is an emissive dopant.

28. The first device of claim 25, wherein the organic layer is an emissive layer and the compound is a non-emissive dopant.

29. The first device of claim 25, wherein the organic layer further comprises a host.

30. The first device of claim 29, wherein the host comprises a triphenylene containing benzo-fused thiophene or benzo-fused furan;

wherein any substituent in the host is an unfused substituent independently selected from the group consisting of of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, and $C_nH_{2n}$-$Ar_1$, or the host has no substitutions;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

31. The first device of claim 29, wherein the host comprises a compound selected from the group consisting of: carbazole, dibenzothiphene, dibenzofuran, dibenzoselenophene, azacarbazole, aza-dibenzothiophene, aza-dibenzofuran, and aza-dibenzoselenophene.

32. The first device of claim 29, wherein the host is selected from the group consisting of:

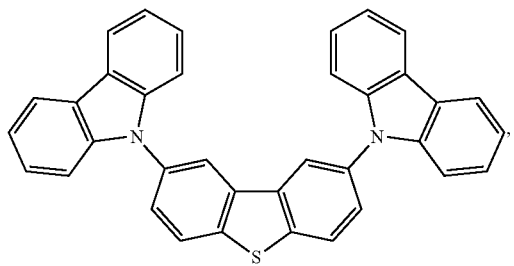

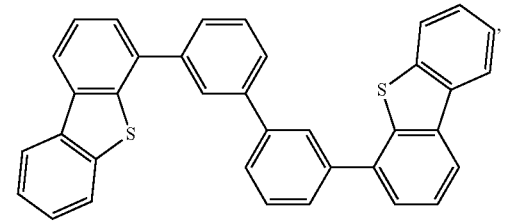

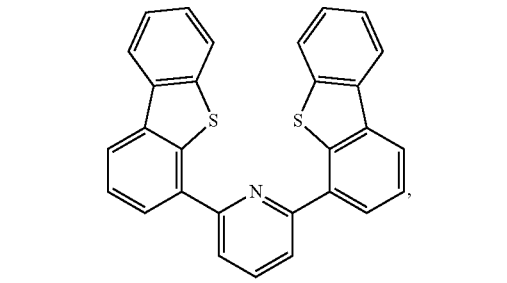

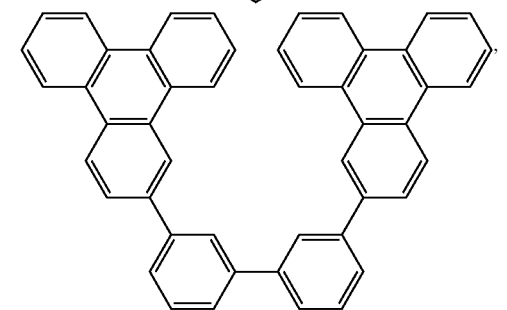

-continued

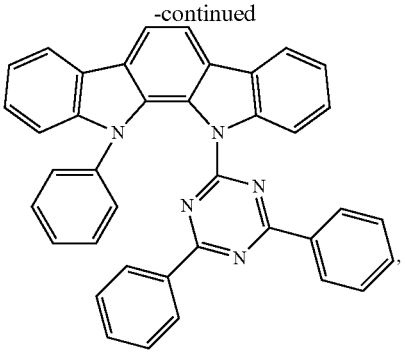

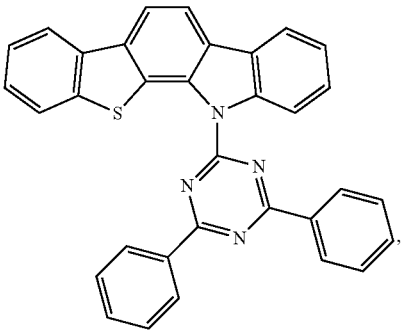

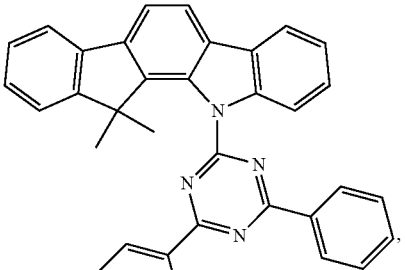

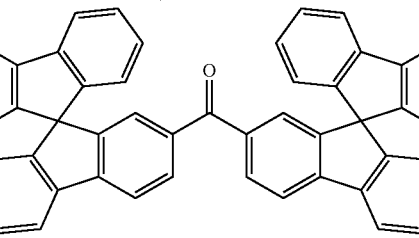

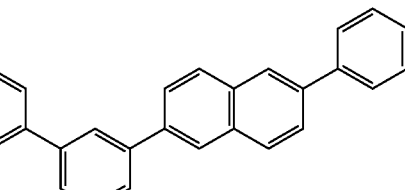

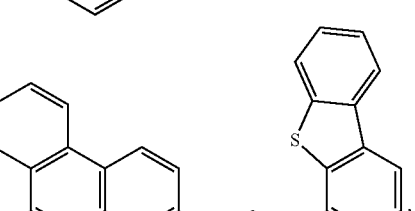

-continued
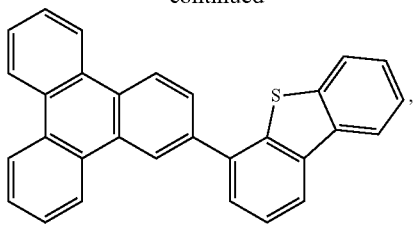
and combinations thereof.
33. The first device of claim 29, wherein the host comprises a metal complex.
* * * * *

UNITED STATES PATENT AND TRADEMARK OFFICE
CERTIFICATE OF CORRECTION

PATENT NO. : 9,773,985 B2  
APPLICATION NO. : 13/798839  
DATED : September 26, 2017  
INVENTOR(S) : Lichang Zeng et al.

Page 1 of 1

It is certified that error appears in the above-identified patent and that said Letters Patent is hereby corrected as shown below:

In the Claims

In Claim 1, Column 141, Line 36, please delete "sulfonyl" and insert -- sulfinyl --

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*